US008795652B1

(12) United States Patent
Michal et al.

(10) Patent No.: US 8,795,652 B1
(45) Date of Patent: Aug. 5, 2014

(54) METHODS AND COMPOSITIONS TO TREAT MYOCARDIAL CONDITIONS

(75) Inventors: Eugene T. Michal, San Francisco, CA (US); Jeffrey Ross, Roseville, MN (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 890 days.

(21) Appl. No.: 11/938,752

(22) Filed: Nov. 12, 2007

Related U.S. Application Data

(60) Division of application No. 10/802,955, filed on Mar. 16, 2004, now Pat. No. 7,294,334, which is a continuation-in-part of application No. 10/414,602, filed on Apr. 15, 2003, now Pat. No. 8,383,158.

(51) Int. Cl.
*C12N 5/02* (2006.01)

(52) U.S. Cl.
USPC .............................. 424/93.7; 607/9

(58) Field of Classification Search
None
See application file for complete search history.

(56) References Cited

U.S. PATENT DOCUMENTS

| 2,512,569 | A | 6/1950 | Saffir |
| 3,144,868 | A | 8/1964 | Jascalevich |
| 3,584,624 | A | 6/1971 | de Ciutiis |
| 3,780,733 | A | 12/1973 | Martinez-Manzor |
| 3,804,097 | A | 4/1974 | Rudie |
| 3,890,976 | A | 6/1975 | Bazell et al. |
| 4,141,973 | A | 2/1979 | Balazs |
| 4,617,186 | A | 10/1986 | Schafer et al. |
| 4,794,931 | A | 1/1989 | Yock |
| 4,818,291 | A | 4/1989 | Iwatsuki et al. |
| 4,842,590 | A | 6/1989 | Tanabe et al. |
| 5,000,185 | A | 3/1991 | Yock |
| 5,024,234 | A | 6/1991 | Leary et al. |
| 5,026,350 | A | 6/1991 | Tanaka et al. |
| 5,049,130 | A | 9/1991 | Powell |
| 5,092,848 | A | 3/1992 | DeCiutiis |
| 5,100,185 | A | 3/1992 | Menke et al. |
| 5,109,859 | A | 5/1992 | Jenkins |
| 5,116,317 | A | 5/1992 | Carson et al. |
| 5,128,326 | A | 7/1992 | Balazs et al. |
| 5,171,217 | A | 12/1992 | March et al. |
| 5,202,745 | A | 4/1993 | Sorin et al. |
| 5,203,338 | A | 4/1993 | Jang |
| 5,242,427 | A | 9/1993 | Bilweis |
| 5,270,300 | A | 12/1993 | Hunziker |
| 5,291,267 | A | 3/1994 | Sorin et al. |
| 5,306,250 | A | 4/1994 | March et al. |
| 5,321,501 | A | 6/1994 | Swanson et al. |
| 5,328,955 | A | 7/1994 | Rhee et al. |
| 5,336,252 | A | 8/1994 | Cohen |
| 5,354,279 | A | 10/1994 | Hofling |
| 5,365,325 | A | 11/1994 | Kumasaka et al. |
| 5,372,138 | A | 12/1994 | Crowley et al. |
| 5,380,292 | A | 1/1995 | Wilson |
| 5,419,777 | A | 5/1995 | Hofling et al. |
| 5,437,632 | A | 8/1995 | Engelson |
| 5,455,039 | A | 10/1995 | Edelman et al. |
| 5,459,570 | A | 10/1995 | Swanson et al. |
| 5,464,395 | A | 11/1995 | Faxon et al. |
| 5,465,147 | A | 11/1995 | Swanson |
| 5,485,486 | A | 1/1996 | Gilhousen et al. |
| 5,499,630 | A | 3/1996 | Hiki et al. |
| 5,516,532 | A | 5/1996 | Atala et al. |
| 5,540,912 | A | 7/1996 | Roorda et al. |
| 5,546,948 | A | 8/1996 | Hamm et al. |
| 5,554,389 | A * | 9/1996 | Badylak et al. ............... 424/558 |
| 5,575,815 | A | 11/1996 | Slepian et al. |
| 5,580,714 | A | 12/1996 | Polovina |
| 5,580,856 | A | 12/1996 | Prestrelski et al. |
| 5,588,432 | A | 12/1996 | Crowley |
| 5,621,610 | A | 4/1997 | Moore et al. |
| 5,631,011 | A | 5/1997 | Wadstrom |
| 5,642,234 | A | 6/1997 | Altman et al. |
| 5,655,548 | A | 8/1997 | Nelson et al. |
| 5,667,778 | A | 9/1997 | Atala |
| 5,669,883 | A | 9/1997 | Scarfone et al. |

(Continued)

FOREIGN PATENT DOCUMENTS

| EP | 0331584 | 9/1989 |
| EP | 0861632 | 9/1998 |

(Continued)

OTHER PUBLICATIONS

PCT International Preliminary Report on Patentability and Written Opinion dated Dec. 24, 2008 for PCT/US2007/013181, 11 pages.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Abbott Cardiovascular Systems in, PCT Search Report dated Feb. 12, 2008, PCT Appln No. PCT/US2007/013181, 17 pages.

(Continued)

*Primary Examiner* — Allison Ford
(74) *Attorney, Agent, or Firm* — Randy Shen; Blakely Sokoloff Taylor & Zafman LLP

(57) ABSTRACT

Methods, devices, kits and compositions to treat a myocardial infarction. In one embodiment, the method includes the prevention of remodeling of the infarct zone of the ventricle using a combination of therapies. The method may include the introduction of structurally reinforcing agents. In other embodiments, agents may be introduced into a ventricle to increase compliance of the ventricle. The prevention of remodeling may include the prevention of thinning of the ventricular infarct zone. Another embodiment includes the reversing or prevention of ventricular remodeling with electro-stimulatory therapy. The unloading of the stressed myocardium over time effects reversal of undesirable ventricular remodeling. These therapies may be combined with structurally reinforcing therapies. In other embodiments, the structurally reinforcing component may be accompanied by other therapeutic agents. These agents may include but are not limited to pro-fibroblastic and angiogenic agents.

7 Claims, 18 Drawing Sheets

(56) References Cited

U.S. PATENT DOCUMENTS

| | | |
|---|---|---|
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon et al. |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett et al. |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,569,441 B2 | 5/2003 | Kunz et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,620,927 B2 | 9/2003 | Bulpitt et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,663,881 B2 | 12/2003 | Kunz et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,726,923 B2 | 4/2004 | Iyer et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |

(56) References Cited

U.S. PATENT DOCUMENTS

| | | |
|---|---|---|
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,187,621 B2 | 5/2012 | Michal et al. |
| 8,192,760 B2 | 6/2012 | Hossainy et al. |
| 2001/0023349 A1 | 9/2001 | Van Tassel et al. |
| 2001/0055615 A1 | 12/2001 | Wallace et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0114505 A1 | 6/2003 | Ueno et al. |
| 2003/0175410 A1 | 9/2003 | Campbell et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2003062089 | 3/2003 |
| JP | 2007009185 | 1/2007 |
| JP | 2006523507 | 10/2009 |
| WO | WO-92/10142 | 6/1992 |
| WO | WO-9315781 | 8/1993 |
| WO | WO-9522316 | 8/1995 |
| WO | WO-98/30207 | 7/1998 |
| WO | WO-98/54301 | 12/1998 |
| WO | WO-9953943 | 10/1999 |
| WO | WO-00/16818 | 3/2000 |
| WO | WO-0054661 | 9/2000 |
| WO | WO-00/71196 | 11/2000 |
| WO | WO-01/24775 | 4/2001 |
| WO | WO-0124842 | 4/2001 |
| WO | WO-01/45548 | 6/2001 |
| WO | WO-01/49357 | 7/2001 |
| WO | WO-0200173 | 1/2002 |
| WO | WO-0204008 | 1/2002 |
| WO | WO-02/28450 | 4/2002 |
| WO | WO-02/40070 | 5/2002 |
| WO | WO-02/072166 | 9/2002 |
| WO | WO-02/087623 | 11/2002 |
| WO | WO-03005961 | 1/2003 |
| WO | WO-03/022909 | 3/2003 |
| WO | WO-03022324 | 3/2003 |
| WO | WO-03/027234 | 4/2003 |
| WO | WO-03026492 | 4/2003 |
| WO | WO-03/064637 | 8/2003 |
| WO | WO-2004/000915 | 12/2003 |
| WO | WO-2004/050013 | 6/2004 |
| WO | WO-2004058305 | 7/2004 |
| WO | WO-2004060346 | 7/2004 |
| WO | WO-2004/066829 | 8/2004 |
| WO | WO-2004/091592 | 10/2004 |
| WO | WO-2004098669 | 11/2004 |
| WO | WO-2005/061019 | 7/2005 |
| WO | WO-2005/067890 | 7/2005 |
| WO | WO-2006014570 | 2/2006 |
| WO | WO-2006027549 | 3/2006 |
| WO | WO-2006/039704 | 4/2006 |
| WO | WO-2006/113407 | 10/2006 |
| WO | WO-2006113407 | 10/2006 |
| WO | WO-2007/048831 | 3/2007 |
| WO | WO-2007145909 | 12/2007 |

OTHER PUBLICATIONS

Abbott Cardiovascular Systems in, PCT Search Report dated Jan. 31, 2007, PCT Appln No. PCT/US2006/014021, 11 pages.

Abbott Cardiovascular Systems in, PCT Search Report dated Mar. 27, 2008, PCT Appln No. PCT/US2007/003614, 18 pages.

Advanced Cardiovascular Systems, Inc. et al., PCT International Preliminary Report on Patentability dated Jun. 19, 2007, PCT Appln. No. PCT/US2005/045627.

Advanced Cardiovascular Systems, Inc., PCT International Preliminary Report on Patentability dated Nov. 3, 2005, PCT Appln. No. PCT/US2004/011356, 6 pages.

Advanced Cardiovascular Systems, Inc., PCT International Search Report and Written Opinion mailed Oct. 13, 2006, PCT Appln No. PCT/US2005/045627.

Advanced Cardiovascular Systems, Inc., PCT International Search Report dated Feb. 9, 2004, PCT Appln. No. PCT/US03/30464, 5 pages.

Advanced Cardiovascular Systems, Inc., PCT International Search Report dated Jan. 28, 2004, PCT Appln. No. PCT/US03/18360, 7 pages.

Advanced Cardiovascular Systems, Inc., PCT Invitation to Pay Additional Fees mailed Nov. 4, 2003, PCT Appln No. PCT/US03/18360, 3 pages.

(56) References Cited

OTHER PUBLICATIONS

Advanced Cardiovascular Systems, Inc., PCT Search Report and Written Opinion dated Nov. 24, 2004, PCT Appln. No. PCT/US2004/011356, 12 pages.

Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), Apr. 1997, pp. 2233-2244.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at: http://www.ncbi.nlm.nih.gov/entrez/query.fcgi?cmd=Retrieve&db=PubMed, Nov. 1997, pp. 229-234.

Anderson, James M., et al., "Biodegradation and biocompatibility of PLA and PLGA microspheres", Advanced Drug Delivery Reviews 28, (1997), pp. 5-24.

Assmus, B., et al., "Transplantation of Progenitor Cells and Regeneration Enhancement in Acute Myocardial Infarction (TOPCARE-AMI)", Clinical Investigation and Reports, Oct. 8, 2002, pp. 3009-3017, Department of Molecular Cardiology and Department of hematology (H.M., D.H.) University of Frankfurt, Frankfurt, germany. Circulation Available at http://www.circulationha.org DOI: 10.116.

Baxter, "FloSeal Matrix Hemostatic Sealant", downloaded from the Internet on Nov. 14, 2002, from: http://www.fusionmed.com/docs/surgeon/default.asp, 2 pages.

Berger, et al., "Poly-L-cysteine", J. Am. Chem. Soc., 78(17), Sep. 5, 1956, pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), Aug. 1996, pp. 107-112.

Boland, E. D., "Electrospinning Collagen and Elastin: Preliminary Vascular Tissue Engineering", Frontiers in Bioscience, vol. 9, May 1, 2004, pp. 1422-1432.

Brust, G., "Polyimides", downloaded from the Internet at: http://www.pslc.ws/macrog/imide.htm, 2005, 4 pages.

Buschmann, I., et al., "Arteriogenesis versus angiogenesis: Two mechanisms of vessel growth", News Physiol. Sci., vol. 14, Jun. 1999, 121-125.

Canderm Pharma, "Technical Dossier: Artecoll", downloaded from the Internet on Oct. 22, 2002 from: http://www.canderm.com/artecoll/tech.html, 3 pages.

Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.

Caplan, Michael J., et al., "Dependence on pH of polarized sorting of secreted proteins", Dept. of Cell Biology and Dept. of Pathology, Yale University School of Medicine, Nature, vol. 329, Oct. 15, 1987, p. 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), Mar. 1990, pp. 1673-1675.

Chandy, et al., "The development of porous alginate/elastin/PEG composite matrix for cardiovascular engineering", Journal of Biomaterials Applications, vol. 17, Apr. 2003, pp. 287-301.

Choi, Young Seon, et al., "Study on gelatin-containing artificial skin: I. Preparation and characteristics of novel gelatin-alginate sponge", Biomaterials, vol. 20, 1999, 409-417.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), Oct. 3, 1997, pp. 24999-25005.

Creemers, E., et al., "Matrix Metalloproteinase Inhibition After Myocardial Infarction: A New Approach to Prevent Heart Failure?", Circ. Res., vol. 89, 2001, pp. 201-210.

Crivello, et al., "Synthesis and Photoinitiated Cationic Polymerization of Monomers with the Silsesquioxane Core", J Polym Science: Part A: Polymer Chemistry 35, 1997, pp. 407-425.

Davis, M. E., et al., "Injectable Self-Assembling Peptide Nanofibers Create Intramyocardial Microenvironments for Endothelial Cells", Circulation, 111, Feb. 2005, pp. 442-450.

De Rosa, et al., "Biodegradable Microparticles for the Controlled Delivery of Oligonucleotides", International Journal of Pharmaceutics, 242, Aug. 21, 2002, pp. 225-228.

Desai, M., et al., "Polymer bound EDC (P-EDC): A convenient reagent for formation of an amide bond", Tetrahedron Letters, 34(48), Abstract downloaded from the Internet at: http://www.sciencedirect.com, 1 page, Nov. 1993, pp. 7685-7688.

Dinbergs, et al., "Cellular response to transforming growth factor-$\beta1$ and basic fibroblast growth factor depends on release kinetics and extracellular matrix interactions", The Journal of Biological Chemistry, vol. 271, No. 47, Nov. 1996, pp. 29822-29829.

Dong, Zhanfeng, et al., "Alginate/gelatin blend films and their properties for drug controlled release", Journal of Membrane Science, vol. 280, 2006, pp. 37-44.

Edelman, "Controlled and modulated release of basic fibroblast growth factor", Biomaterials, vol. 12, Sep. 1999, pp. 619-626.

Etzion, S., et al., "Influence of Embryonic Cardiomyocyte Transplantation on the Progression of Heart Failure in a Rat Model of Extensive Myocardial Infarction", J. Mol. Cell Cardiol., 33, May 2001, pp. 1321-1330.

Ferrara, N., "Role of Vascular Endothelial Growth Factor in the Regulation of Angiogenesis", Kidney International, 56(3), Abstract downloaded from the Internet at: http://www.nature.com/ki/journal/v56/n3/abs/4490967a.html, 1 page, 1999, pp. 794-814.

Fuchs, S., et al., "Catheter-Based Autologous Bone Marrow Myocardial Injection in No-Option Patients with Advanced Coronary Artery Disease", J. Am. Coll. Cardiol., 41(10), 2003, pp. 1721-1724.

Fukumoto, S., et al., "Protein Kinase C $\delta$; Inhibits the Proliferation of Vascular Smooth Muscle Cells by Suppressing G1 Cyclin Expression", The Journal of Biological Chemistry, 272(21), May 1997, pp. 13816-13822.

Giordano, F., et al., "Angiogenesis: The Role of the Microenvironment in Flipping the Switch", Current Opinion in Genetics and Development, 11, 2001, pp. 35-40.

Gossler, et al., "Transgenesis by means of blastocyst-derived embryonic stem cell lines", Proc. Natl. Acad. Sci. USA, 83, Dec. 1986, pp. 9065-9069.

Grafe, T. H., "Nanofiber Webs from Electrospinning", Presented at the Nonwovens in Filtration—Fifth International Conference, Stuttgart, Germany, Mar. 2003, pp. 1-5.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, Mar. 1994, pp. 1600-1603.

Grund, F., et al., "Microembolization in Pigs: Effects on Coronary Blood Flow and Myocardial Ischemic Tolerance", Am. J. Physiol., 277 (Heart Circ. Physiol. 46), 1999, pp. H533-H542.

Gupta, et al., "Changes in Passive Mechanical Stiffness of Myocardial Tissue with Aneurysm Formation", Circulation, 89(5), May 1994, pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, Jan. 1995, pp. 284-288.

Hashimoto, T., et al., "Development of Alginate Wound Dressings Linked with Hybrid Peptides Derived from Laminin and Elastin", Biomaterials, 25, 2004, pp. 1407-1414.

Haugland, et al., "Dialkylcarbocyanine and Dialkylaminostryryl Probes", Handbook of Fluorescent Probes and Research Products, Molecular Probes, Inc., 2002, pp. 530-534.

Haugland, et al., "Membrane-permeant reactive tracers", Handbook of Fluorescent Probes and Research Products, Molecular Probes, Inc., 2002, pp. 458-553.

(56) References Cited

OTHER PUBLICATIONS

Heeschen, C., et al., "Nicotine Stimulates Tumor Angiogenesis", American College of Cardiology, 37(2) Supplement A, Abstract downloaded from the Internet at: http://24.132.160.238/ciw-01acc/abstract_search_author.cfm?SearchName=Heeschen, 1 page, Feb. 2001, pp. 1A-648A.

Helisch, A., et al., "Angiogenesis and arteriogenesis—not yet for prescription", NEUE Diagnostische Und Therap. Verfahren, Z Kardiol 89, 2000, pp. 239-244.

Hendel, R. C., et al., "Effect of Intracoronary Recombinant Human Vascular Endothelial Growth Factor on Myocardial Perfusion: Evidence for a Dose-Dependent Effect", Circulation, 101, 2000, pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at: http://diabetes.diabetesjournals.org/cgi/content/abstract/44/8/936, 1 page, 1995, pp. 936-946.

Hoffman, "Hydrogels for Biomedical Applications", Advanced Drug Delivery Reviews, vol. 43, 2002, pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at: http://www.nature.com, 1 page, Apr. 1998, pp. 799-801.

Horan, R.L., et al., "In Vitro Degradation of Silk Fibroin", Biomaterials, vol. 26, 2004, pp. 3385-3393.

Hovinen, J., et al., "Synthesis of 3'-functionalized oligonucleotides on a single solid support", Tetrahedron Letters, 34(50), Abstract downloaded from the Internet at: http://www.sciencedirect.com, 1 page, Dec. 1993, pp. 8169-8172.

Huang, K., et al., "Synthesis and Characterization of Self-Assembling Block Copolymers Containing Bioadhesive End Groups", Biomacromolecules, 3(2), 2002, pp. 397-406.

Hutcheson, K., et al., "Comparison of Benefits on Myocardial Performance of Cellular Cardiomyoplasty with Skeletal Myoblasts and Fibroblasts", Cell Transplantation, 9(3), 2000, pp. 359-368.

Huynh, T. V., et al., "Constructing and Screening cDNA Libraries in Agt10 and Agt11", Chapter 2 in DNA Cloning, vol. 1: A Practical Approach, ed. by D.M. Glover, 1985, pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, Jul. 1990, pp. 80-86.

Iskandrian, A. S., et al., "Nuclear Cardiac Imaging: Principles and Applications", second edition, F.A. Davis Co., Philadelphia, cover page, title page and TOC, 1996, 5 pages.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, Feb. 21, 1997, pp. 829-837.

Johnson, et al., "The stabilization and encapsulation of human growth hormone into biodegradable microspheres", Pharmaceutical Research, vol. 14, No. 6, 1997, pp. 730-735.

Jonasson, P., et al., "Denatured states of human carbonic anhydrase II: an NMR study of hydrogen/deuterium exchange at tryptophan-indole-Hn sites", FEBS Letters, 445, 1999, pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, Apr. 9, 1999, pp. 251-259.

Kaplan, D.L., et al., "Spiderless Spider Webs", Nature Biotechnology, vol. 20, 2002, pp. 239-240.

Kawai, et al., "Accelerated tissue regeneration through incorporation of basic fibroblast growth factor-impregnated gelatin microspheres into artificial dermis", Biomaterials, 21(5), Mar. 2002, pp. 489-499.

Kawasuji, M., et al., "Therapeutic Angiogenesis with Intramyocardial Administration of Basic Fibroblast Growth Factor", Ann Thorac Surg, 69, Abstract downloaded from the Internet at: http://ats.ctsnetjournals.org/cgi/content/abstract/69/4/1155, 2 pages, 2000, pp. 1155-1161.

Kelley, et al., "Restraining Infarct Expansion Preserves Left Ventricular Geometry and Function After Acute Anteroapical Infarction", Circulation, 99, 1999, pp. 135-142.

Kelly, E. B., "Advances in Mammalian and Stem Cell Cloning", Genetic Engineering News, vol. 23, No. 7, Apr. 1, 2003, pp. 17-18 & 68.

Khademhosseini, et al., "Microscale Technologies for Tissue Engineering and Biology", PNAS, vol. 103, No. 8, Feb. 21, 2006, pp. 2480-2487.

Kim, D., et al., "Glow Discharge Plasma Deposition (GDPD) Technique for the Local Controlled Delivery of Hirudin from Biomaterials", Pharmaceutical Research, 15(5), 1998, pp. 783-786.

Kim, Ung-Jin, et al., "Structure and Properties of Silk Hydrogels", Biomacromolecules, vol. 5(3), 2004, pp. 786-792.

Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, 1990, pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, Jan. 1999, pp. 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, 1997, pp. 159-192.

Klugherz, Bruce D., et al., "Gene delivery from a DNA controlled-release stent in porcine coronary arteries", Nature Biotechnology, vol. 18, Nov. 2000, pp. 1181-1184.

Kohilas, K., et al., "Effect of prosthetic titanium wear debris on mitogen-induced monocyte and lymphoid activation", John Hopkins University, Dept. of Orthopaedic Surgery, Apr. 1999, pp. 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, Jan. 2001, pp. 1848-1853.

Kwok, C., et al., "Design of Infection-Resistant Antibiotic-Releasing Polymers: I. Fabrication and Formulation", Journal of Controlled Release, 62, 1999, pp. 289-299.

Laboratory of Liposome Research, "Liposomes: General Properties", downloaded from the Internet on Feb. 9, 2006 at: http://www.unizh.ch/onkwww/lipos.htm, 5 pages.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), 2000, pp. 795-802.

Leibovich, S. J., et al., "Macrophage-Induced Angiogenesis is Mediated by Tumour Necrosis Factor-α", Nature, vol. 329, Oct. 15, 1987, pp. 630-632.

Leor, J., et al., "Bioengineered Cardiac Grafts—A New Approach to Repair the Infarcted Myocardium?", Circulation, 102[suppl III], 2000, pp. III-56-III-61.

Leor, J., et al., "Gene Transfer and Cell Transplant: An Experimental Approach to Repair a 'Broken Heart'", Cardiovascular Research, 35, 1997, pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at: http://www.ncbi.nlm.nih.gov/entrez/query.fcgi?cmd=Retrieve&db=pubmed, 1 page, 1995, pp. 695-703.

Lewin, B., "Repressor is Controlled by a Small Molecule Inducer", Genes VII, Oxford University Press, 7th ed., 2000, pp. 277-280.

Li, et al., "Cell Therapy to Repair Broken Hearts", Can. J. Cardiol., vol. 14, No. 5, May 1998, pp. 735-744.

(56) References Cited

OTHER PUBLICATIONS

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, 2000, Chapter 33.
Li, J., et al., "PR39, A Peptide Regulator of Angiogenesis", Nature Medicine, 6(1), Jan. 2000, pp. 49-55.
Li., Y. Y., et al., "Differential Expression of Tissue Inhibitors of Metalloproteinases in the Failing Human Heart", Circulation, 98(17), 1998, pp. 1728-1734.
Lindsey, M., et al., "Selective Matrix Metalloproteinase Inhibition Reduces Left Ventricular Remodeling but does not Inhibit Angiogenesis after Myocardial Infarction", Circulation, 105(6), 2002, pp. 753-758.
Long, D. M., et al., "Self-Cleaving Catalytic RNA", FASEB Journal, 7, 1993, pp. 25-30.
Lopez, J. J., et al., "Angiogenic potential of perivascular delivered aFGF in a porcine model of chronic myocardial ischemia", The American Physiological Society, 0363-6135/98, 1998, H930-H936.
Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, 1998, pp. 272-281.
Lu, L., et al., "Biodegradable Polymer Scaffolds for Cartilage Tissue Engineering", Clinical Orthopaedics and Related Research, Carl T. Brighton (ed.). No. 391S, 2001, pp. S251-270.
Luo, Y., et al., "Cross-linked Hyaluronic Acid Hydrogel Films: New Biomaterials for Drug Delivery", Journal of Controlled Release, 69, 2000, pp. 169-184.
Lutolf, M., et al., "Synthesis and Physicochemical Characterization of End-Linked Poly(ethylene glycol)-co-peptide Hydrogels Formed by Michael-Type Addition", Biomacromolecules, vol. 4, 2003, pp. 713-722.
Lyman, M. D., et al., "Characterization of the Formation of Interfacially Photopolymerized Thin Hydrogels in Contact with Arterial Tissue", Biomaterials, 17(3), 1996, pp. 359-364.
Mansour, S., et al., "Disruption of the proto-oncogene int-2 in mouse embryo-derived stem cells: a general strategy for targeting mutations to non-selectable genes", Nature, 336, 1988, pp. 348-352.
Martin, S. L., et al., "Total Synthesis and Expression in *Escherichia coli* of a Gene Encoding Human Tropoelastin", Gene, 1995, Abstract, 1 page.
McDevitt, T., et al., "In vitro Generation of Differentiated Cardiac Myofibers on Micropatterned Laminin Surfaces", J. Biomed Mater Res., 60, 2002, pp. 472-479.
Meinel, L., et al., "The Inflammatory Responses to Silk Films In Vitro and In Vivo", Biomaterials, vol. 26, 2005, pp. 147-155.
Narmoneva, D. A., et al., "Self-assembling short oligopeptides and the promotion of angiogenesis", Biomaterials, 26, 2005, pp. 4837-4846.
Nazarov, R., et al., "Porous 3-D Scaffolds from Regenerated Silk Fibroin", Biomacromolecules, vol. 5(3), 2004, pp. 718-726.
Nguyen, K. T., et al., "Photopolymerizable Hydrogels for Tissue Engineering Applications", Biomaterials, 23, 2002, pp. 4307-4314.
Nikolic, S. D., et al., "New Angiogenic Implant Therapy Improves Function of the Ischemic Left Venticle", Supplement to Circulation; Abstracts From Scientific Sessions 2000, 102(18), Oct. 2000, pp. II-689, Abstract 3331.
Nikolic, Serjan D., et al., "Novel means to improve coronary blood flow", Clinical Science, Abstracts from Scientific Sessions, 2000, pp. II-689.
Nitinol Technical Information, "NiTi Smart Sheets", downloaded from the Internet on Dec. 10, 2002 at: http://www.sma-inc.com/information.html, 1 page.
Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, Dec. 1986, pp. 2649-2658.
Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), 1977, pp. 90-92.
Ozbas, B., et al., "Salt-Triggered Peptide Folding and Consequent Self-Assembly into Hydrogels with Tunable Modulus", Macromolecules, 37(19), 2004, pp. 7331-7337.
Ozbas-Turan, S., "Controlled Release of Interleukin-2 from Chitosan Microspheres", Journal of Pharmaceutical Sciences, 91(5), May 2002, pp. 1245-1251.
Palmiter, R., et al., "Germ-Line Transformation of Mice", Ann. Rev. Genet., 20, 1986, pp. 465-499.
Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, 1982, pp. 323-342.
Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, Jun. 2004, 2 pages.
Penta, K., et al., "Del1 Induces Integrin Signaling and Angiogenesis by Ligation of $\alpha V\beta 3$", J. Biolog. Chem., 274(16), Apr. 1999, pp. 11101-11109.
Perin, E. C., et al., "Transendocardial, Autologous Bone Marrow Cell Transplantation for Severe, Chronic, Ischemic Heart Failure", Circulation, 2003, 1 page.
Pouzet, B., et al., "Is Skeletal Myoblast Transplantation Clinically Relevant in the Era of Angiotensin-Converting Enzyme Inhibitors?", Circulation, 104 [suppl I], Sep. 2001, pp. I-223-I-228.
Prather, et al., "Nuclear Transplantation in Early Pig Embryos", Biol. Reprod., 41, 1989, pp. 414-418.
Prosci Incorporated, "ILPIP (CT) Peptide", 1 page.
Quellec, P., et al., "Protein Encapsulation Within Polyethylene Glycol-coated Nanospheres. 1. Physicochemical Characterization", J. Biomed. Mater. Res., 42(1), 1998, Abstract, 1 page.
Ramirez-Solis, R., et al., "Gene Targeting in Embryonic Stem Cells", Methods in Enzymology, 225, 1993, pp. 855-878.
Rowley, et al., "Alginate Hydrogels as Synthetic Extracellular Matrix Materials", Biomaterials, 20(1), 1999, pp. 45-53.
Sawhney, A. S., et al., "Bioerodible Hydrogels Based on Photopolymerized Poly(ethylene glycol)-co-poly(a-hydroxy acid) Diacrylate Macromers", Macromolecules, 26(4), 1993, pp. 581-587.
Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at: http://stemcells.alphamedpress.org/cgi/content/full/20/6/585, 2002, pp. 585-587.
Segura, T., et al., "Crosslinked Hyaluronic Acid Hydrogels: A Strategy to Functionalize and Pattern", Biomaterials, vol. 26(4), Feb. 2005, pp. 359-371.
Segura, T., et al., "DNA delivery from hyaluronic acid-collagen hydrogels via a substrate-mediated approach", Biomaterials, vol. 26, 2005, pp. 1575-1584.
Segura, T., et al., "Substrate-Mediated DNA Delivery: Role of the Cationic Polymer Structure and Extent of Modification", Journal of Controlled Release, 93, 2003, pp. 69-84.
Segura, T., et al., "Surface-Tethered DNA Complexes for Enhanced Gene Delivery", Bioconjugate Chem, 13(3), 2002, pp. 621-629.
Shibasaki, F., et al., "Suppression of Signalling Through Transcription Factor NF-AT by Interactions Between Calcineurin and Bcl-2", Nature, 386(6626), Abstract downloaded from the Internet at: http://www.ncbi.nlm.nih.gov/entrez/query.fcgi?CMD=Text&DB=pubmed, 1 page, 1997.
Shin, H., et al., "Attachment, Proliferation, and Migration of Marrow Stromal Osteoblasts Cultured on Biomimetic Hydrogels Modified with an Osteopontin-Derived Peptide", Biomaterials, 25, 2004, pp. 895-906.
Shin, H., et al., "In vivo bone and soft tissue response to injectable, biodegradable oligo(poly(ethylene glycol) fumarate) hydrogels", Biomaterials 24, Elseview Science Ltd., 2003, pp. 3201-3211.
Shu, Z., et al., "Disulfide-crosslinked hyaluronan-gelatin hydrogel films: a covalent mimic of the extracellular matrix for in vitro cell growth", Biomaterials, vol. 24(21), Sep. 2003, pp. 3825-3834.

(56) References Cited

OTHER PUBLICATIONS

Shu, Zheng, et al., "In situ crosslinkable hyaluronan hydrogels for tissue engineering", Biomaterials, vol. 25, 2004, pp. 1339-1348.
Simons, M., et al., "Clinical trials in coronary angiogenesis: Issues, problems, consensus, An expert panel summary", Angiogenesis Research Center, American Heart Association, Inc., Sep. 12, 2000, pp. 1-14.
Spenlehauer, G., et al., "In vitro and in vivo degradation of poly(D,L lactide/glycolide) type microspheres made by solvent evaporation method", Biomaterials, vol. 10, Oct. 1989, pp. 557-563.
Spinale, F. G., "Matrix Metalloproteinases—Regulation and Dysregulation in the Failing Heart", Circ. Res., 90, 2002, pp. 520-530.
Springer, M., et al., "Angiogenesis Monitored by Perfusion with a Space-Filling Microbead Suspension", Mol. Ther., 1(1), Abstract downloaded from the Internet at: http://www.ncbi.nlm.nih.gov/entrez/query.fcgi?cmd=Retrieve&db=PubMed, 1 page, 2000, pp. 82-87.
Storm, G., et al., "Surface Modification of Nanoparticles to Oppose Uptake by the Mononuclear Phagocyte System", Advanced Drug Delivery Reviews, 17(1), Abstract downloaded from the Internet at: http://www.sciencedirect.com, 1 page, Oct. 1995, pp. 31-48.
Strauer, B., et al., "Repair of Infarcted Myocardium by Autologous Intracoronary Mononuclear Bone Marrow Cell Transplantation in Humans", Circulation, 106, 2002, pp. 1913-1918.
Tybulewicz, V., et al., "Neonatal lethality and lymphopenia in mice with a homozygous disruption of the c-abl proto-oncogene", Cell, 65(7), Abstract downloaded from the Internet at: http://www.sciencedirect.com, 2 pages, Jun. 1991, pp. 1153-1163.
Unger, E. F., et al., "Effects of a Single Intracoronary Injection of Basic Fibroblast Growth Factor in Stable angina Pectoris", Am. J. Cardiol, 85(12), Abstract downloaded from the Internet at: http://www.sciencedirect.com, 2 pages, Jun. 2000, pp. 1414-1419.
Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, Oct. 1, 1996, pp. 1690-1697.
Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, 2002, pp. 4793-4801.
Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at: http://pubs.acs.org/cgi-bin/abstract.cgi/bcches/1997/8/i05/abs/bc9701095.html, 1 page, 1997, pp. 686-694.
Visscher, G.E., et al., "Tissue response to biodegradable injectable microcapsules", Journal of Biomaterials Applications, vol. 2, Jul. 1987, pp. 118-119.
Vlodavsky, I., et al., "Extracellular Matrix-resident Basic Fibroblast Growth Factor: Implication for the Control of Angiogenesis", J. Cell Biochem, 45(2), Abstract downloaded from the Internet at: http://www.ncbi.nlm.nih.gov/entrez/query.fcgi?cmd=Retrieve&db=PubMed, 1 page, Feb. 1991, pp. 167-176.
Wang, M., et al., "Mechanical Properties of Electrospun Silk Fibers", Macromolecules, vol. 37(18), 2004, pp. 6856-6864.
Wasielewski, "Ischamische Erkrankungen, Gefassneubildung anregen", Deutsche Apotheker Zeitung, vol. 140, No. 3, Stuttgart (DE), Jan. 20, 2000, pp. 232-233.
Wilensky, R., et al., "Direct intraarterial wall injection of microparticles via a catheter: a potential durg delivery strategy following angioplasty", American Heart Journal, 122, 1991, pp. 1136.
Witzenbichler, B., et al., "Vascular Endothelial Growth Factor-C (VEGF-C/VEGF-2) Promotes Angiogenesis in the Setting of Tissue Ischemia", AM Pathol., 153(2), Aug. 1998, pp. 381-394.
Yager, P., et al., "Silk Protein Project", www.faculty.washington.edu/yagerp/silkprojecthome.html, Aug. 23, 1997, 18 pages.
Yamamoto, N., et al., "Histologic evidence that basic fibroblast growth factor enhances the angiogenic effects of transmyocardial laser revascularization", Basic Research in Cardiology, vol. 95, No. 1, Feb. 1, 2000, pp. 55-63.
Yeo, L.Y., et al., "AC Electrospray Biomaterials Synthesis", Biomaterials, 2005, 7 pages.
Zervas, L., et al., "On Cysteine and Cystine Peptides. II. S-Acylcysteines in Peptide Synthesis", J. Am. Chem. Soc., 85(9), May 1963, pp. 1337-1341.
Zheng, W., et al., "Mechanisms of coronary angiogenesis in response to stretch: role of VEGF and TGF-beta", Am J Physiol Heart Circ Physiol., 280(2), Feb. 2001, pp. H909-H917.
Zimmermann, W., et al., "Engineered Heart Tissue for Regeneration of Diseased Hearts", Biomaterials, 25, 2004, pp. 1639-1647.
Abbott Cardiovascular Systems Inc, PCT International Search Report and Written Opinion mailed Feb. 10, 2009 for PCT Application No. PCT/US2007/023419, 17 pages.
Friedman, Paul M. et al., "Safety Data of Injectable Nonanimal Stabilized Hyaluronic Acid Gel for Soft Tissue Augmentation," Dermatologic Surgery, 2002, vol. 28, pp. 491-494.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.
Abbott Cardiovascular Systems, Non final office action dated Apr. 29, 2010 for U.S. Appl. No. 10/792,960.
Hao, X, et al., "Angiogenic effects of sequential release of VEGF-A165 and PDGF-BB with alginate hydrogels after myocardial infarction", Cardiovascular Research, 75, (2007), 178-185.
Ritter, A. B., et al., "Elastic modulus, distensibility, and compliance (capacitance)", Biomedical Engineering Principles, Chapter 4, (2005), 187-191.
Zheng, Shu, et al., "In situ crosslinkable hyaluronan hydrogels for tissue engineering", Biomaterials, Elsevier Science Publishers, vol. 25, No. 7-8, (2004), 1339-1348.
Abbott Cardiovascular Systems, Non Final Office Action dated Apr. 6, 2009 for U.S. Appl. No. 11/447,340.
Abbott Cardiovascular Systems, Non Final Office Action dated Mar. 30, 2009 for U.S. Appl. No. 10/792,960.
Abbott Cardiovascular Systems, Non Final Office Action dated Apr. 13, 2009 for U.S. Appl. No. 11/566,643.
Abbott Cardiovascular Systems, Non Final Office Action dated May 12, 2009 for U.S. Appl. No. 11/496,824.
Abbott Cardiovascular Systems, Non Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Non final office action dated Jul. 9, 2009 for U.S. Appl. No. 11/561,328.
Abbott Cardiovascular Systems, Non Final Office Action dated Apr. 29, 2009 for U.S. Appl. No. 12/013,286.
Elbert, D. L., et al., "Protein delivery from materials formed by self-selective conjugate addition reactions", Journal of Controlled Release, 76, (2001), 11-25.

(56) References Cited

OTHER PUBLICATIONS

Staatz, W D , et al., "Identification of a tetrapeptide recognition sequence for the alpha 2 beta 1 integrin in collagen", Journal of Biological Chemistry, 1991, 266(12), pp. 7363-7367.
Abbott Cardiovascular Systems, Non-Final Office Action dated Jun. 4, 2010 for U.S. Appl. No. 10/781,984.
Abbott Cardiovascular Systems, Final Office Action dated Jun. 11, 2010 for U.S. Appl. No. 11/561,328.
Abbott Cardiovascular Systems, Non final office action dated Aug. 13, 2010 for U.S. Appl. No. 11/447,340.
Abbott Cardiovascular Systems, Non-Final Office Action dated Mar. 5, 2009 for U.S. Appl. No. 11/507,860.
Abbott Cardiovascular Systems, Non final office action dated Aug. 5, 2009 for U.S. Appl. No. 11/031,608.
Abbott Cardiovascular Systems, Final office action dated Mar. 29, 2010 for U.S. Appl. No. 11/031,608.
Abbott Cardiovascular Systems, Final Office Action mailed Jul. 15, 2010, U.S. Appl. No. 11/507,860, 10 pages.
Abbott Cardiovascular Systems, Final office action mailed Sep. 27, 2010 for U.S. Appl. No. 10/792,960.
Abbott Cardiovascular Systems, Final office action mailed Sep. 27, 2010 for U.S. Appl. No. 12/016,180.
Abbott Cardiovascular Systems, Final Office Action mailed Nov. 22, 2010 for U.S. Appl. No. 10/781,984, 13 pages.
Abbott Cardiovascular Systems, Non-final Office Action mailed Nov. 24, 2010 for U.S. Appl. No. 12/013,286, 11 pages.
Abbott Cardiovascular Systems, Non-final Office Action mailed Dec. 8, 2010 for U.S. Appl. No. 11/566,643, 17 pages.
Abbott Cardiovascular Systems, Non-final Office Action mailed Dec. 17, 2010 for U.S. Appl. No. 11/933,922, 23 pages.
Abbott Cardiovascular Systems, *website for HEALON (R) OVD*, copyright 2010, accessed Dec. 15, 2010, URL: <http://abbottmedicaloptics.com/products/cataract/ovds/healon-viscoelastic>, (2010), 2 pages.
Abbott Cardiovascular Systems, *Product Information Sheet for HEALON (R), from Abbott Medical Optics*, (2005), 1 page.
Abbott Cardiovascular Systems, Japanese Office Action dated Dec. 8, 2010 for Japanese Patent App No. 2006-509975., 6 pages.
Abbott Cardiovascular Systems, Non final office action mailed Feb. 8, 2011 for U.S. Appl. No. 10/792,960.
Bull, S. , et al., "Self-Assembled Peptide Amphiphile Nanofibers Conjugated to MRI Contrast Agents", *Nano Letters*, vol. 5, No. 1, (Jan. 2005), 4 pages.
Csonka, E. , et al., "Interspecific Interaction of Aortic Endothelial and Smooth Muscle Cells", *Acta Morphologica Hungarica*, vol. 35, No. 1-2, (1987), 31-35.
Gries, D. P., et al., "Vascular gene delivery of anticoagulants by transplantation of retrovirally-transduced endothelial progenitor cells", *Cardiovascular Research*, vol. 58, (2003), 469-477.
Hartgerink, J. D., et al., "Peptide-amphiphile nanofibers: A versatile scaffold for the preparation of self-assembling materials", *PNAS*, vol. 99, No. 8, (Apr. 16, 2002), 5133-5138.
Hartgerink, J. D., et al., "Self-Assembly and Mineralization of Peptide-Amphiphile Nanofibers", *Science*, vol. 294, (Nov. 23, 2001), 1684-1688.
Haynesworth, Stephen E., et al., "Platelet Effects on Human Mesenchymal Stem Cells", *Abstract, presented at Orthopedic Research Society 48th Annual Meeting*, Dallas, TX, (Feb. 10-13, 2010), 2 pages.
Li, B. , et al., "VEGF and PlGF promote adult vasculogenesis by enhancing EPC recruitment and vessel formation at the site of tumor neovascularization", *The FASEB Journal*, vol. 20, (2006), 1495-1497.
Seeger, J. M., et al., "Improved in vivo endothelization of prosthetic grafts by surface modification with fibronectin", *J Vasc Surg*, vol. 8, No. 4, (Oct. 1988), 476-82 (Abstract only).
Urbich, C. , et al., "Endothelial Progenitor Cells: Characterization and Role in Vascular Biology", *Circulation Research*, vol. 95, (2004), 343-353.

Abbott Cardiovascular Systems, Non final office action mailed Jun. 7, 2011 for U.S. Appl. No. 11/447,340.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Final Office Action mailed Apr. 15, 2011 for U.S. Appl. No. 10/414,602.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Chung, Y. , et al., "Sol-gel transition temperature of PLGA-g-PEG aqueous solutions", Biomacromolecules, vol. 3, No. 3, (May 2002), 511-516.
Abbott Cardiovascular Systems, Final Office Action mailed Dec. 13, 2011 for U.S. Appl. No. 12/963,397.
Abbott Cardiovascular Systems, Non-Final Office Action mailed Jan. 30, 2012 for U.S. Appl. No. 10/781,984.
Abbott Cardiovascular Systems, Final Office Action mailed Feb. 8, 2012 for Japanese Application No. 2006-509975, 6 pages.
Abbott Cardiovascular Systems, Non-Final Office Action mailed Feb. 15, 2012 for U.S. Appl. No. 12/114,717.
Abbott Cardiovascular Systems, Final Office Action mailed Apr. 4, 2012 for U.S. Appl. No. 10/792,960.
Abbott Cardiovascular Systems, European Office Action mailed Apr. 11, 2012 for EP App No. 12155231.9, 9 pages.
Abbott Cardiovascular Systems, European Office Action mailed Apr. 10, 2012 for EP App No. 07810637.4, 6 pages.
Abbott Cardiovascular Systems, Final Office Action mailed May 9, 2012 for U.S. Appl. No. 11/110,223.
Abbott Cardiovascular Systems, European Search report mailed Apr. 18, 2012 for EP Application No. 12151788.2, 6 pages.
Abbott Cardiovascular Systems, Non-final Office Action mailed Jun. 22, 2012 for U.S. Appl. No. 12/963,397.
Abbott Cardiovascular Systems, Restriction requirement mailed Jul. 3, 2012 for U.S. Appl. No. 13/4722,324.
Abbott Cardiovascular Systems, Non-final Office Action mailed Jun. 26, 2012 for U.S. Appl. No. 12/632,612.
Abbott Cardiovascular Systems, Japanese Office Action dated Jun. 11, 2012 for JP Appln. No. 2010-162711.
Abbott Cardiovascular Systems, Non-final Office Action mailed Aug. 28, 2012 for U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Non-Final Office Action dated Sep. 11, 2012 for U.S. Appl. No. 10/792,960.
Abbott Cardiovascular Systems, Japanese office action dated Aug. 20, 2012 for JP Appln. No. 2009-537153.
Abbott Cardiovascular Systems, Non-Final Office Action dated Oct. 3, 2012 for U.S. Appl. No. 12/756,119.
Abbott Cardiovascular Systems, et al., Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Abbott Cardiovascular Systems, Japanese Office Action dated Nov. 19, 2012 for JP Appln. No. 2009-539265.
Abbott Cardiovascular Systems, Japanese Office Action mailed Dec. 17, 2012 for Appln. No. JP 2009-546553.
Abbott Cardiovascular Systems, Examination Report dated Feb. 20, 2013 for European Appln. No. 12151788.2.
Davis, M E., et al., "Injectable Self-Assembling Peptide Nanofibers Create Intramyocardial Microenvironments for Endothelial Cells", Circulation, 111, (2005), 442-450.
Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.
Mogan, L. , "Rationale of platelet gel to augment adaptive remodeling of the injured heart", J Extra Corpor Technol, 36(2), (Jun. 2004), 191-196.

(56) References Cited

OTHER PUBLICATIONS

Zheng, W., "Mechanisms of coronary angiogenesis in response to stretch; role of VEGF and TGF-Beta", Am J Physiol Heart Circ Physiol 280(2), (Feb. 2001), H909-H917.
Abbott Cardiovascular Systems, Final Office Action mailed Oct. 21, 2011 for U.S. Appl. No. 10/781,984.
Abbott Cardiovascular Systems, Final Office Action mailed Jan. 5, 2012 for U.S. Appl. No. 11/361,920.
Abbott Cardiovascular Systems, Office Action mailed Jan. 17, 2012 for European Patent Application 08727952.7, 6 pages.
Abbott Cardiovascular Systems, Non-Final Office Action mailed Aug. 31, 2011 for U.S. Appl. No. 11/110,223.
Abbott Cardiovascular Systems, Non final office action mailed Nov. 8, 2011 for U.S. Appl. No. 10/792,960.
Abbott Cardiovascular Systems, Final office action mailed Jul. 18, 2011 for U.S. Appl. No. 11/566,643.
Abbott Cardiovascular Systems, Final office action dated Jan. 18, 2013 for U.S. Appl. No. 12/963,397.
Abbott Cardiovascular Systems, Japanese office action dated Oct. 9, 2012 for JP Appln. No. 2009-514330.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Final office action mailed Apr. 22, 2013 for U.S. Appl. No. 10/792,960.
Abbott Cardiovascular Systems, Japanese office action mailed Mar. 25, 2013 for JP 2009-539265.
Abbott Cardiovascular Systems, Non final office action mailed May 31, 2013 for U.S. Appl. No. 13/559,438.
Abbot Cardiovascular Systems, Non-final Office Action mailed Dec. 4, 2013 for U.S. Appl. No. 11/507,860.
Abbot Cardiovascular Systems, Non-final Office Action mailed Dec. 4, 2013 for U.S. Appl. No. 11/561,328.
Abbott Cardiovascular Systems, Notice of Allowance mailed Sep. 30, 2013 for U.S. Appl. No. 13/559,423.
Abbott Cardiovascular Systems, Non final office action dated Aug. 20, 2013 for U.S. Appl. No. 12/114,717.
Abbott Cardiovascular Systems, Non-Final Office Action mailed Oct. 23, 2013 for U.S. Appl. No. 11/110,223.
Chemcas.org, MSDS 4-amino-2,2,6,6-tetramethlypiperidine-1-oxyl (4-amino-TEMPO) CAS No. 14691-88-4 at www.chemcas.org/drug/analytical/cas/14691-88-4-asp, (Sep. 2, 1997), 5.

\* cited by examiner

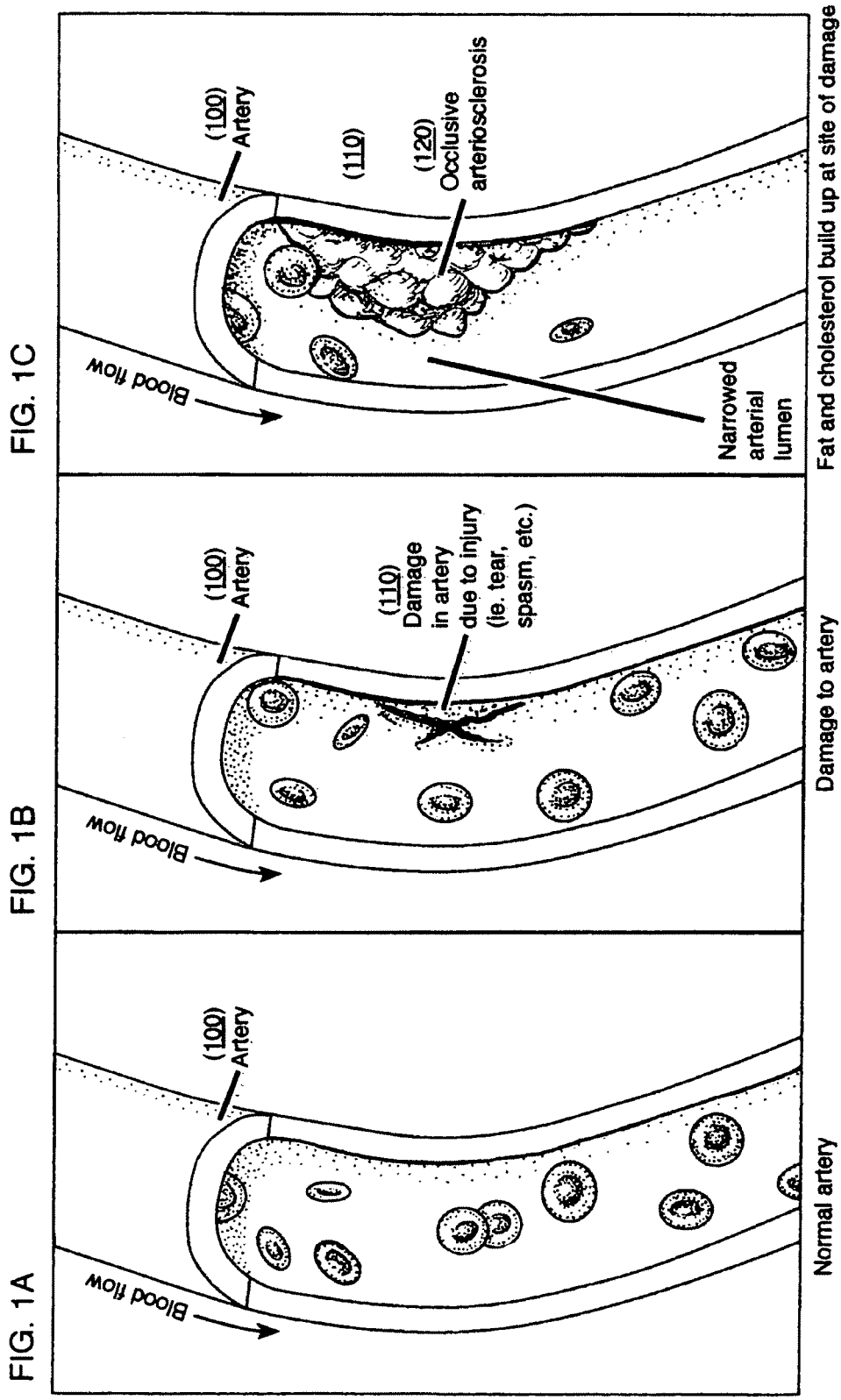

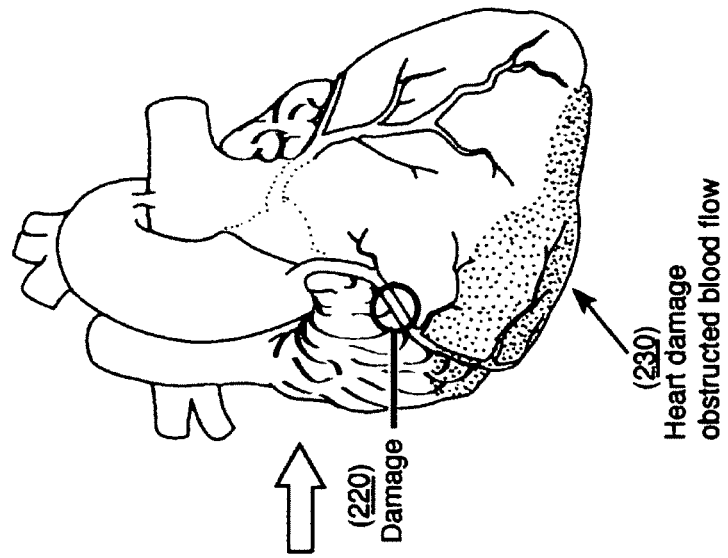
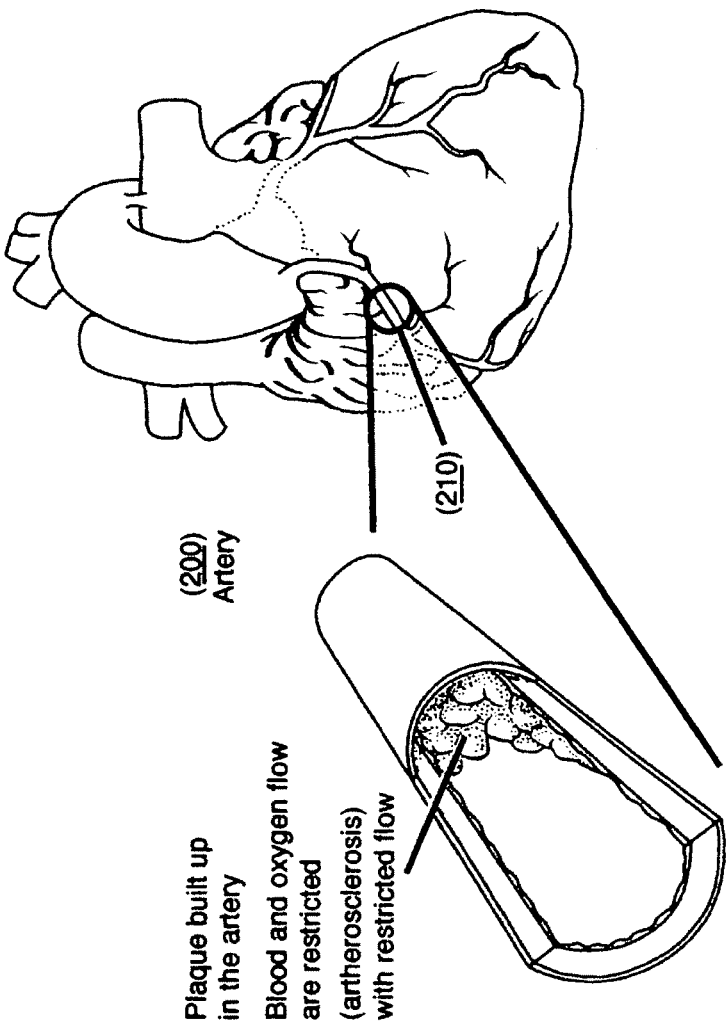

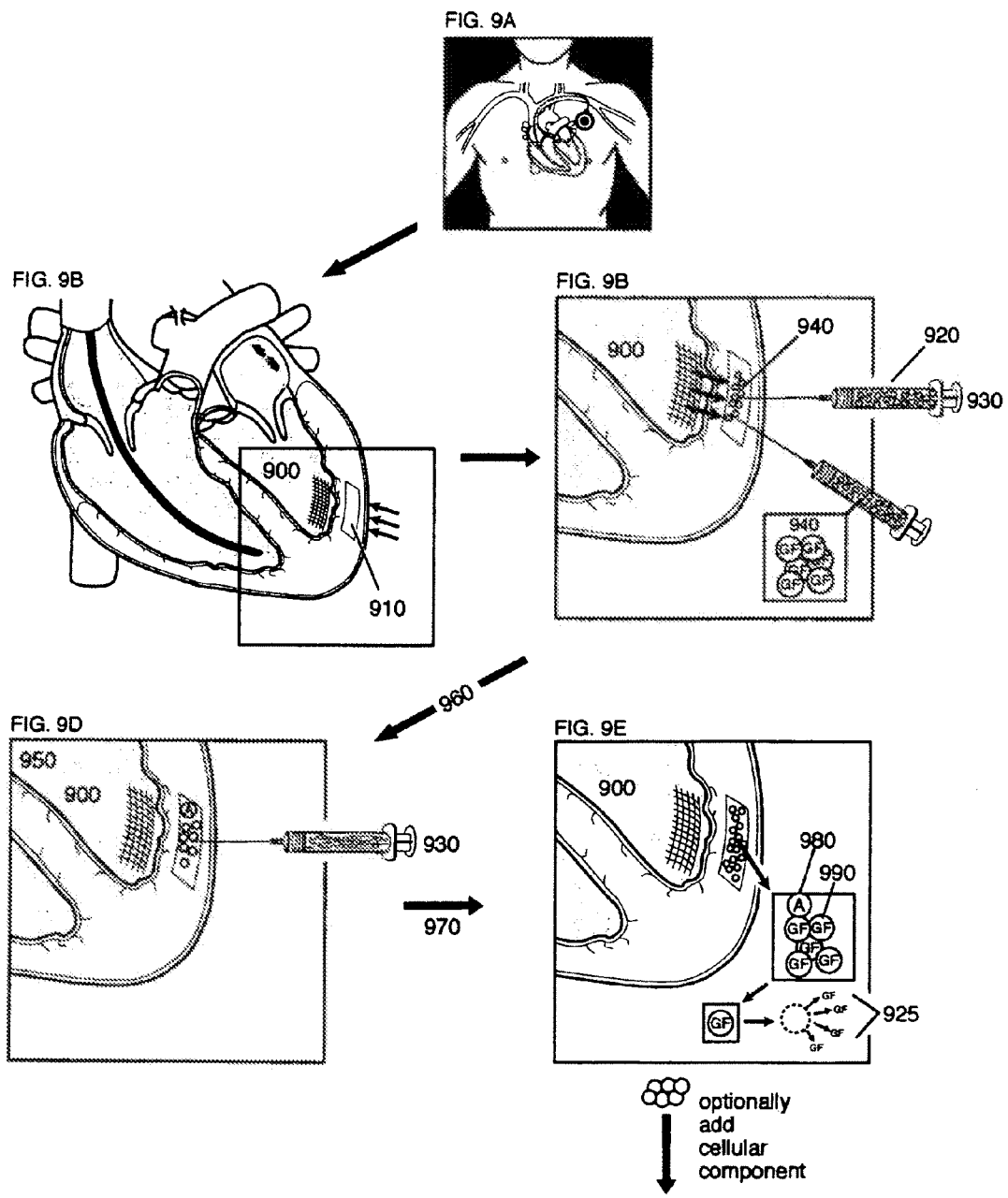

METHODS AND COMPOSITIONS TO TREAT MYOCARDIAL CONDITIONS

CROSS REFERENCE TO RELATED APPLICATIONS

This application is a divisional of U.S. patent application Ser. No. 10/802,955, filed Mar. 16, 2004, U.S. Pat. No. 7,294,334 which is a continuation-in-part of presently U.S. patent application Ser. No. 10/414,602, filed Apr. 15, 2003, U.S. Pat. No. 8,383,158.

FIELD OF THE INVENTION

The treatment of myocardial infarction, and more particularly, in one embodiment, to the reinforcement of the infarct regional wall of a heart chamber using targeted cell delivery and/or the inhibition of the thinning of the infarct regional wall of a heart chamber using cell delivery in combination with other therapies such as electrostimulation. In further embodiments, to combine reinforcement of the infarct regional wall and/or cellular replacement with stimulating the heart using a pulsing and/or pacing device. In addition, this invention also pertains to apparatus and methods for electrostimulation of the heart including cardiac pacing with an artificial pacemaker to prevent or correct the negative effects of remodeling. In particular, the invention relates to methods for stimulating the heart in order to effect reversal of myocardial remodeling and provide structural support to the infarct region.

BACKGROUND OF THE INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. Blood flow can be further decreased by additional events such as changes in circulation that lead to hypoperfusion, vasospasm or thrombosis.

Myocardial infarction accounts for approximately 20% of all deaths. It is a major cause of sudden death in adults.

Myocardial Infarction (MI) is one form of heart disease that often results from the sudden lack of supply of oxygen and other nutrients. The lack of blood supply is a result of closure of the coronary artery that nourishes the particular part of the heart muscle. The cause of this event is generally caused by arteriosclerosis "hardening of the arteries" in coronary vessels.

Formerly, it was believed that an MI was caused from a slow procession of closure from for example 95% then to 100% but an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Even though relatively effective systemic drugs exist to treat MI such as ACE-inhibitors and Beta-blockers, a significant portion of the population that experiences a major MI ultimately develops heart failure. An important component in the progression to heart failure is remodeling of the heart due to mechanical forces resulting in uneven stress and strain distribution in the left ventricle. Once an MI occurs remodeling of the heart begins. The principal components of the remodeling event include myocyte death, edema and inflammation, followed by fibroblast infiltration and collagen deposition, and finally scar formation. The principle component of the scar is collagen. Since mature myocytes of an adult are not regenerated the infarct region experiences significant thinning. Myocyte loss is the major etiologic factor of wall thinning and chamber dilation that may ultimately lead to progression of cardiac myopathy. Myocyte death can and does occur. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

FIG. 1A-1C illustrates blood flow by longitudinal cross sectioning of the artery. FIG. 1A illustrates a normal unobstructed artery. FIG. 1B illustrates artery damage due to a tear or spasm. This figure illustrates a minor insult to the interior wall. FIG. 1C illustrates an artery with plaque build-up that reduces the blood flow demonstrated by the blocked blood cell above the atherosclerotic mass. Fat and cholesterol build up at the site of damage. This mass can be detected by methods currently available such as an, ECG, SPECT, MRI, and angiogram.

FIG. 2A-2B illustrate the progression of heart damage once the build-up of plaque induces an infarct to occur. The most common pathogenesis of this disease is occlusive intracoronary thrombus where a thrombus is covering an ulcerated stenotic plaque. This causes approximately 90% of transmural acute myocardial infarctions. Other possible triggers of an MI are vasospasms with or without coronary atherosclerosis and possible association with platelet aggregation. Another possible trigger is embolisms from left-sided mural thrombosis, vegetative endocarditis or a paradoxic embolism from the right side of the heart through a patent foramen ovale. FIG. 2A illustrates a site where blockage and restricted blood flow can occur from any of the indicated causes. FIG. 2B illustrates the extensive damage to the left ventricle that can be a result of the lack of oxygen and nutrient flow carried by the blood to the inferior region left ventricle of the heart. This area will likely undergo remodeling and eventually a scar will form and a non-functional (an area that does not contract) area will exist.

Significant atherosclerotic build-up can reduce the arterial lumen and reduce blood flow. Build-up is capable of rupturing resulting in a total or partial occlusion of the artery. Complete coronary occlusion will lead to an acute MI. Thus the T-cells, platelets, fibrin and multiple other factors and cells are blocked from progression through the blood stream and the result is an inadequate vascular supply as seen. This leads to myocyte death. Myocyte death, in addition to fibrosis in the form of collagen deposition, can lead to a compromised left ventricle and overload on the remaining myocytes. This process is further complicated by compensation of the remaining myocytes that hypertrophy (enlarge). This can cause the left ventricle to enlarge and if the cycle continues can result in eventual heart failure.

The morphological appearance of the infarcted heart tissue post MI can vary. A transmural infarct involves the entire thickness of the left ventricular wall from the endocardium to the epicardium. It may extend into the anterior free wall and the posterior free wall. This damage may include extensions into the right ventricular wall. A subendocardial infarct may have multiple focal regions and necrosis area may be confined to the inner one-third to one-half of the left ventricular wall.

The evolutionary changes in a subendocardial infarct do not evolve the same as in a transmural MI.

Over time post-MI morphological changes occur. The gross morphological changes that occur over approximately a 7-week period are pallor of the myocardium that leads to some hyperemia then yellowing central to the damaged region. At approximately 15 days, the area is mostly yellow with soft vascular margins. This area eventually turns white from fibrosis. On a microscopic level, the initial examination reveals wavy myocardial fibers. Coagulation and necrosis with loss of cross striations occur followed by contraction bands, edema, hemorrhage, and neutrophilic infiltrate. Within 24-72 hours there is total loss of nuclei and striations and heavy neutrophilic infiltrate. Then macrophage and mononuclear infiltration begin resulting in a fibrovascular response. Once this fibrovascular response occurs then prominent granulation of the tissue follows. This ultimately leads to fibrosis and a scar is formed by about 7 weeks post MI.

FIG. 3A-3B illustrate the occlusion of an artery that may lead to an MI. FIG. 3A illustrates the cross-section of a normal coronary artery with unobstructed lumen 301. The normal arterial wall 302 is made up of an intima layer 303, a media layer 304, and an adventitia layer 305. Within the arterial lumen, the intima is in direct contact with the flow of blood. This region is mostly made up of endothelial cells. The media layer is mostly smooth muscle cells and extracellular matrix proteins. Finally, the adventitia layer is primarily made up of collagen, nerves, blood vessels and lymph vessels. FIG. 3B illustrates a coronary artery with atherosclerosis. In this example, this artery is about 50 percent occluded (only 50 percent of the arterial lumen is free of obstruction). Thus, the obstructed artery may lead to damage observed in a ventricle of an MI subject.

After an MI has occurred, three layers of tissue can be distinguished. The infarct region has (1) the region of significant necrosis/apoptosis tissue (2) the border zone that consists of a large concentration of apoptotic and necrotic tissue as well as viable tissue and (3) the unaffected region that consists of mainly viable tissue. In the border zone the cells exist in an oxygen-deprived state due to the damage from the MI.

FIG. 3C-3J illustrate the details of a post-MI remodeling of the ventricle. The progression of heart failure after an MI is a result of the remodeling of the heart after the infarct. The remodeling process causes infarcted region of the heart to stretch and become thinner causing the left ventricular diameter to increase. As the heart continues to remodel, the stresses on the heart increase. FIG. 3C, on a cellular level, a normal myocardium is illustrated. FIG. 3C illustrates the cross striations 306 and central nucle 307 of a healthy myocyte population.

FIG. 3D-3J depict the progression of the remodeling of the ventricle post MI. FIG. 3D illustrates an early acute MI. Here, there are prominent pink contraction bands that are indicated by reference number 308. FIG. 3E illustrates the increasing loss of striations and some contraction bands. The nuclei in this illustration are incurring karyolysis, i.e., a stage of cell death that involves fragmentation of a cell nucleus; the nucleus breaks down into small dark beads of damaged chromatin 309. In addition, the neutrophils are infiltrating the damaged myocardial region. FIG. 3F illustrates an acute MI. The loss of nuclei and loss of cross striations are evident. There is extensive hemorrhaging on the infarct border 310. FIG. 3G illustrates the prominent necrosis and hemorrhaging 310, as well as the neutrophilic infiltrate 311. Subsequently, a yellowish center is formed within the damaged area with necrosis and inflammation surrounded by the hyperemic border. After 3-5 days post-MI, the necrosis and inflammation are extensive. There is a possibility of rupture at this point. FIG. 3H illustrates approximately one week after the MI with capillaries, fibroblasts and macrophages filled with haemosiderin (haemosiderin is a long-term reserve (storage form) of iron in tissues) 312. In two to three weeks granulation is the most prominent feature observed. FIG. 3I illustrates extensive collagen deposition 313 seen after a couple of weeks. Collagenous scarring occurs in subendocardial locations in remote myocardial infarct regions. FIG. 3J illustrates the myocytes 314 after several weeks of healing post MI. They are hypertrophied with large dark nuclei 315 and interstitial fibrosis 316. These enlarged cells contribute to the enlarged left ventricle.

A complication of an MI is an aneurysm that looks like a bulge in the left ventricular wall. The aneurysm is made up of non-functional tissue that is unable to contract. Therefore, the ejection and stroke volume of the heart are reduced. Additionally, parts of this mass can form a mural thrombus that can break off and embolize to the systemic circulation.

Heart Stimulation and the Use of Prostaglandins

The body essentially produces two types of prostaglandins; "good" prostaglandins and "bad" prostaglandins. Prostaglandins are hormone-like substances that regulate many body processes, such as blood clotting. "Good" prostaglandins (PG1 and PG3) regulate heart function, improve blood flow and prevent platelets from sticking together. A diet rich in Omega-3 fatty acids leads to the production of PG3, which is beneficial.

Prostaglandins are compounds that are produced via the metabolism of fats in our diets. These compounds are simplistically categorized as either "good" or "bad." The good prostaglandins are beneficial and constructive to the body while the bad ones, if produced on a continual basis, can be destructive.

Prostaglandins are hormone-like substances, which have wide and significant effects in regulating many vital life processes. The importance of the role of these compounds has been appreciated only in the last decade. One type of prostaglandin E prevents platelets—a blood constituent—from clotting. This discovery may be applied clinically against heart attacks and strokes caused by clots. These prostaglandins, by inhibiting the secretion of gastric acid in the stomach, may also by useful in the treatment of gastric ulcer.

The E type prostaglandin, a powerful dilator of blood vessels, has been found in animal experiments to reduce high blood pressure—another cause of heart attacks and stroke. Such blood pressure reduction appears to be the result of accelerated water excretion and inhibition of sodium retention.

In one study, prostaglandin E2 (PGE2) was used to maintain patency of the ductus arteriosus in four neonates with cyanotic congenital heart disease due to obstructive right heart malformations. PGE2 was infused prior to surgery, and in three patients, during surgery until a satisfactory aortopulmonary shunt was established. PGE2 produced consistently an immediate and persistent rise in arterial oxygen saturation, which could be ascribed to dilation of the ductus arteriosus. No major side effects occurred, except for pyrexia in two infants. All patients recovered well from surgery. This treatment was proposed as a treatment for preparation for surgery in any infant with congenital heart defects and ductus-dependent pulmonary blood flow. The same treatment may be useful preoperatively in patients with aortic interruption who also depend on continued patency of the ductus for blood supply to the lower half of the body Pacing and Pulse Generators (PG)

An implantable pacemaker pulse generator is a device that has a power supply and electronic circuits that produce a periodic electrical pulse to stimulate the heart. This device is used as a substitute for the heart's intrinsic pacing system to correct both intermittent and continuous cardiac rhythm disorders. This device includes triggered, inhibited, and asynchronous devices implanted in the human body.

Electrical stimulation of the heart underlies cardiac pacing and defibrillation. The "bidomain model" describes the anisotropic electrical properties of cardiac tissue. In particular, this model predicts mechanisms by which applied electric fields change the transmembrane potential of the myocardial cells. During unipolar stimulation, the bidomain model can explain "make" and "break" stimulation. Furthermore, it elucidates the cause of the "dip" in the anodal strength-interval curve, and predicts the initiation of novel quatrefoil reentry patterns. These results are beginning to shed light on the mechanisms of arrhythmia induction and defibrillation.

What is needed is to prevent thinning of the infarct region, replace dead cells with viable cells stimulation of the removal/replacement of the tissue affected by myocardial infarction to enhance the ECM production.

SUMMARY

Embodiments herein relate to methods, apparati and compositions for reversing ventricular remodeling using electro-stimulatory therapy in combination with other methods such as structural reinforcement of the area to prevent remodeling and strengthen an infarct region. By pacing sites in proximity to the infarct with appropriately timed pacing pulses, the infarct region is pre-excited in a manner that lessens the mechanical stress to which it is subjected, thus reducing the stimulus for adverse remodeling. Reducing the wall stress of the infarct region also decreases the probability of an arrhythmia arising from the region. Another advantage obtained with resynchronizing the ventricular contraction by pre-exciting a weakened infarct region is the creation of hemodynamically more efficient contraction.

In one embodiment, the ventricular stimulatory pulse or pulses may be delivered in accordance with a programmed bradycardia pacing mode in response to sensed cardiac activity and lapsed time intervals. In another embodiment, a stimulating/sensing electrode is disposed in the ventricle at a selected site in proximity to a stressed region. Pacing that pre-excites the ventricle at this site results in the stressed region being excited before other regions of the ventricular myocardium as the wave of excitation spreads from the paced site. Other embodiments involve multi-site pacing in which multiple stimulating/sensing electrodes are disposed in the ventricles. Pacing the ventricles during a cardiac cycle then involves outputting pulses to the electrodes in a specified sequence. In one embodiment, the pulse output sequence may be specified such that a stressed region of the ventricular myocardium is excited before other regions as the wave of excitation spreads from the multiple pacing sites.

In one embodiment, a composition is described that is capable of replacing the myocardial cells and may provide reinforcement to the ventricle in addition to the pacing methods describe previously. The replacement cells consist of cells that do not trigger an immune response often seen in graft rejection. In another embodiment, a method is described to increase the compliance of a ventricle by preventing thinning of the infarct region and eliminating the cellular debris created by the infarct. A cellular bolus may be advanced through a delivery device to the infarct zone for reinforcement. In one embodiment, the cellular therapy may be combined with stimulatory therapies created by electrical and/or chemical stimuli. In other embodiments, a treatment agent is delivered via multiple small volumes to the region. These delivery methods may use imaging of the ventricular wall to guide the deposition of the treatment agent to the site of the infarct zone such as deposition of the gel-forming agents.

In one embodiment, the cells delivered to the infarct region may comprise an immunotolerant or non-antigenic cell line such as, but not limited to, α-1,3-galactosyltransferase (GGTA1) knockout swine cells. In other embodiments, treatment agents may also be used to induce angiogenesis.

In another embodiment, one or more components may be delivered by microparticles harboring the component and/or therapeutic agents or growth factors. Cells that infiltrate the infarct region may be stimulated to proliferate. In other embodiments, cellular treatments may be combined with a peri-infarct treatment such as electrical stimuli by leads in contact with the infarct region that encourages new growth in the infarct area. This modulation of tissue response in the infarct zone is suitable for reinforcing the region and preventing the thinning process of the ventricular wall.

Other embodiments directed to the prevention of thinning of the infarct region of the ventricle wall are included. Treatment agents that are capable of cross-linking the existing collagen in the infarct region are described. The cross-linked collagen would form a structurally reinforcing wall in the infarct region to bulk-up the infarct zone and reduce the effects of thinning. This may be combined with the cellular replacement and/or electro-stimulatory therapy.

In another embodiment, a method includes multi-component treatments of the infarct zone. One multi-component method includes the formation of a scaffold to facilitate the attachment of cells and to deliver growth factors and other treatment agents. In addition, the in-growth of new capillaries is encouraged by the sustained release of angiogenic factors by the microparticles that form the scaffold. The treatment agents may be released for up to two months period. This technique would offer maximum benefit for the regeneration of viable tissue. These treatments may be used prior to, in conjunction with or after electro-stimulatory therapy.

In another embodiment, a different multi-component treatment of the infarct zone introduces a scaffold system that provides a matrix to facilitate cell growth and attenuate the remodeling event post-MI. In addition, the treatment may include a perfluorinated compound that enhances the re-oxygenation of the tissue. These methods may also be combined with electro-stimulatory therapies in order to enhance the recovery period of a subject (e.g., a subject with heart disease).

In one embodiment, the treatments proposed may occur at any time after a heart defect such as but not limited to an infarction or heart failure. In another embodiment, the treatments proposed may occur within seven weeks of an MI event (or prior to myocyte replacement). In another embodiment, the treatments proposed may occur within two weeks of an MI event.

In a further embodiment, a kit is disclosed. One example of such a kit is a kit including an injectable cell composition that may be introduced to the infarct region directly. Optionally, a kit may contain a pace generating device or other stimulatory device.

BRIEF DESCRIPTION OF THE DRAWINGS

The methods and compositions are illustrated by way of example, and not limitation, in the figure of the accompanying drawings in which:

FIG. 1A illustrates a longitudinally sectioned healthy artery and blood flow therein.

FIG. 1B illustrates a longitudinally sectioned damaged artery due to a tear or a spasm.

FIG. 1C illustrates a longitudinally sectioned occluded artery due to fat and cholesterol build up.

FIG. 2A illustrates plaque build up in an artery that may result in restriction of blood and oxygen flow to the heart.

FIG. 2B illustrates the damage to the heart as a result of the plaque build-up in an artery that lead to an MI.

FIG. 9 illustrates introduction and action of the methods illustrated in the flowchart of FIG. 7 in an infarct region.

DEFINITIONS

Figure 3A:
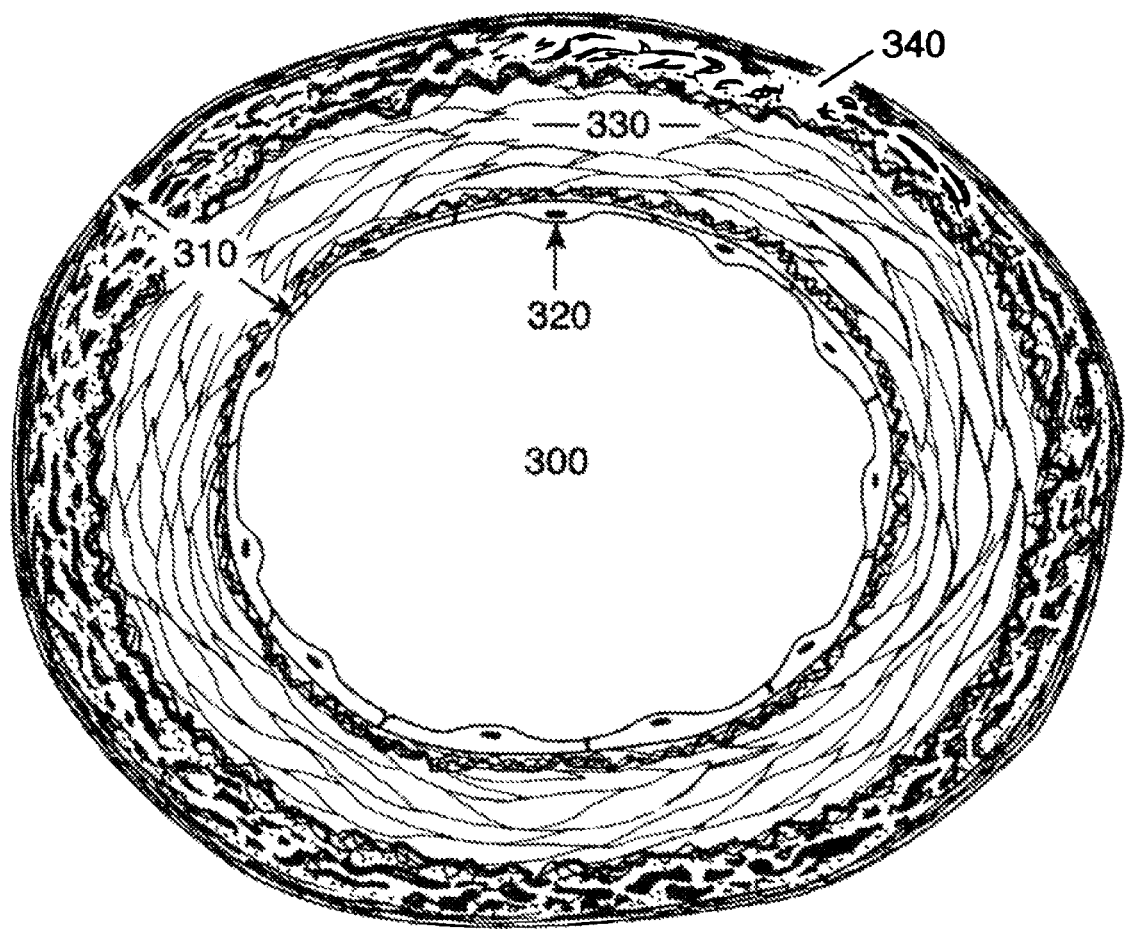
FIG. 3A illustrates a normal artery.
Figure 3B:
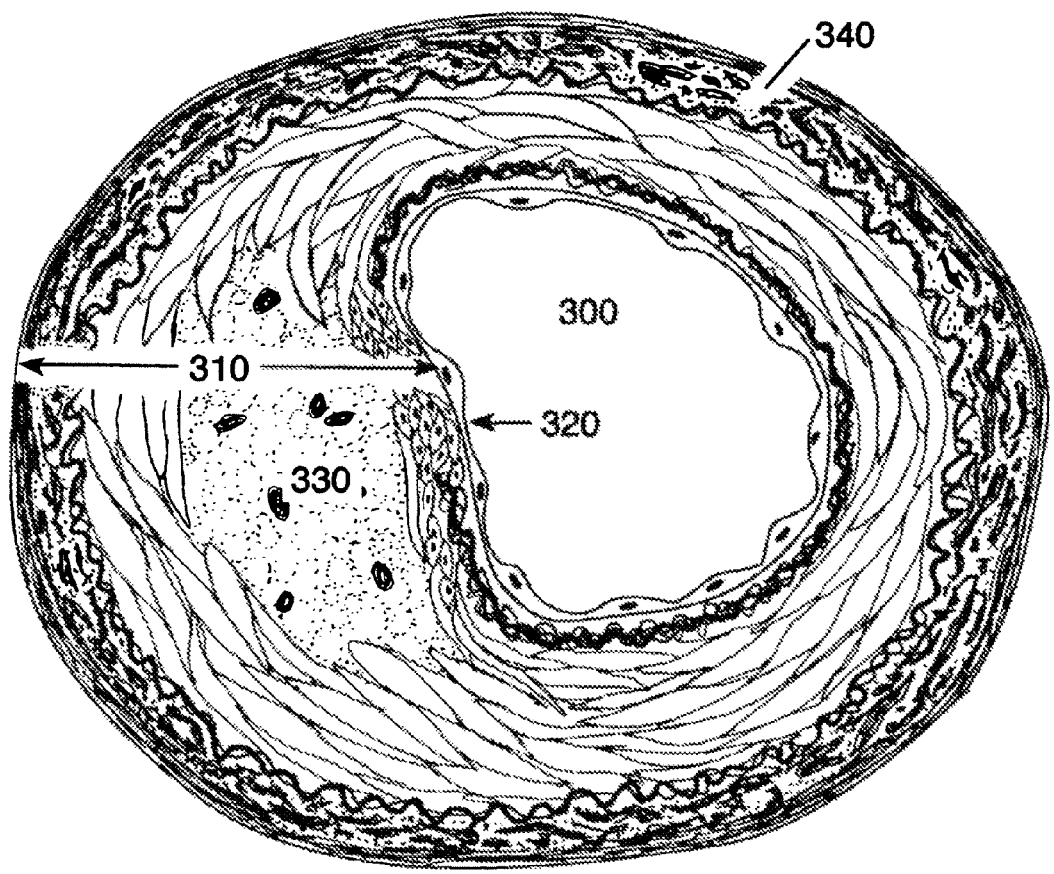
FIG. 3B illustrates an artery with arteriosclerosis (50 percent blockage) that may lead to an MI.
Figure 3C:
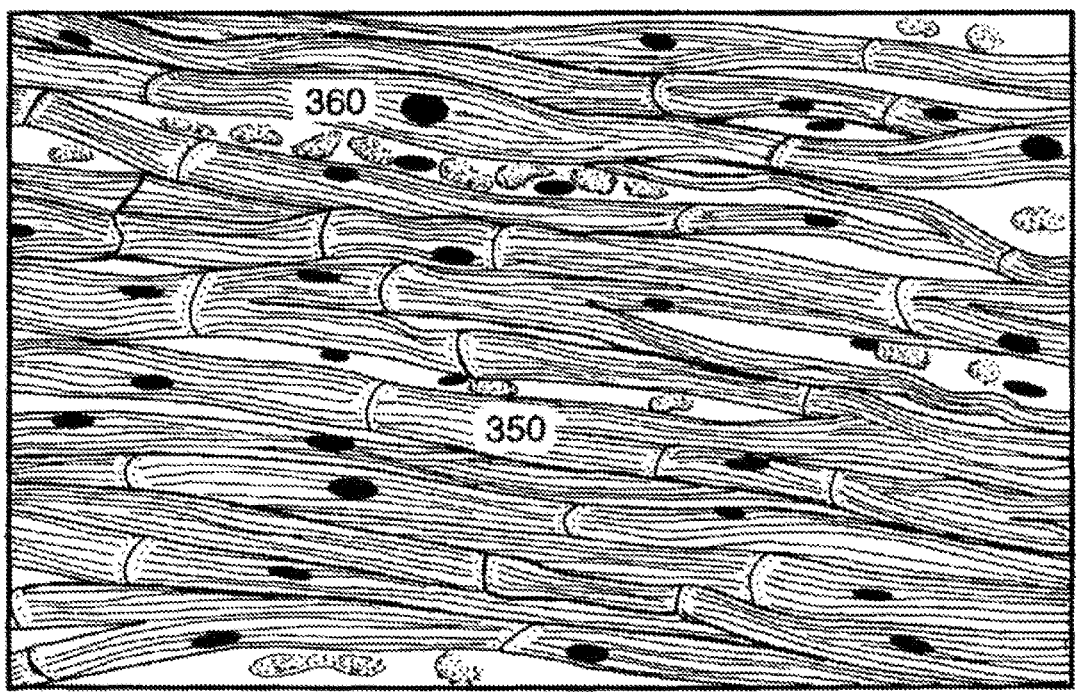
FIG. 3C illustrates normal myocardium.
Figure 3D:
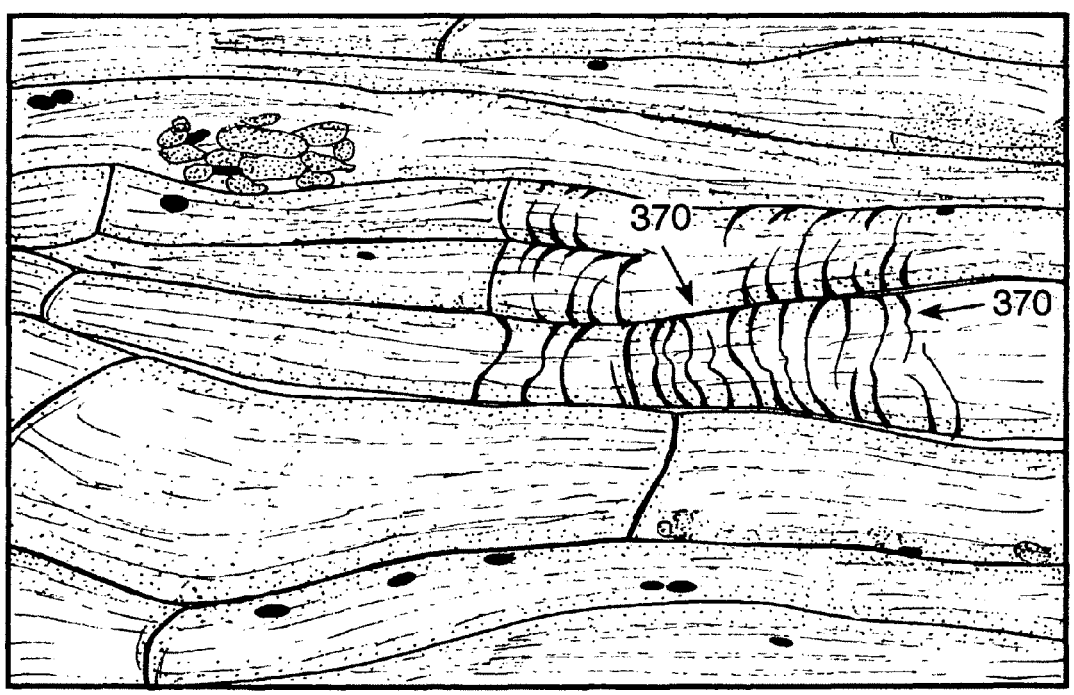
FIG. 3D illustrates an example of myocardium of an early acute myocardial infarction.
Figure 3E:
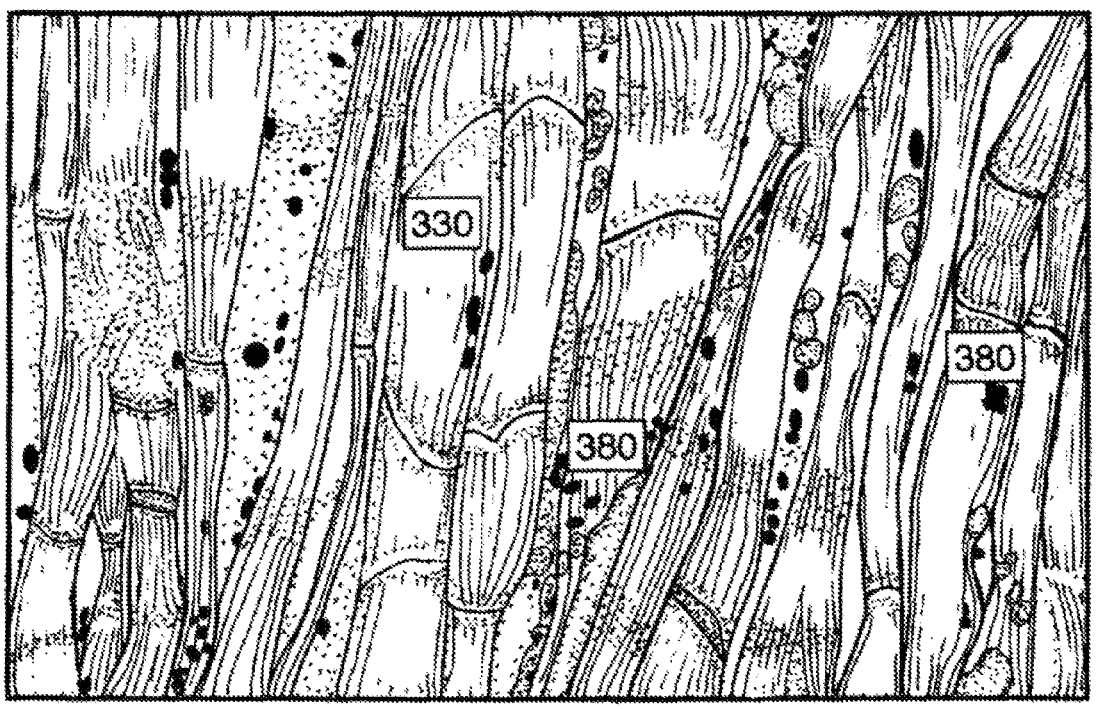
FIG. 3E illustrates an example of myocardium of an early myocardial infarction whereby a myocardium demonstrates increasing loss of cross striations.
Figure 3F:
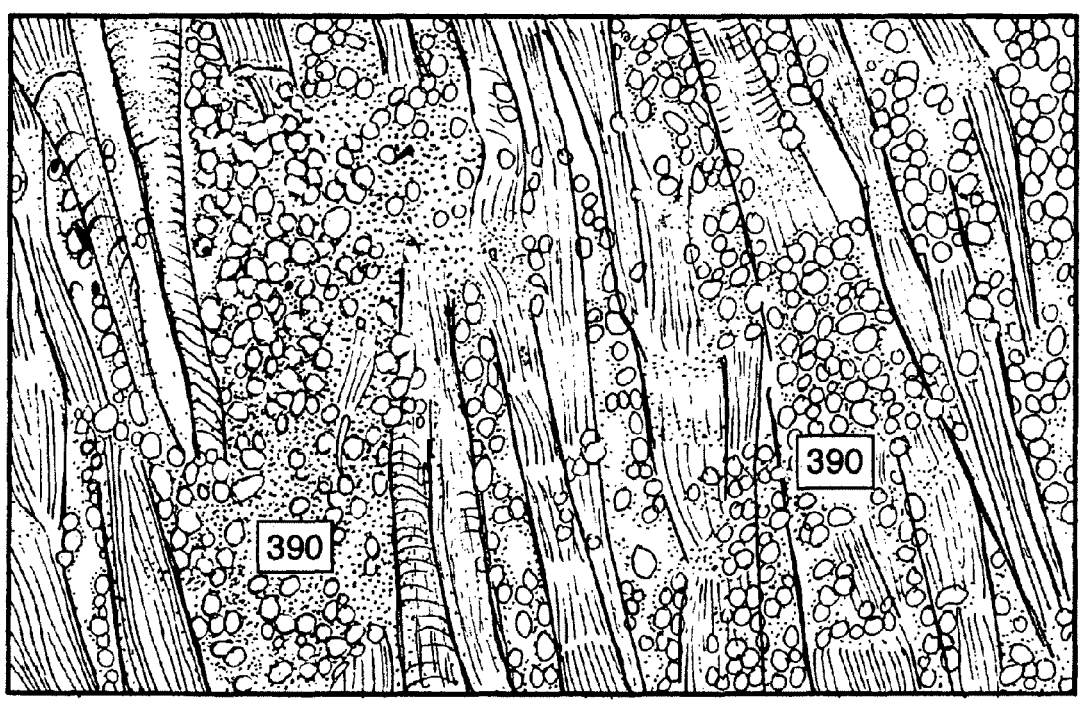
FIG. 3F illustrates an example of myocardium of an acute myocardial infarction and the loss of striations and the nuclei.
Figure 3G:
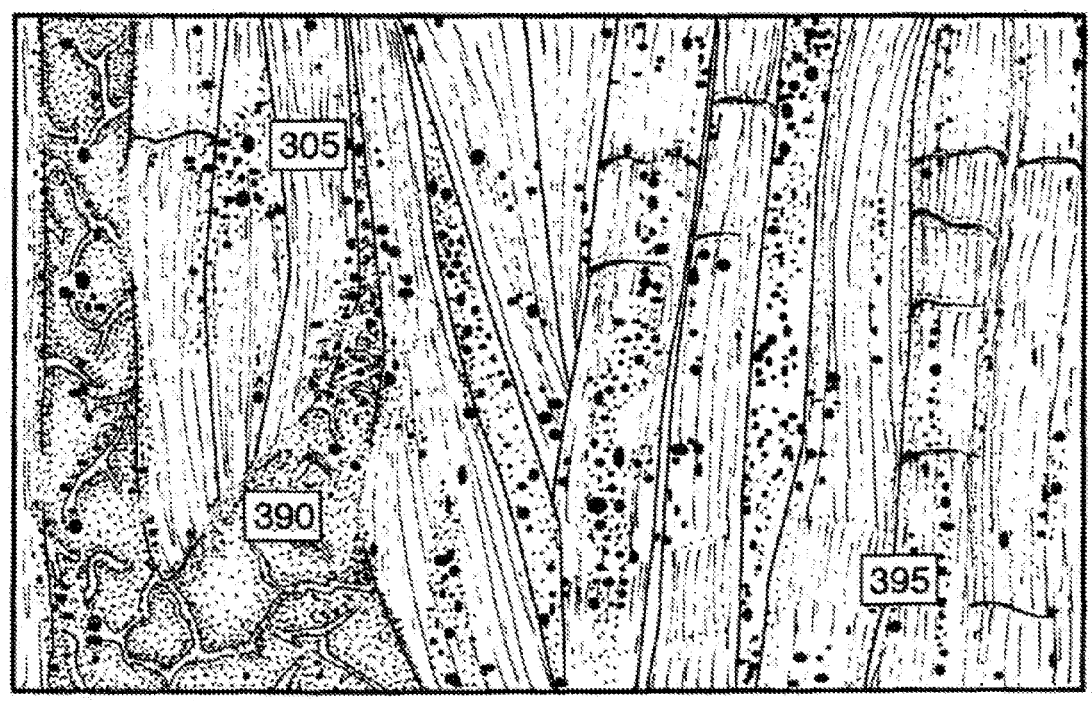
FIG. 3G illustrates an example of myocardium of an acute myocardial infarction resulting in neutrophilic infiltration and necrosis.
Figure 3H:
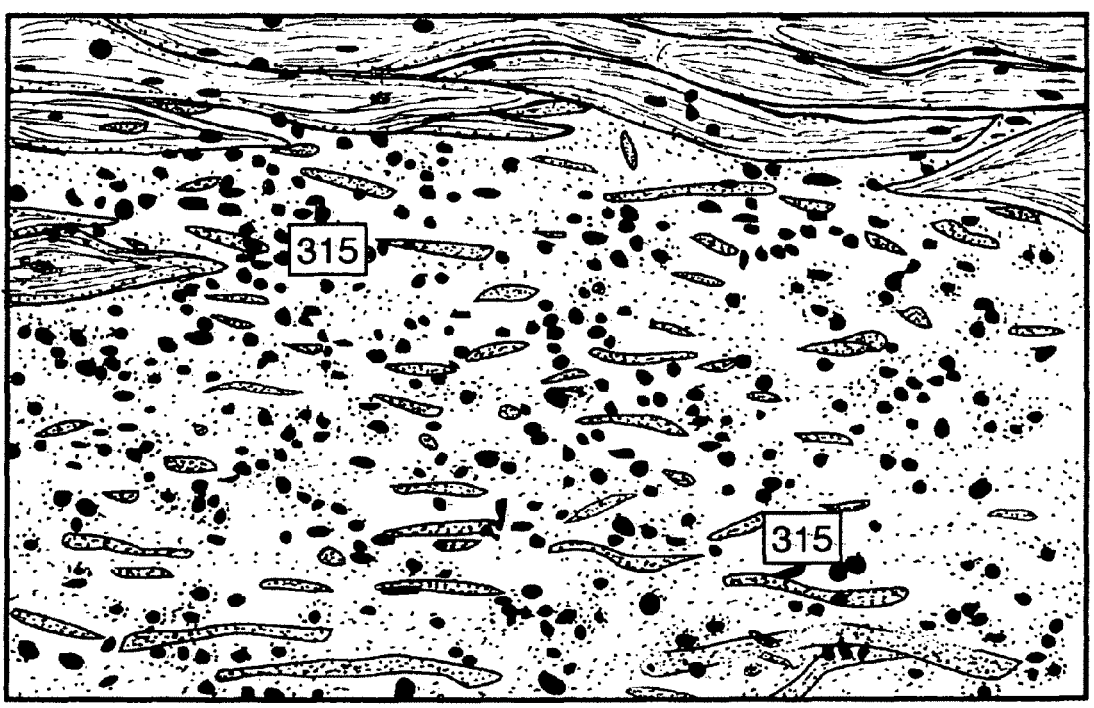
FIG. 3H illustrates an example of the myocardium of an acute myocardial infarction approximately one week after a myocardial infarction occurred. The capillaries, fibroblasts and macrophages fill with hemosiderin.
Figure 3I:
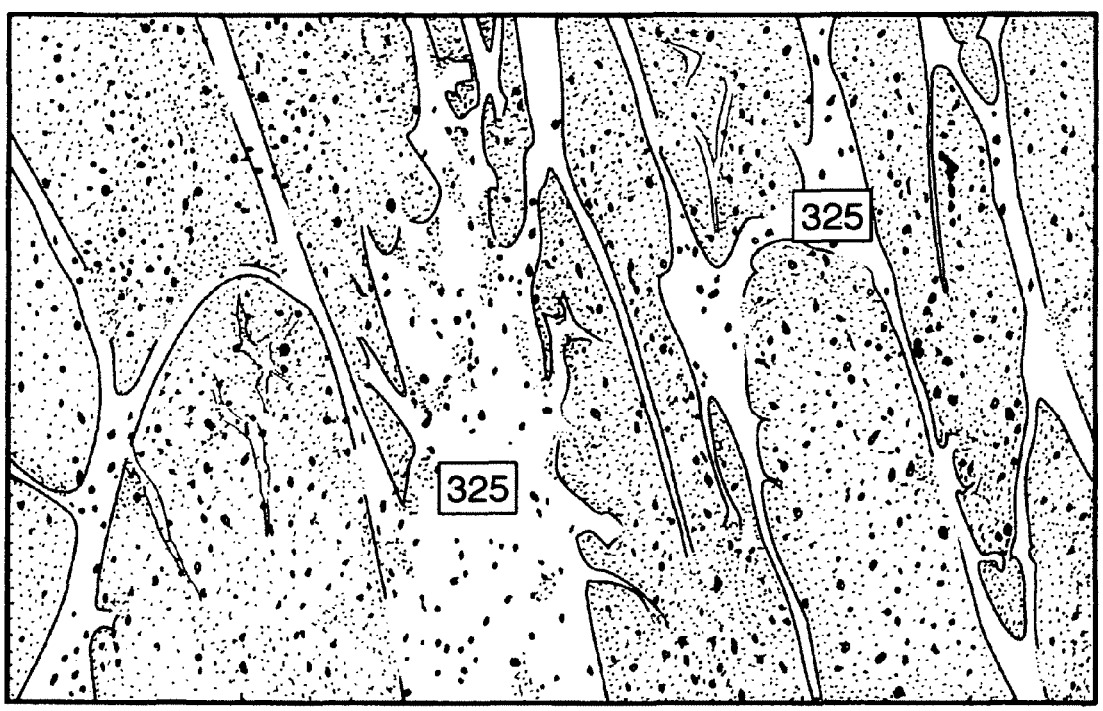
FIG. 3I illustrates an example of the myocardium a couple of weeks after a myocardial infarction. A lot of collagen has been deposited at the site of damage.
Figure 3J:
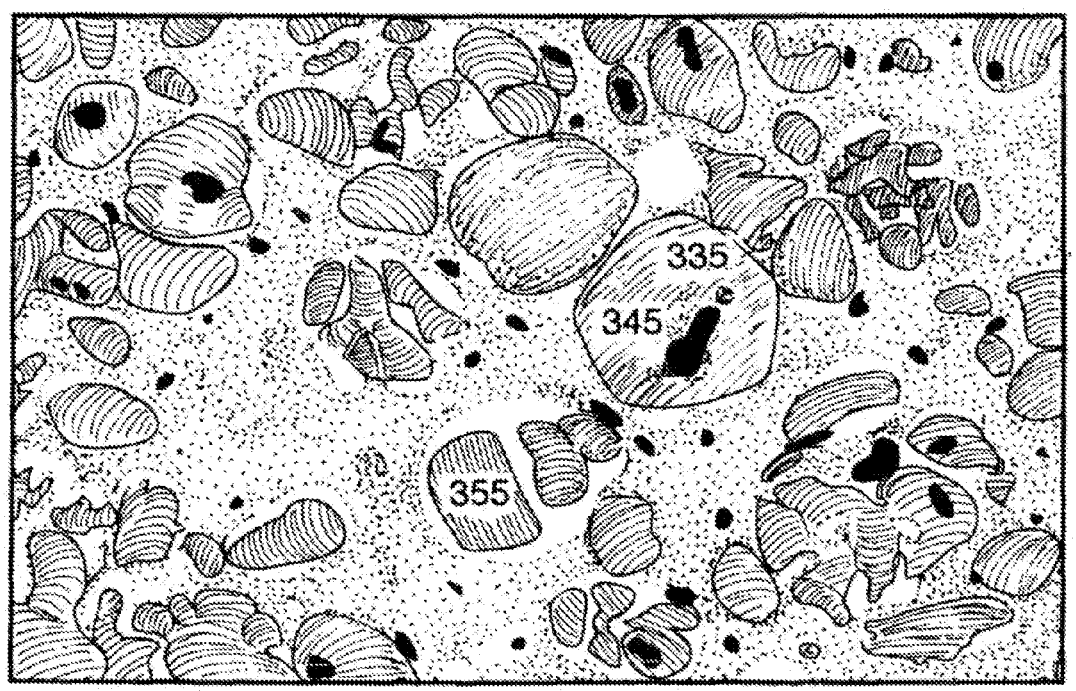
FIG. 3J illustrates myocardium several weeks after a myocardial infarction. Many surviving myocytes appear hypertrophic and their nuclei are dark in color. Interstitial fibrosis is also observed.

"a container"—a receptacle, such as a carton, can, vial, tube, bottle, or jar, in which material is held or carried.

"cardiomyocyte-like"—a cell(s) capable of converting to a cardiomyocyte(s) or a cell or components capable of functioning like a cardiomyocyte and/or expressing one or more cardiac specific molecular marker(s).

"polymer-forming"—any agent or agents capable of forming a gelatinous material either alone or in combination.

"delivery device"—an apparatus or system capable of depositing a solution, powder, concentrate, a single reagent and/or multiple reagents.

"pro-fibroblastic" agent—one or more compounds capable of retaining, inducing proliferation of and/or recruiting fibroblasts cells.

"compliance"—The ability of a blood vessel or a cardiac chamber to change its volume in response to changes in pressure has important physiological implications. In physical terms, the relationship between a change in volume (D V) and a change in pressure (D P) is termed compliance (C), where $C=\Delta V/\Delta P$. Compliance, therefore, is related to the ease by which a given change in pressure causes a change in volume. In biological tissues, the relationship between $\Delta V$ and $\Delta P$ is not linear. Compliance is the slope of the line relating volume and pressure that decreases at higher volumes and pressures. Another way to view this is that the "stiffness" of the chamber or vessel wall increases at higher volumes and pressures. Changes in compliance have important physiological effects in cardiac chambers and blood vessels.

DETAILED DESCRIPTION

In the following section, several embodiments of, for example, processes, compositions, devices and methods are described in order to thoroughly detail various embodiments. It will be obvious though, to one skilled in the art that practicing the various embodiments does not require the employment of all or even some of the specific details outlined herein. In some cases, well known methods or components have not been included in the description in order to prevent unnecessarily masking various embodiments.

Methods and compositions to treat a ventricle after a myocardial infarction (MI) are disclosed. In one embodiment, the infarct region or the area of the ventricle containing the infarct injury may be treated alone or in combination with other treatments. One benefit to such treatment is that the region of injury may be targeted with little or no affect on the outlying healthy heart tissue. In addition, another benefit of such treatment is that the treatment may prevent the loss of functionality of a region of injury due to the normal remodeling and scar forming procedure to mend an infarct region. Another benefit may be that the treatment may increase the compliance of the ventricle. Another benefit may be that the treatment may reduce or eliminate the debris found in the post infarct region to encourage an angiogenic response and/or allow/enhance the microenvironment for ECM scaffold remodeling/regeneration. Still another benefit is the reduction in thinning of a ventricular wall of an infarct zone. In the following description, structural reinforcement of the infarct region of the ventricle is described. Since most myocardial infarctions occur in the left ventricle most descriptions will be directed towards left ventricle repair. But, it is appreciated that treatment of the right ventricle may be achieved in a similar manner.

If the remodeling of the infarct region could be modified prior to scar formation and ultimate thinning of the ventricular wall, functional tissue may be rescued. The inhibition of scar formation and guided regeneration of viable cells would lead to increased wall strength and alter collagen deposition, instead of thinning and hypertrophied myocytes. Further, decreasing the probability of wall thinning and fortifying the influx of cellular components such as immunotolerant cells might be beneficial and preferred over the current treatment of an MI, namely continual exposure to systemic drugs to treat the symptoms and not the disease. Another benefit may be that any one of the treatments herein may result in an increase in compliance of the ventricle. Thus, any one or more combinations of these treatments may provide a potential for healing the infarct region and prevention of further complications.

In other embodiments, a kit (e.g., a pre-manufactured package) is disclosed. A suitable kit includes at least one component (e.g., cellular component such as α-1,3-galactosyltransferase (GGTA1) knockout heart cells or cardiomyocyte-like cell(s) capable of converting to a cardiomyocyte(s) or a cell or components capable of functioning like a cardiomyocyte) and/or agent and a lumen to house the component. The component has a property that may increase the modulus (tensile strength, "stiffness") of elasticity of the infarct region, increase compliance of the ventricle and/or prevent or reduce thinning caused by remodeling (e.g., by replacing the myocardial cells). The kit may be suitable, in one example, in the methods described.

Electrical System of the Heart

When a transmural myocardial infarction in the left ventricle occurs, the affected area suffers a loss of contractile fibers that depends upon the degree of collateral circulation to the area. For example, the infarction may either leave a non-contractile scar or leave some viable myocardium interspersed with scar tissue, with the myocardial fibers that surround the infarcted area suffering a variable amount of destruction. In any case, regions in and around the infarct suffer impaired contractility, and this is responsible for the ventricular dysfunction that initiates the remodeling process as described above. Whether the infarction results in a non-contractile scar or a fibrous region with diminished contractility, the viable myocardium in proximity to the infarct are the regions of the ventricle that are least able to respond to the increased stresses brought about by ventricular dysfunction in a physiologically appropriate manner. These regions are thus the parts of the ventricle that are most vulnerable to the post-infarct remodeling process. In one embodiment, a method to treat in the proximity of the infarct to lessen mechanical stress without adversely compromising ventricular systolic function and decrease the undesirable remodeling of the region is proposed. Known and conventional electrostimulatory techniques may be used in the context of any of the embodiments.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, one embodiment proposes to treat a ventricular region to induce contraction earlier than parts of the ventricle to decrease both the preload and afterload which may decrease the mechanical stress experienced by the region relative to other regions. This may result in the region being more efficient by lessening its metabolic demands such as oxygen requirements.

In one embodiment, electrostimulatory pacing pulses may be delivered to one or more sites in or around the infarct in a manner that pre-excites those sites relative to the rest of the ventricle. As the term is used herein, a pacing pulse is any electrical stimulation and possibly targeted chemical stimulation of the heart of sufficient energy to initiate a propagating depolarization, whether or not intended to enforce a particular heart rate. In a normal heartbeat, the specialized His-Purkinje conduction network of the heart rapidly conducts excitatory impulses from the sinoatrial node to the atrio-ventricular node that likely results in a coordinated contraction of both ventricles.

Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus, the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. This pre-excitation of a paced site relative to other sites can be used to deliberately change the distribution of wall stress experienced by the ventricle during the cardiac pumping cycle. Pre-excitation of the infarct region relative to other regions unloads the infarct region from mechanical stress by decreasing its afterload and preload, thus preventing or minimizing the remodeling that would otherwise occur. Since the contractility of the infarct region is impaired, pre-excitation of the region may result in a resynchronized ventricular contraction that is hemodynamically more effective. This may be beneficial in reducing the stimulus for remodeling and reducing the incidence of angina due to coronary insufficiency. Decreasing the wall stress of the infarct region also reduces its oxygen requirements and decreases the probability of an arrhythmia arising in the region.

In one embodiment, pacing therapy to unload the infarct region may be implemented by pacing the ventricles at a single site in proximity to the infarct region or at multiple ventricular sites. With multiple sites, the pacing pulses may be delivered simultaneously or in a controlled pulse output sequence. As outlined below, the single-site or multiple site pacing may be performed using a bradycardia pacing algorithm such as an inhibited demand mode or a triggered mode.

In one embodiment, to pre-excite the infarct region, one or more pacing electrodes may be placed in proximity to the region. To locate the infarct region several techniques to map the heart may be used including, but not limited, to ultrasonic imaging, PET scans, and thallium scans, and MRI perfusion scans. In the case of a left ventricular infarct, epicardial leads may be placed directly on the epicardium with a thoracotomy (an open chest surgical operation) or with a thorascopic procedure, or leads may be threaded from the upper venous system into a cardiac vein via the coronary sinus. (See, e.g., U.S. Pat. No. 5,935,160 incorporated herein by reference.)

Pacemakers

A permanent pacemaker is a small device that is implanted under the skin (often in the shoulder area just under the collarbone), and it sends electrical signals to start or regulate a slow heartbeat. As the term is used herein, a "pacemaker" should be taken to mean any cardiac rhythm management device with a pacing functionality regardless of any other functions it may perform. A permanent pacemaker may be used to make the heartbeat if the heart's natural pacemaker (the sinoatrial node SA node) is not functioning properly and has developed an abnormal heart rate or rhythm, or if the electrical pathways are blocked.

Pacemakers are usually implanted subcutaneously on the patient's chest, and are connected to sensing/pacing electrodes by leads either threaded through the vessels of the upper venous system to the heart or by leads that penetrate the chest wall. The controller of the pacemaker may be made up of a microprocessor communicating with a memory via a bidirectional data bus, where the memory typically comprises a ROM (read-only memory) for program storage and a RAM (random-access memory) for data storage. The controller may be implemented by other types of logic circuitry (e.g., discrete components or programmable logic arrays) using a microprocessor-based system. The controller is capable of operating the pacemaker in a number of programmed modes where a programmed mode defines how pacing pulses are output in response to sensed events and expiration of time intervals. A telemetry interface may also be provided for communicating with an external programmer.

An electrical stimulus is generated by the sinus node (also called the sinoatrial node, or SA node), which is a small mass of specialized tissue located in the right atrium (right upper chamber) of the heart. The sinus node generates an electrical stimulus periodically. This electrical stimulus travels down through the conduction pathways and causes the heart's chambers to contract and pump out blood. The right and left atria (the two upper chambers of the heart) are stimulated first and contract a short period of time before the right and left ventricles (the two lower chambers of the heart). The electrical impulse travels from the sinus node to the atrioventricular (AV) node, where it stops for a very short period, then continues down the conduction pathways via the bundle of His into the ventricles. The bundle of His divides into right and left pathways to provide electrical stimulation to both ventricles.

Normally, as the electrical impulse moves through the heart, the heart contracts. One contraction represents one heartbeat. The atria contract a fraction of a second before the ventricles so their blood empties into the ventricles before the ventricles contract.

Under some conditions, almost all heart tissue is capable of starting a heartbeat, or becoming the pacemaker. Some symptoms of arrhythmias include, but are not limited to, weakness, fatigue, palpitations, low blood pressure, and dizziness and fainting. The symptoms of arrhythmias may resemble other conditions or medical problems.

Components of a Permanent Pacemaker/ICD

In one embodiment, a permanent pacemaker may be used. A permanent pacemaker has three principle components a pulse generator, a sealed lithium battery and an electronic circuitry package. The pulse generator produces the electrical signals that make the heart beat. Many pulse generators also have the capability to receive and respond to signals that are sent by the heart itself. One or two wires (also called leads) are insulated flexible wires that conduct electrical signals to the heart from the pulse generator. The leads may also relay signals from the heart to the pulse generator. One end of the lead is attached to the pulse generator and the electrode end of the lead is positioned in the atrium (the upper chamber of the heart) or in the ventricle (the lower chamber of the heart). Pacemaker technology is now much more advanced. Today, pacemakers are able to "sense" when the heart's natural rate falls below the rate that has been programmed into the pacemaker's circuitry. Pacemaker leads may be positioned in the atrium or ventricle, infarct area or any combination of sites depending on the condition requiring the pacemaker to be inserted. Atrial pacemakers and ventricular pacemakers are well known in the art. It is possible to have a pacemaker with leads in any, all or a combination of sites.

In addition, specialty pacemakers that pace either the right atrium or the right ventricle are called "single-chamber" pacemakers. Pacemakers that pace both the right atrium and right ventricle of the heart and require two pacing leads are called "dual-chamber" pacemakers.

Implanting a Pacemaker

In one embodiment, a Pacemaker/ICD insertion may be performed as an outpatient procedure, done in the cardiac catheterization laboratory, or the electrophysiology laboratory. The patient may be awake during the procedure, although sedation may be given to help the patient relax during the procedure. A small incision may be made just under the collarbone. The pacemaker/ICD lead(s) may be inserted into the heart through a blood vessel that runs under the collarbone. Once the lead is in place, it is tested to make sure it is in the right place and is functional. The lead may then be attached to the generator, which may be placed just under the skin through the incision made earlier.

Pre-excitation Pacing

In one embodiment, pre-excitation pacing may be applied to one or more ventricular sites in proximity or within an infarct region which may be delivered by a bradycardia pacing mode, which refers to a pacing algorithm that enforces a certain minimum heart rate. Pacemakers may enforce a minimum heart rate either asynchronously or synchronously. In asynchronous pacing, the heart may be paced at a fixed rate regardless of an intrinsic cardiac activity. Because of the risk of inducing an arrhythmia with asynchronous pacing, most pacemakers for treating bradycardia may be programmed to operate synchronously in a "demand mode" where sensed cardiac events occurring within a defined interval either trigger or inhibit a pacing pulse. Inhibited demand pacing modes utilize escape intervals to control pacing in accordance with sensed intrinsic activity. In an inhibited demand ventricular pacing mode, the ventricle may be paced during a cardiac cycle only after expiration of a defined escape interval during which no intrinsic beat by the chamber is detected. For example, a ventricular escape interval may be defined between ventricular events so as to be restarted with each ventricular sense or pace. The inverse of this escape interval is the minimum rate at which the pacemaker will allow the ventricles to beat, sometimes referred to as the lower rate limit (LRL). In an atrial tracking pacing mode, another ventricular escape interval may be defined between atrial and ventricular events, referred to as the atrio-ventricular interval (AVI). The atrio-ventricular interval is triggered by an atrial sense and stopped by a ventricular sense or pace. A ventricular pace is delivered upon expiration of the atrio-ventricular interval if no ventricular sense occurs before the expiration. It may be desirable in certain subjects (e.g., humans) to decrease the AVI to be below the intrinsic PR interval (i.e., the normal time for an intrinsic ventricular beat to occur after an atrial sense) or increase the LRL to be slightly above the patient's normal resting heart rate. In other embodiments, pre-excitation pacing therapy may be started, stopped, or modified based upon sensor measurements. For example, the pacemaker could measure the impedance between pairs of electrodes to detect wall motion or changes in wall thickness during the cardiac cycle. Separate pairs of electrodes can be used to produce impedance signals from both a paced region and a non-ischemic region, such as the right ventricle if the paced and ischemic region is in the left ventricle. Ischemia in the paced region may be monitored by comparing the timing of the contraction in the paced region with the timing of the non-ischemic region. If the contractions in the paced region are delayed or significantly prolonged, an increase in ischemia can be surmised, and pre-excitation pacing to the area can either be started or increased. Conversely, if a decrease in ischemia is detected, pre-excitation pacing may either be stopped or reduced. Modifications to the pacing therapy can also be made in accordance with detected changes in the wall thickness of the paced region. In another embodiment, an accelerometer or microphone on the pacing lead or in the device package may be used to sense the acoustic energy generated by the heart during a cardiac cycle. Changes in the amplitude or morphology of the acoustic energy signal may then be used to infer changes in the wall motion and the efficiency of contraction and relaxation. The applied pre-excitation pacing therapy may then be modified based upon this information. (See U.S. Pat. No. 6,058,329 and U.S. Pat. No. 6,628,988, hereby incorporated by reference.) A device for delivering pre-excitation pacing therapy as described above may also have other functionality that can be of benefit to patients with ischemic heart disease, such as cardioversion/defibrillation. In one embodiment, a device for delivering pre-excitation pacing therapy as described may be combined with any reinforcement and/or cellular replacement composition.

Pacing Units

In one embodiment, an implanted cardiac rhythm management device may automatically adjust the pulse output sequence in accordance with measurements of myocardial mass. Such measurements may be made by measuring the conduction delays of excitation spreading through the myocardium as sensed by multiple sensing/stimulation electrodes. Increased conductions delays through a region, for example, may be reflective of stress in the region that can be reduced by pre-excitation stimulation. In another embodiment, impedance measurements may be made between electrodes in proximity to the heart that correlate with variations in myocardial mass and contraction sequence. Such measurements may be used to identify akinetic or dyskinetic regions of the myocardium as well as to indicate wall thickness abnormalities. The particular pre-excitation interval used by the device may also be automatically adjusted in accordance with detected changes in the remodeling process. That is, the pre-excitation interval may be shortened as remodeling is reversed, or increased as remodeling worsens. Remodeling changes can be detected by, for example, measuring changes or trends in conduction delays, contraction sequences, end-diastolic volume, stroke volume, ejection fraction, wall thickness, or pressure measurements.

In another embodiment, the pulse output sequence used by a cardiac rhythm management may be alternated between one designed to produce hemodynamically more effective contractions when metabolic needs of the body are great to one designed to promote reverse remodeling when metabolic needs are less. A pulse output sequence that unloads a hypertrophic region may not be the optimum pulse output sequence for maximizing hemodynamic performance. For example, a more hemodynamically effective contraction may be obtained by exciting all areas of the myocardium simultaneously, which may not effectively promote reversal of the hypertrophy or remodeling. The pulse output sequence may therefore be adjusted automatically in accordance with exertion level measurements reflective of metabolic demand so that pulse output sequences that unload hypertrophied or stressed regions are not used during periods of increased exertion.

Mapping of the Heart

In each of the methods described herein, it is appreciated that specific areas of the heart may be targeted for application of any of the incorporated methods, thus there are techniques previously described that may be used for targeting the infarct region. One example of targeting a specific region such as an infarct zone uses a technique known as mapping the heart (U.S. Pat. No. 6,447,504). The data are acquired by using one or more catheters that are advanced into the heart. These catheters usually have electrical and location sensors in their distal tips. Some of the catheters have multiple electrodes on a three-dimensional structure and others have multiple electrodes distributed over a surface area. One example of the later catheter may be a sensor electrode distributed on a series of circumferences of the distal end portion, lying in planes spaced from each other. These techniques provide methods to characterize the condition of the heart in some situations using electrical potentials in the heart tissue as well as using electromechanical mapping, ultrasonic mapping to map the viable and the non-viable regions of the heart for example the left ventricle and the infarct zone. In addition, the ultrasound waves may be used to determine the thickness of the heart tissue in the vicinity of the probe for example, sensing the characteristic of the heart tissue by analyzing the ultrasound signals to determine the depth of the channels. Another method known as viability mapping (for example Spect, MRI, PET) may also be used. Viability mapping may be used to identify areas of the heart that are ischemic but still viable as well as area that have lost their viability due to infarction. These maps are based on electrophysiological data that indicate the flow of activation signals through the heart tissue. In addition, the data may be biomedical and/or mechanical data for example, variations in the thickness of the heart wall between systolic and diastolic stages of the heart cycle. The data that is used to analyze the heart by mapping may also be a combination of electrophysiological and biomedical data in order to more accurately locate and target the infarct region. In absence of viability mapping devices, it is appreciated that the location of the infarction may be also assessed through LV angiography or echo, where location of the akinetic or hypokinetic region may be identified.

Gene Manipulation

Genes that encode polypeptides harboring an antigenic determinant recognized by the recipient organism or polypeptides associated with the synthesis of molecules comprising an antigenic determinant recognized by the recipient organism may be identified using a number of techniques familiar to those skilled in the art. For example, in one embodiment, cDNA libraries are prepared from mRNA from the donor organism, or from a particular cell type, organ or tissue from the donor organism that is to be used in xenotransplantation. A variety of techniques are available for preparing cDNAs.

The resulting cDNAs are inserted into an expression vector such that they are operably linked to a promoter. Preferably, the expression vector also encodes a marker that allows cells containing the expression vector to be distinguished from cells that do not contain the expression vector. For example, the marker may be a selectable marker that allows cells containing the vector to replicate in the presence of a drug. Alternatively, the marker may be a polypeptide which is easily detected, such as green fluorescent protein, red fluorescent protein, CD8, flag tag, HA tag, C-myc, GST, mbp, polyhistidine, and the like. Preferably, in order to facilitate identification of genes that encode polypeptides from the donor organism that harbor an antigenic determinant, only a single cDNA is introduced into each of the host cells. This may be achieved, for example, by infecting the host cells with retroviruses encoding the polypeptide at a level of multiplicity such that each cell is only infected by a single virus.

The cells expressing the polypeptides encoded by the cDNAs from the donor organism are contacted with naturally occurring immunoglobulin family proteins from the host subject. "Naturally occurring immunoglobulin family proteins" may be defined broadly as polypeptides that contain an immunoglobulin domain, and occur naturally in the proposed recipient organism. These proteins, upon contact with polypeptides, lipids, carbohydrates, and any other molecule including an antigenic determinant, may be capable of signaling the presence of an antigenic determinant that is recognized as associated with a recipient organism. Those skilled in the art will appreciate that naturally occurring immunoglobulin family proteins include many different types of molecules and are present on the surface of many different cells. For example, without limitation, the naturally occurring immunoglobulin family proteins may be present in one or a combination of any of the following: sera from one or more recipient organisms, such as human beings; a polyclonal antibody population or an enriched polyclonal antibody population from one or more recipient organism; any other immunoglobulin(s) from one or more recipient organism; or be present on the surface B-cells, T-cells, including CD4+ and/or CD8+ cells, dendritic cells, macrophages and natural killer cells (NK cells) from one or more recipient organism; and any other suitable cell or molecule from one or more recipient organism. Thus, the term "naturally occurring immunoglobulin family proteins" include but are not limited to antibodies, B-cell receptors, T-cell receptors, MHC molecules, cellular receptors, and cell surface molecules.

The expression vectors are introduced into host cells in which the promoter is functional such that the polypeptides encoded by the cDNAs are produced in the host cells. The host cells may be any type of cell capable of expressing the polypeptides encoded by the cDNAs from the promoter. For example, the host cells may be mammalian cells. The mammalian host cells may be swine cells.

Another approach to identify antigenic determinants is to use either cells from pig tissue or human cells, HeLa cells to HEK 293T cells expressing the cDNA library in the pcDNA3 vector. These cells can be subjected to subcellular fractionation to purify the cell surface fraction. The proteins in the cell surface fraction may be subjected to two-dimensional gel electrophoresis followed by SDS-PAGE. This gel is then transferred to nitrocellulose and probed with the naturally occurring immunoglobulin family proteins derived from the recipient, which may or may not have been pre-absorbent on a column removing the antibodies directed against an unwanted surface molecule.

The genes encoding the polypeptides harboring an antigenic determinant recognized by the recipient organism are sequenced using standard technology. To prevent or reduce recognition of the identified polypeptides by the recipient organism, a desired number of the genes encoding the polypeptides are disrupted in cells from the donor organism. In one embodiment, only one gene is disrupted (e.g., $\alpha$-1,3-galactosyltransferase (GGTA1). In another embodiment, two, three, four, five, ten, twenty or more genes may be disrupted. The genes may be disrupted in any cell from the donor organism that is capable of being used to replace a cell or tissue in a xenotransplantation procedure. For example, the genes may be disrupted in cardiomyocytes, granulosa cells, muscle cells and primary fetal fibroblasts, stem cells (hematopoetic stem cells, bone marrow derived stem cells), germ cells, fibroblasts or non-transformed cells from any desired organ or tissue. In one embodiment, the genes may be disrupted in a stem cell population for regeneration of cardiomyocytes within a damaged region.

The genes may be disrupted using a variety of technologies familiar to those skilled in the art. For example, a stop codon may be introduced into the gene by homologous recombination. Alternatively, a deletion may be introduced into the gene by homologous recombination. In some embodiments, stop codons may be introduced in all reading frames in the sequence downstream of the deletion to eliminate artifactual translation products. In further embodiments, the gene may be disrupted by inserting a gene encoding a marker protein therein via homologous recombination. It will be appreciated that the deletion, stop codon, marker gene, or other disruption may be located at any position which prevents or reduces recognition of the antigenic determinants by the immune system of the recipient organism. If the donor cells are diploid, both chromosomal copies of the gene may be disrupted in the donor cells.

Genes encoding polypeptides harboring antigenic determinants recognized by the recipient organism may be sequentially disrupted in cells from the donor organism to generate cells in which each of the desired genes has been disrupted. If desired, after disruption of each of the genes in the cells from the donor organism, the cells may be contacted with serum from the recipient organism to confirm that recognition of the polypeptides encoded by the genes by the recipient organism may be considerably reduced or eliminated. The disruption procedure may be repeated until cells from the donor organism having the desired number of genes disrupted have been generated.

In some embodiments, the donor cells having the sought after disrupted genes may be used to replenish cell populations (e.g., cardiomyocytes) or replace tissues. A variety of techniques may be used to generate the cell populations, or tissues. For example, in one embodiment, the donor cells may be used to generate a genetically modified organism, such as a knockout animal (e.g., a knockout swine or monkey) for example, including tissues or organs in which the desired genes have been disrupted in most or all tissues and organs. A variety of techniques for generating transgenic or genetically modified animals are familiar to those skilled in the art. For example, the nuclei of the donor cells may be removed and transferred into enucleated oocytes capable of developing into a transgenic or genetically modified animal. The oocytes may be from the same species as the donor cells or from a different species. The oocytes including the nuclei from the donor cells may then be introduced into an organism in which they can develop into a transgenic or genetically modified animal. The oocytes may be introduced into an organism from the same species as the donor cells and/or the oocytes or from a different species from the donor cells and/or the oocytes. The oocytes may be allowed to develop into genetically modified organisms and, after birth, the transgenic or genetically modified organisms are allowed to grow until their tissues or organs are suitable for use in a xenotransplantation procedure. The genetically modified animal may also be generated by co-injection of the components necessary to induce the homologous recombination together with sperm into the oocyte.

Alternatively, the donor cells with the desired genes disrupted may be generated artificially by a simulated scaffold that forms the support for the tissue or organ. The scaffold may be a synthetic polymer or may have a biological component, such as a collagen. Such matrices have been described in U.S. Pat. No. 6,051,071 (incorporated in its entirety). Donor cells having the desired genes disrupted may be grown on the scaffold. The scaffold comprising the donor cells is then implanted into the recipient organism. On the other hand, the donor cells alone are delivered to the target site such as the infarct zone.

In another embodiment, donor cells having the desired genes disrupted may be genetically engineered to express a polypeptide beneficial to the recipient. For example, the donor cells may be genetically engineered to express a growth factor or cytokine as well as have a disrupted gene. In another embodiment, the vector may encode a factor that inhibits the activity or reduces the amount of a nucleic acid, polypeptide, carbohydrate, lipid or any other molecules whose production may affect the condition in a negative manner. Theses cells would also contain the desired disrupted gene trait. In another embodiment molecules are expressed by the transgenic or genetically modified animal that diminish rejection of the transplanted organ, tissue or cells in combination with the disrupted gene phenotype.

Preparation of cDNA Libraries cDNA libraries may be prepared from polyA+ RNA from the organism, cell type, tissue, or organ that is the donor in xenotransplantation. For example, if the donor organism is a pig, the mRNA may be prepared from any desired cells, tissue or organ, including but not limited to kidney, liver, pancreas, heart, heart valve, lung, intestine, brain, cornea, endothelial cells or peripheral blood cells. If desired, the cDNA libraries may be obtained from a commercial source such as Clontech (Palo Alto, Calif.) after supplying the source with tissue, total RNA or polyA+ mRNA.

Alternatively, cDNA libraries are prepared using polyA+ RNA isolated from donor organs obtained from a local slaughterhouse. In one embodiment, the mRNAs may be obtained from one or more of the following organs including, but not limited to, the heart, heart valve, cornea, lung, intestine, or muscle and endothelial cells from large vessels.

An RNA preparation kit may be obtained from Invitrogen (Carlsbad, Calif.) The mRNA may be prepared according to the manufacturer's instructions or as known in the art. Briefly, the selected organs may be individually homogenized and the cells may be lysed in RNase free lysis buffer. The lysate may be passed through an 18-21 gauge needle. PolyA+ RNA may be isolated by incubating the lysate with oligo(dt) cellulose in batch and rotating. The oligo(dt) cellulose may be loaded onto a column and extensively washed before the RNA is eluted off the oligo(dt) cellulose. The quality and the quantity of the mRNA may be monitored by visualization of the mRNA by agarose gel electrophoresis and by optical density (OD), respectively.

The mRNA obtained as described above may then used to prepare double stranded cDNA using a modification of the protocol described in Huynh, et al., DNA Cloning, 1984, pp. 49-78, 1, the disclosure of which is incorporated herein by reference in its entirety. Briefly, mRNA is converted into double-stranded DNA having unique ends that facilitate directional cloning into a vector, such as a retrovirus vector. First, the mRNA is hybridized to a linker-primer that incorporates a poly(dt) tract (at its 3' end) as well as a restriction site for Not I. The linker-primer is extended using an RNase version of the Moloney murine leukemia virus transcriptase (Super Script, Gibco, BRL) and a nucleotide mix in which dCTP is replaced with 5-methyl-dCTP. When first strand synthesis is completed, the reaction mixture is transferred into a second tube that contains the pre-chilled second-strand mixture. The second strand is synthesized using RNAse H and *E. Coli* DNA polymerase I. Finally, a blunting step consisting of treatment with Mung bean nuclease and Klenow fragment is carried out to prepare the cDNA for ligation to a linker, such as an EcoRI linker.

α-1,3-galactosyltransferase (GGTA1) Knockout Cells

One approach for generating a transgenic animal that produces immunotolerant cells involves micro-injection of naked DNA into a cell, preferentially into a pronucleus of an animal at an early embryonic stage (usually the zygote/one-cell stage). The production of one immunotolerant cell, the α-1,3-galactosyltransferase (GGTA1) knockout swine cells, is incorporated here in its entirety (U.S. Pat. No. 6,153,428). DNA injected as described integrates into the native genetic material of the embryo, and will be replicated together with the chromosomal DNA of the host organism. Allowing the transgene to be passed to all cells of the developing organism including the germ line. Transgene DNA that is transmitted to the germ line gives rise to transgenic offspring. All transgenic animals (50% of the offspring) derived from one founder animal are referred to as a transgenic line. If the injected transgene DNA integrates into chromosomal DNA at a stage later than the one cell embryo not all cells of the organism will be transgenic, and the animal is referred to as being genetically mosaic. Genetically mosaic animals can be either germ line transmitters or non-transmitters. The general approach of microinjection of heterologous DNA constructs into early embryonic cells is usually restricted to the generation of dominant effects, i.e., one allele of the transgene (hemizygous) causes expression of a phenotype. See Palmiter, et al., Ann. Rev. Genetics, 1986, p. 465, 20.

In a different approach, animals may be genetically altered by embryonic stem (ES) cell-mediated transgenesis (Gossler et al. 1986, Proc. Natl. Acad. Sci. USA. 83:9065). ES cell lines may be derived from early embryos, either from the inner cell mass (ICM) of a blastocyst (an embryo at a relatively early stage of development), or migrating primordial germ cells (PGC) in the embryonic gonads. They have the potential to be cultured in vitro over many passages (i.e., are conditionally immortalized), and they are pluripotent, or totipotent (i.e., are capable of differentiating and giving rise to all cell types). ES cells can be introduced into a recipient blastocyst transferred to the uterus of a foster mother for development to term. A recipient blastocyst injected with ES cells can develop into a chimeric animal, due to the contributions from the host embryo and the embryonic stem cells. ES cells can be transfected with heterologous gene constructions that may cause either dominant effects, inactivate whole genes or introduce subtle changes including point mutations. Subsequent to clonal selection for defined genetic changes, a small number of ES cells can be reintroduced into recipient embryos (blastocysts or morulae) where they potentially differentiate into all tissues of the animal including the germ line and thus, give rise to stable lines of animals with designed genetic modifications. Totipotent porcine embryonic stem cells can be genetically altered to have a heterozygous (+/−) mutant, preferably null mutant allele, particularly one produced by homologous recombination in such embryonic stem cells. Alternatively, gene targeting events by homologous recombination can be carried out at the same locus in two consecutive rounds yielding clones of cells that result in a homozygous (−/−) mutant, preferably a null mutant. See Ramirez-Solis, et al., *Methods in Enzymol*, 1993, p. 855, 225.

In one preferred embodiment of this invention, a DNA sequence is integrated into the native genetic material of the swine and produces antisense RNA that binds to and prevents the translation of the native mRNA encoding. α-1,3-galactosyltransferase in the transgenic swine.

In a particularly preferred embodiment, the genome of the transgenic swine is modified to include a construct comprising a DNA complementary portion of the α-1,3-galactosyltransferase coding region that will prevent expression of all or part of the biologically active enzyme.

In another embodiment of the invention, cells or cell lines from non-mutant swine are made with the α-1,3-galactosyltransferase inactivated on one or both alleles through the use of an integrated antisense sequence which binds to and prevents the translation of the native mRNA encoding the α-1, 3-galactosyltransferase in the cells or cell lines. The integrated antisense sequence, such as the RNA sequence transcribed, is delivered to the cells by various means such as electroporation, retroviral transduction or lipofection.

In another preferred embodiment, the transgenic swine is made to produce a ribozyme (catalytic RNA) that cleaves the α-1,3-galactosyltransferase mRNA with specificity. Ribozymes are specific domains of RNA which have enzymatic activity, either acting as an enzyme on other RNA molecules or acting intramolecularly in reactions such as self-splicing or self-cleaving. See Long, D. M., et al., FASEB Journal, 1993, pp. 25-30, 7.

The DNA for the ribozymes is integrated into the genetic material of an animal, tissue or cell and is transcribed (constitutively or inducibly) to produce a ribozyme which is capable of selectively binding with and cleaving the α-1,3-galactosyltransferase mRNA.

In another preferred embodiment, using cultured porcine embryonic stem cells, a mutation, preferably a null mutation may be introduced by gene targeting at the native genomic locus encoding. α-1,3-galactosyltransferase. Gene targeting by homologous recombination in ES cells is performed using constructs containing extensive sequence homology to the native gene, but specific mutations at positions in the gene that are critical for generating a biologically active protein. Therefore, mutations can be located in regions important for translation, transcription or those coding for functional domains of the protein. Selection for ES clones that have homologously recombined a gene targeting construct, also termed gene "knockout" construct, may be achieved using specific marker genes. The standard procedure is to use a combination of two drug selectable markers including one for positive selection (survival in the presence of drug, if marker is expressed) and one for negative selection (killing in the presence of the drug, if marker is expressed). See Mansour, et al., Nature, 1988, p. 348, 336. One preferred type of targeting vector includes the neomycin phosphotransferase (neo) gene for positive selection in the drug G418, as well as the Herpes Simplex Virus-thymidine kinase (HSV-tk) gene for selective killing in gancyclovir. Drug selection in G418 and gancyclovir, also termed positive negative selection (PNS), allows for enrichment of ES cell clones that have undergone gene targeting, rather than random integration events. See Mansour, et al., Nature, 1988, p. 348, 336; Tubulewicz, et al., Cell, 1991, p. 1153, 65. Confirmation of homologous recombination events is performed using Southern analysis.

In another embodiment of the invention, cells or cell lines from non-mutant swine are made with the α-1,3-galactosyltransferase inactivated on one or both alleles through the use of an integrated ribozyme sequence which binds to and cleaves the native mRNA encoding the α-1,3-galactosyltransferase in the cells or cell lines. The integrated ribozyme sequence, such as the RNA sequence transcribed is delivered to the cells by various means such as electroporation, retroviral transduction or lipofection.

The swine may be preferably an α-1,3-galactosyltransferase negative swine grown from a porcine oocyte whose pronuclear material has been removed and into which has been introduced a totipotent porcine embryonic stem cell using protocols for nuclear transfer. See Prather, et al., Biol. Reprod., 1989, p. 414, 41. ES cells used for nuclear transfer are negative for the expression of α-1,3-galactosyl transferase, or alternatively, totipotent ES cells used for nuclear transfer are mutated in a targeted fashion in at least one allele of the α-1,3-galactosyltransferase gene.

The swine is preferably lacking expression of the α-1,3-galactosyltransferase gene and bred from chimeric animals that are generated from ES cells by blastocyst injection or morula aggregation. ES cells used to generate the null-mutated chimeric animal may be mutated at least in one allele of the α-1,3-galactosyltransferase gene locus, using gene targeting by homologous recombination.

A chimeric swine is preferably constituted by ES cells mutated in one allele of the α-1,3-galactosyltransferase gene. Derived from mutated ES cells are also germ cells, male or female gametes that allow the mutation to be passed to offspring, and allow for breeding of heterozygous mutant sibling pigs to yield animals which are homozygous mutant at the α-1,3-galactosyltransferase locus. Also described is a swine, deficient for an α-1,3-galactosyltransferase protein (i.e., characterized by lack of expression of α-1,3-galactosyltransferase protein) and have little, if any, functional Galα1-3Galβ1-4GlcNAc epitope-containing carbohydrate antigen on the cell surface are produced. Further described are methods of producing transgenic swine and methods of producing tissue from heterozygous swine or homozygous swine of the present invention. The present invention also relates to cell lines, such as swine cell lines, in which the α-1,3-galactosyltransferase gene is inactivated on one or both alleles and use of such cell lines as a source of tissue and cells for transplantation.

Tissues, organs and purified or substantially pure cells obtained-from transgenic swine, more specifically from hemizygous, heterozygous or homozygous mutant animals may be used for xenogeneic transplantation into other mammals including humans in which tissues, or cells may be required. The α-1,3-galactosyltransferase inactive cells may themselves be the treatment or therapeutic/clinical product. In another embodiment, α-1,3-galactosyltransferase inactive cells produced by the above described method may be further manipulated, using known methods, to introduce a gene or genes of interest, which encode(s) a product(s), such as a therapeutic product, to be provided to a subject. In this embodiment, the α-1,3-galactosyltransferase deficient tissue, organ or cells serve as a delivery vehicle for the encoded product(s). For example, cytokines that augment donor tissue engraftment, Factor VIII, Factor IX, erythropoietin, insulin, human major histocompatibility (MHC) molecules or growth hormone, may be introduced.

A Knockout Swine Cell by Homologous Recombination

Gene targeting by homologous recombination in swine requires several components, including the following: (A) a mutant gene targeting construct including the positive/negative drug-selectable marker genes (see Tubulewicz, et al., Cell, 1991, p. 1153, 65); (B) embryonic stem cell cultures; and (C) the experimental embryology to reconstitute an animal from the cultured cells.

The targeting construct may be provided from a genomic clone that spans most of the antigenic determinant gene and is isolated from a library made of isogenic DNA from a major histocompatibility complex (MHC) haplotype d/d of the miniature swine. Fragments of that genomic clone are introduced into a positive/negative selectable marker cassette specifically developed for gene targeting in embryonic stem (ES) cells and termed pPNT. See Tubulewicz, et al., Cell, 1991, p. 1153. 65. This gene targeting cassette may include as positive selectable marker the bacterial neomycin phosphotransferase gene (neo) which allows for selection of cells in G418. The neo gene is regulated by a promoter that guarantees high level expression in ES cells such as the phosphoglycerate kinase promoter-1 (PGK-1). Negative selection is accomplished by expressing the Herpes Simplex Virus-thymidine kinase (HSV-tk) gene that allows for selective killing of cells in Gancyclovir. Similar to the neo gene, the HSV-tk gene is regulated by the PGK-1 promoter, as well. In the targeting cassette PPNT, there are unique and convenient cloning sites between the neo and the HSV-tk gene which are suitable sites to introduce the genomic fragment of the antigenic determinant gene upstream of the translation initiation signal AUG. This fragment of approximately 2 kb of DNA is cloned in reverse orientation to the direction of transcription of the PGK-neo cassette to assure that no truncated or residual peptide is generated at the antigenic determinant-locus. Genomic sequences of the antigenic determinant locus downstream may be introduced into PPNT at the 5'-end of the neo gene. This targeting construction termed pPNT-alpha GT1 is linearized and transfected by electroporation into cells such as porcine ES cells. Double selection in G418 (150 to 300 µg/mL) and Gancyclovir is performed to initially isolate clones of ES cells with targeted mutations in the locus. Confirmation of homologous recombinant clones is achieved using Southern analysis.

ES cell clones that have undergone targeted mutagenesis of one allele of the antigenic determinant (eg., α-1,3-galactosyltransferase) locus are subjected to a second round of in vitro mutagenesis or used for reconstituting an animal that contains the mutation. A second round of in vitro mutagenesis may be carried out using an analogous targeting construction with a positive selectable marker gene (eg., hygromycin phosphotransferase hyg).

As for reconstitution of animals, the methods include nuclear transfer, blastocyst injection or morula aggregation. The preferred routes include either blastocyst injection or morula aggregation which yield chimeras between the donor cells and the recipient embryos. For both these methods, recipient embryos are prepared as follows: embryo donor/recipient gilts are synchronized and mated. On day 6 following artificial insemination or natural mating, the gilts may be prepared for surgery as described earlier, anesthetized and the uteri retrogradely flushed using a prewarmed (38.degree. C.) solution of phosphate buffered saline (PBS). Intact blastocysts that are encapsulated by the zona pellucida are placed in a depression slide containing HEPES-buffered medium (Whitten's or TL-HEPES) and approximately 15 to 20 ES cells are injected. Injected embryos may be reimplanted into recipient foster gilts for development to term and pregnancies may be monitored using ultrasound. Offspring may be analyzed for chimerism using the polymerase chain reaction (PCR) of DNA samples extracted from blood, skin and tissue biopsies and primers complementary to the neo or hyg gene. Germ line transmission of the chimeras is assayed using PCR and in situ hybridization of tissue samples obtain from male and female gonads. Male and female chimeras which transmit the ES cell genotype to the germ line are crossed to yield homozygously mutant animals. Analysis of mutant animals for expression of the antigenic determinant (e.g., α-1,3-galactosyltransferase) and binding of human natural antibodies to endothelial cells of those animals is used as final test to assess the validity of gene knockout approach in swine.

Delivery Systems

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,102,926, 6,120,520, 6,251,104, 6,309,370; 6,432,119; 6,485,481). The delivery device may include an apparatus for intracardiac drug administration, including a sensor for positioning within the heart, a delivery device to administer the desired agent and amount at the site of the position sensor. The apparatus may include, for example, a catheter body capable of traversing a blood vessel and a dilatable balloon assembly coupled to the catheter body comprising a balloon having a proximal wall. A needle may be disposed within the catheter body and includes a lumen having dimensions suitable for a needle to be advanced there through. The needle body includes an end coupled to the proximal wall of the balloon. The apparatus also includes an imaging body disposed within the catheter body and including a lumen having a dimension suitable for a portion of an imaging device to be advanced there through. The apparatus may further include a portion of an imaging device disposed within the imaging body adapted to generate imaging signal of the infarct region within the ventricle. The apparatus may be suitable for accurately introducing a treatment agent at a desired treatment site.

In another embodiment a needle catheter used to deliver the agent to the ventricle for example, the infarct region, may be configured to include a feedback sensor for mapping the penetration depth and location of the needle insertion. The use of a feedback sensor provides the advantage of accurately targeting the injection location. Depending on the type of agent administered, the target location for delivering the agent may vary. For example, one agent may require multiple small injections within an infarct region where no two injections penetrate the same site.

In other embodiments, the catheter assembly may include a maneuverable instrument. This catheter assembly includes a flexible assembly. The catheter assembly may be deflectable and includes a first catheter, a second catheter, and a third catheter. The second catheter fits coaxially within the first catheter. At least one of the first catheter and the second catheter include a deflectable portion to allow deflection of that catheter from a first position to a second position, and the other of the first catheter and second catheter includes a portion which is preshaped (e.g., an angled portion formed by two segments of the angled portion). The third catheter has a sheath and a medical instrument positioned within the sheath. The third catheter fits coaxially within the second catheter. In another embodiment, a stabilizer, such as a donut shaped balloon, is coupled to a distal portion of the third catheter. Each catheter is free to move longitudinally and radially relative to the other catheters. The catheter assembly may be used but not limited to the local delivery of bioagents, such as cells used for cell therapy, one or more growth factors for fibroblast retention, or vectors containing genes for gene therapy, to the left ventricle. In one embodiment, the catheter assembly described may be used in delivering cell therapy for heart failure or to treat one or more portions of the heart that are ischemic. The catheter assembly uses coaxially telescoping catheters at least one or more being deflectable, to position a medical instrument at different target locations within a body organ such as the left ventricle. The catheter assembly may be flexible enough to bend according to the contours of the body organ. The catheter assembly may be flexible in that the catheter assembly may achieve a set angle according to what the medical procedure requires. The catheter assembly will not only allow some flexibility in angle changes, the catheter assembly moves in a three coordinate system allowing an operator greater control over the catheter assembly's movement portion of the second catheter, allowing for the distal tip of the third catheter to be selectively and controllably placed at a multitude of positions. It will be appreciated that the deflectable portion may alternatively be on the second catheter and the preshaped portion may be on the first catheter.

In a further embodiment, the apparatus of U.S. patent application Ser. No. 10/414,767 is incorporated here in its entirety. The apparatus includes a first annular member having a first lumen disposed about a length of the first annular member, and a second annular member coupled to the first annular member having a second lumen disposed about a length of the second annular member, wherein collectively the first annular member and the second annular member have a diameter suitable for placement at a treatment site within a mammalian body. Representatively, distal ends of the first annular member and the second annular member are positioned with respect to one another to allow a combining of treatment agents introduced through each of the first annular member and the second annular member to allow a combining of treatment agents at the treatment site. Such an apparatus is particularly suitable for delivering a multi-component gel material (e.g., individual components through respective annular members that forms a bioerodable gel within an infarct region of a ventricle).

In other embodiments, larger doses of treatment agent may be considered for example about 2 mL to about 250 mL that may require any one or more of the delivery devices such as intra-venous retro infusion, intra-arterial infusion and needle catheter systems (INVIGOR available from Abbott Vascular, Santa Clara, U.S.A.) as well as subxyphoid approaches.

One concern of introducing any treatment agent composition, whether adjacent to a blood vessel to affect therapeutic angiogenesis, adjacent to a tumor to inhibit tumor growth, or to induce or stimulate collagen growth in arthroscopic procedures, is that the composition remains (at least partially) at the treatment site for a desired treatment duration (or a portion of the treatment duration). In this manner, an accurate dosage may be placed at a treatment site with reduced concern that the treatment agent will disperse, perhaps with serious consequences. In one embodiment, a composition and technique for retaining a treatment agent at a treatment site (injection site) is described. In one embodiment, a treatment component (cellular component) and a bioerodable gel or non-bioerodable gel or particle may be introduced at a treatment site (e.g., an injection site). The gel or particle(s) may be introduced prior to, after, or simultaneously with the treatment agent. In one preferred embodiment, the gel or particle(s) acts to retain the treatment agent at the treatment site by, representatively, sealing the treatment site or sealing the treatment agent at the treatment site. The use of a gel or particle(s) with a treatment agent can reduce the amount of treatment agent backflow from the injection site as well as reduce the load requirement of the treatment agent at the treatment site. For example, a bioerodable product such as a gel or particle may decrease the local pressure thereby further resulting in backflow reduction. A non-bioerodable product may also decrease the local pressure to reduce the backflow in a more permanent fashion and at the same time may also lead to an increase in compliance.

Using the above-mentioned techniques, an imaging modality or detectable molecule may be added such as a contrast-assisted fluorescent scope that permits a cardiologist to observe the placement of the catheter tip or other instrument within the heart chamber. A contrast-assisted fluoroscopy utilizes a contrast agent that may be injected into heart chamber and then the area viewed under examination by a scope, thus the topography of the region is more easily observed and may be more easily treated (U.S. Pat. Nos. 6,385,476 and 6,368,285). Suitable imaging techniques include, but are not limited to, ultrasonic imaging, optical imaging, and magnetic resonance imaging, for example, Echo, ECG, SPECT, MRI, and Angiogram. Therefore, mapping of the heart is one technique that may be used in combination with the techniques proposed in the following embodiments. In one embodiment, an echo angiograph may be performed to confirm the occurrence and the location of the infarct region. In another embodiment, a CAT scan may be performed to confirm an MI has occurred and the location of the infarct region. In another embodiment an EKG may be performed to identify the occurrence and location of an infarct. Another possibility is a molecule carried by a cell such as a nucleic acid within a knockout cell (e.g., the $\alpha$-1,3-galactosyltransferase (GGTA1) knockout cells) may be detectible by sequencing the molecule once the cells have been introduced to the site.

In another embodiment, a method may include introducing a treatment agent in a sustained release composition. The preferred period for sustained release of one or more agents is for a period of one to twelve weeks, and in some cases two to eight weeks. Methods for local delivery of sustained release agents include but are not limited to percutaneous devices for example intraventricular (coronary) or intravascular (coronary and peripheral) devices.

Recruiting and Stimulating Agents

1. Agents

Figure 4:
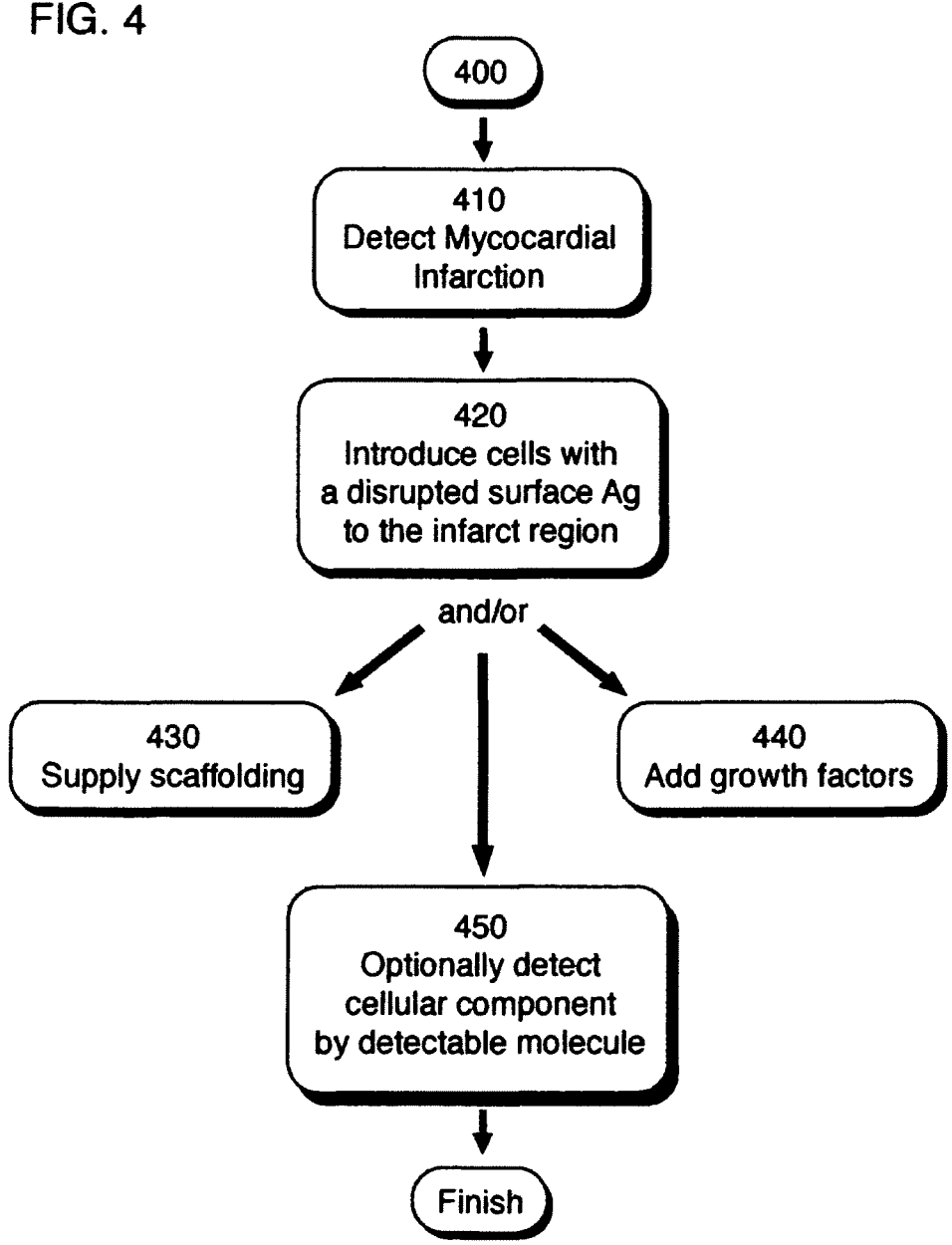
FIG. 4 illustrates an exemplary flow chart of the introduction of a cellular composition to an infarct zone and the replacement of the dead tissue.

FIG. 4 describes one embodiment of a method to treat an infarct region of a left ventricle. This is an illustrative diagram only and any of the treatments may be used in parallel (e.g., at the same time) or sequentially or in any treatment combination. According to the method illustrated in FIG. 4, a myocardial infarction may be detected by an imaging process for example magnetic resonance imaging, optical imaging or ultrasonic imaging for example Echo ECG, spect, MRI, angiogram 410. Next, the area of the left ventricle is replenished by addition of a cardiomyocyte replacement cell of an immunotolerant nature 420. Then growth factors may be introduced to stimulate the replacement cell population to proliferate. In FIG. 4 one option to encourage the replacement cell occupancy of the infarct zone includes the use of scaffolding to generate a matrix for cellular adhesion 430 delivered to the infarct zone. Suitable treatment agents that may modify the replacement cell population include but are not limited to, Angiotensin II, fibroblast growth factor (FGF basic and acidic), insulin growth factor (IGF), TGF-$\beta$ in any of its isoforms (TGF-$\beta$1, TGF-$\beta$2, TGF-$\beta$3), vascular endothelial growth factor (VEGF) in any of its isoforms, tumor necrosis factor-alpha (TGF-$\alpha$), platelet-derived growth factor-BB (PDGF-BB), platelet-derived growth factor-AB (PDGF-AB), angiogenin, angiopoietin-1, Del-1, follistatin, granulocyte colony-stimulating factor (G-CSF), pleiotrophin (PTN), proliferin, transforming growth factor-alpha (TGF-$\alpha$), vascular permeability factor (VPF), stem cell factor, stromal derived factor-1 (SDF-1), human growth factor (HGF) and LIH (leukemia inhibitory factor) genes that encode these proteins, transfected cells carrying the genes of these proteins, small molecules and pro-proteins that also contain these proliferatory properties. In one embodiment, growth factors such as bFGF, and/or VEGF may be used to modify the region surrounding and/or within the infarct.

In one embodiment, a growth factor may be introduced to the infarct region at the same time as another treatment by at least one of the methods described. In one embodiment, any of the described agents may be introduced in one or more doses in a volume of about 1 µL to 1 mL. In another embodiment, any of the described agents may be introduced in one or more doses in a volume of about 1 μL to 300 μL. In another embodiment, any of the described agents may be introduced in one or more doses in a volume of about 1 μL to 100 μL. In a preferred embodiment, any of the described agents may be introduced in one or more doses in a volume of about 1 μL to 50 μL.

In alternate embodiments, the treatment volume may be larger (e.g., intravenous pressure perfusion (IV) route). These volumes may range from about 2 mL to about 250 mL. Alternatively, these volumes may range from about 2 mL to about 100 mL. In other embodiments, these volumes may range from about 2 mL to about 30 mL.

2. Sequence of Treatment

Figure 5:
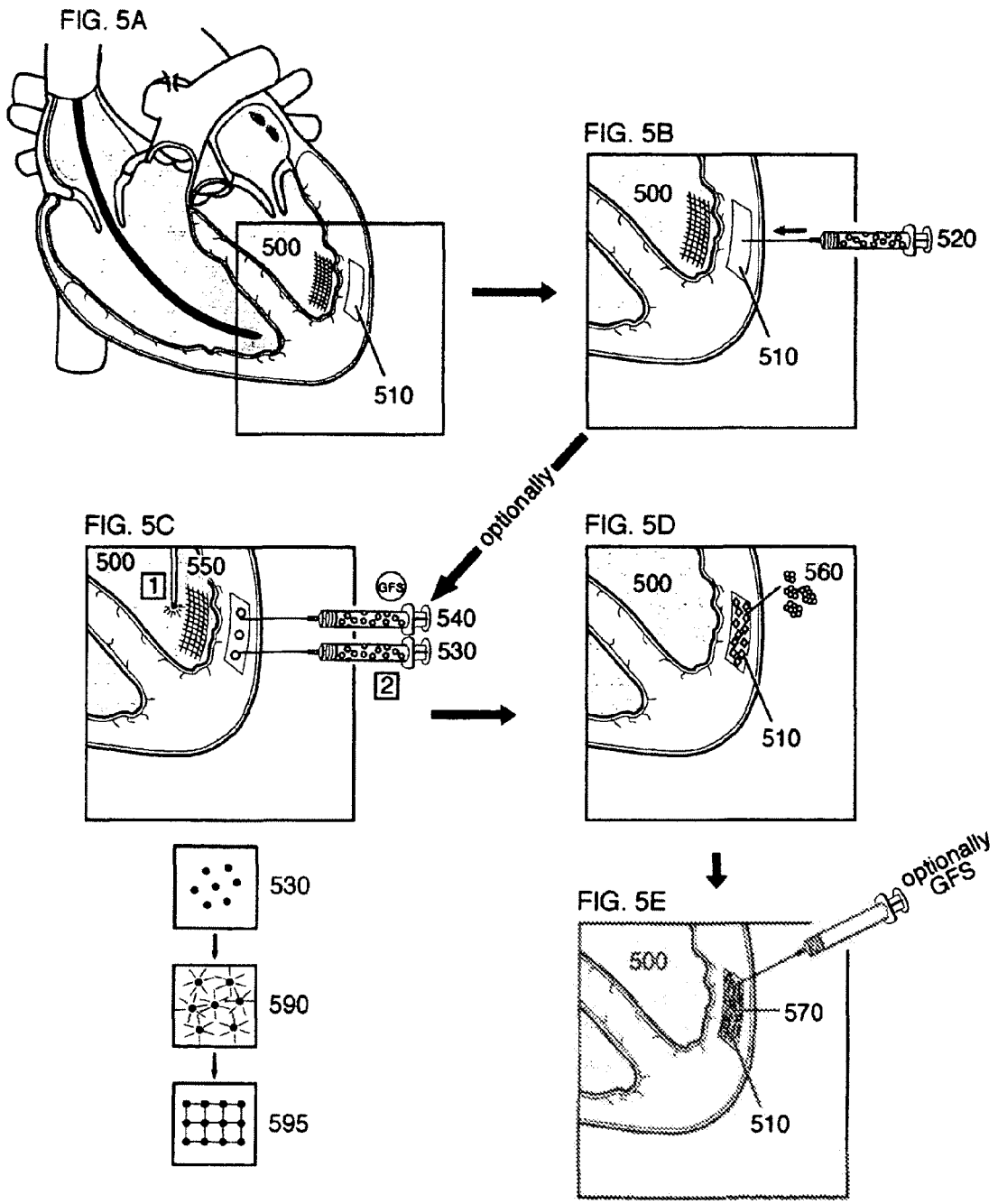
FIG. 5 illustrates a multi-component method for electrostimulating and structurally reinforcing an infarct region.

FIG. 4 illustrates a flow chart of a process for treating MI by introducing immunotolerant cells to the infarct region. FIG. 5A-5E illustrates the introduction, action and proliferation of the immunotolerant cells (e.g., α-1,3-galactosyltransferase (GGTA1) knockout cells). Detection of acute myocardial necrosis may be performed using an ECG (electrocardiogram) or by a more modern technology. For example, one technology such as $^{99}$Technetium-pyrophosphate or $^{111}$In-antimyosin antibody imaging has recently been approved by the Food and Drug Administration. With both of these two tracers, results are obtained only 24-48 hours after acute infarction and therefore, the clinical utility of these techniques have been limited. There is another new agent called $^{99m}$Tc-glucurate that produces results within an hour after acute myocardial infarction (Iskandrian, A. S., et al., *Nuclear Cardiac Imaging: Principles and Applications*, Philadelphia, 1996). Once the MI is detected the exact location of the infarct may be identified using a magnetic resonance imaging then the infarct region may be treated by reinforcement 510. An agent 520 (for example, immunotolerant cells) may be introduced to the infarct region 510. One way the agent may be introduced to the area is percutaneously, with the use of a catheter. A distal end of the catheter is advanced to the infarct zone 530, 540, or 550 and the agent 520 is released. Then for example immunotolerant cells 560 remain in the site and/or proliferate and expand 570. FIG. 5E illustrates the immunotolerant cell replacement and reinforcement of the infarct area.

In one embodiment, any of the described agents may be introduced in one or more doses in a volume of about 1 μL to 1 mL. In another embodiment, any of the described agents may be introduced in one or more doses in a volume of about 1 μL to 300 μL. In another embodiment, any of the described agents may be introduced in one or more doses in a volume of about 1 μL to 100 μL. In a preferred embodiment, any of the described agents may be introduced in one or more doses in a volume of about 1 μL to about 50 μL.

Microparticles

One embodiment of a composition suitable for the described method includes the use of a bioerodable microparticle harboring one or more component (eg.cells, growth factors) in combination with electro-stimulus (eg. a pulse generator). The bioerodable microparticle may consist of a bioerodable polymer such as poly (lactide-co-glycolide). The composition of the bioerodable polymer is controlled to release the component over a period of 1-2 weeks. It was previously demonstrated that biodegradable microparticles for example, poly (lactide-co-glycolide) were capable of controlled release of an oligonucleotide. These microparticles were prepared by the multiple emulsion-solvent evaporation technique. In order to increase the uptake of the component into the microparticles it may be accompanied by polyethylenimine (PEI). The PEI tends to make the microparticles more porous thus facilitating the delivery of the oligonucleotide out of the particles. See De Rosa, et al., *Biodegradable Microparticles for the Controlled Delivery of Oligonucleotides*, Int. J. Pharm., Aug. 21, 2002, pp. 225-228, 242(1-2).

In one preferred embodiment of a composition, a bioerodable microparticle may be a PLGA polymer 50:50 with carboxylic acid end groups. PLGA is a base polymer often used for controlled release of drugs and medical implant materials (i.e., anti-cancer drugs such as anti-prostate cancer agents). Two common delivery forms for controlled release include a microcapsule and a microparticle (e.g., a microsphere). The polymer and the agent are combined and usually heated to form the microparticle prior to delivery to the site of interest (Mitsui Chemicals, Inc). As the microparticles 580 erode 590, a porous network of the microparticle composition is formed 595 in the infarct region resulting in a matrix with a controlled pore size 595. As the porous network is formed in one example one angiogenic and/or pro-fibroblastic factor may be released encouraging the in-growth of new capillaries. In one embodiment, the bioerodable polymer harbors a component such as the growth factor TGF-β1. In one embodiment, the PLGA polymer 50:50 with carboxylic acid end groups harbors TGF-β1 for slow release. It is preferred that each microparticle may release at least 20 percent of its contents and more preferably around 90 percent of its contents. In one embodiment, the microparticle harboring at least one angiogenic and/or pro-fibroblastic agent will degrade slowly over time releasing the factor or release the factor immediately upon contact with the infarct area in order to rapidly recruit fibroblasts to the site. In another embodiment, the microparticles may be a combination of controlled-release microparticles and immediate release microparticles. A preferred rate of deposition of the delivered factor will vary depending on the condition of the subject undergoing treatment.

Another embodiment of a composition suitable for the described method includes the use of microparticles that may harbor one or more of the aforementioned growth factors. The growth factors may be released from the microparticle by controlled-release or rapid release. The microparticles may be placed directly in the infarct region. By directly placing the particles in the infarct region, they may also provide bulk for the region for reinforcement. The non-bioerodable microparticle may consist of a non-bioerodable polymer such as an acrylic based microsphere for example a tris acryl microsphere (provided by Biosphere Medical). In one embodiment, non-bioerodable microparticles may be used alone or in combination with an agent to increase compliance of a ventricle. In another embodiment, non-bioerodable microparticles may be used alone or in combination with an agent to recruit fibroblasts and/or stimulate fibroblast proliferation. In addition, non-bioerodable microparticles may be used to increase compliance and recruit fibroblasts to an infarct region of a ventricle.

In one embodiment, the treatment agent compositions suitable for reinforcement of the infarct zone are rendered resistant to phagocytosis by inhibiting opsonin protein absorption to the composition of the particles. In this regard, treatment agent compositions including sustained release carriers include particles having an average diameter up to about 10 microns. In other situations, the particle size may range from about 1 mm to about 200 mm. The larger size particles may be considered in certain cases to avoid macrophage frustration and to avoid chronic inflammation in the treatment site. When needed, the particle size of up to 200 mm may be considered and may be introduced via an intraventricular catheter or retrograde venous catheter for any of the embodiments herein to avoid chronic inflammation due to macrophage influx into the treatment site.

One method of inhibiting opsonization and subsequent rapid phagocytosis of treatment agents is to form a composition comprising a treatment agent disposed with a carrier for example a sustained release carrier and to coat the carrier with an opsonin inhibitor. One suitable opsonin-inhibitor includes polyethylene glycol (PEG) that creates a brush-like steric barrier to opsonization. PEG may alternatively be blended into the polymer constituting the carrier, or incorporated into the molecular architecture of the polymer constituting the carrier, as a copolymer, to render the carrier resistant to phagocytosis. Examples of preparing the opsonin-inhibited microparticles include the following.

For the encapsulation polymers, a blend of a polyalkylene glycol such as polyethylene glycol (PEG), polypropylene 1,2-glycol or polypropylene 1,3-glycol is co-dissolved with an encapsulating polymer in a common organic solvent during the carrier forming process. The percentage of PEG in the PEG/encapsulating polymer blend is between five percent and 60 percent by weight. Other hydrophilic polymers such as polyvinyl pyrolidone, polyvinyl alchohol, or polyoxyethylene-polyoxypropylene copolymers can be used in place of polyalkylene glycols, although polyalkylene glycols and more specifically, polyethylene glycol is generally preferred.

Alternatively, a diblock or triblock copolymer of an encapsulating polymer such as poly (L-lactide), poly (D,L-lactide), or poly (lactide-co-glycolide) with a polyalkylene glycol may be prepared. Diblocks can be prepared by: (i) reacting the encapsulating polymer with a monomethoxy polyakylene glycol such as PEG with one protected hydroxyl group and one group capable of reacting with the encapsulating polymer, (ii) by polymerizing the encapsulating polymer onto the monomethoxy polyalkylene glycol, such as PEG, with one protected group and one group capable of reacting with the encapsulating polymer; or (iii) by reacting the encapsulating polymer with a polyalkylene glycol such as PEG with amino functional termination. Triblocks can be prepared as described above using branched polyalkylene glycols with protection of groups that are not to react. Opsonization resistant carriers (microparticles/nanoparticles) can also be prepared using the techniques described above to form sustained-release carriers (microparticles/nanoparticles) with these copolymers.

A second way to inhibit opsonization is the biomimetic approach. For example, the external region of cell membrane, known as the "glycocalyx," is dominated by glycoslylated molecules that prevent non-specific adhesion of other molecules and cells. Surfactant polymers may consist of a flexible poly (vinyl amine) backbone randomly distributed dextran and alkanoyl (hexanoyl or lauroyl) side chains which constrain the polymer backbone and lie parallel to the substrate. Hydrated dextran side chains protrude into the aqueous phase, creating a glycocalyx-like monolayer coating that suppresses plasma protein deposition on the foreign body surface. To mimic glycocalyx, glycocalyx-like molecules can be coated on the carriers (e.g., nanoparticles or microparticles) or blended into a polymer constituting the carrier to render the treatment agent resistant to phagocytosis. An alternate biomimetic approach is to coat the carrier with, or blend in, phosphorylcholine or a synthetic mimetic of phosphatidylcholine, into the polymer constituting the carrier.

For catheter delivery, a carrier comprising a treatment agent (e.g., the composition in the form of a nanoparticle or microparticle) may be suspended in a fluid for delivery through the needle, at a concentration of about one percent to about 20 percent weight by volume. In one embodiment, the loading of the treatment agent in a carrier is about 0.5 percent to about 30 percent by weight of the composition. Co-encapsulated with protein or small molecule treatment agents could be stabilizers that prolong the biological half-life of the treatment agent in the carrier upon injection into tissue. Stabilizers may also be added to impart stability to the treatment agent during encapsulation. Hydrophilic polymers such as PEG or biomimetic brush-like dextran structures or phosphorylcholine are either coated on the surface or the carrier, grafted on the surface of the carrier, blended into the polymer constituting the carrier, or incorporated into the molecular architecture of the polymer constituting the carrier, so the carrier is resistant to phagocytosis upon injection into the target tissue location.

Any one or more catheters may be used to deliver the any one or multiple components of the embodiments to the infarct region area. Several catheters have been designed in order to precisely deliver agents to a damaged region within the heart, for example, an infarct region. Several of these catheters have been described (U.S. Pat. Nos. 6,309,370; 6,432,119; 6,485, 481). The delivery device may include an apparatus for intracardiac drug administration, including a sensor for positioning within the heart, a delivery device to administer the desired agent and amount at the site of the position sensor.

Angiogenesis

After an MI, the infarct tissue as well as the border zone and the remote zone begin to remodel. The scar tissue forms in the infarct region as the granulation is replaced with collagen, causing the scar to thin out and stretch. The perfusion in this region is typically 10% of the healthy zone, decreasing the number of active capillaries. Increasing the number of capillaries may lead to an increase in compliance of the ventricle due to filling up with blood. Other benefits of increasing blood flow to the infarcted region include providing a route for circulating stem cells to seed and proliferate in the infarct region. Angiogenesis may also lead to increased oxygenation for the surviving cellular islets within the infarct region, or to prime the infarct region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well. In one embodiment, angiogenesis will be stimulated in any region of the heart—infarct, border or remote-through delivery of angiogenesis-stimulating factors. Examples of these factors include but are not limited to isoforms of VEGF (e.g., VEGF121), FGF (e.g., b-FGF), Del 1, HIF 1-alpha (hypoxia inducing factor), PR39, MCP-1 (monocyte chemotractant protein), Nicotine, PDGF (platelet derived growth factor), IGF (Insulin Growth Factor), TGF alpha (Transforming Growth Factor), HGF (Hepatocyte growth factor), estrogens, Follistatin, Proliferin, Prostaglandin E1, E2, TNF-alpha (tumor necrosis factor), Il-8 (Interleukin 8), Hemotopoietic growth factors, erythropoietin, G-CSF (granulocyte colony-stimulating factors), PD-ECGF (platelet-derived endothelial growth factor), Angogenin. In other embodiments, these factors may be provided in a sustained release formulation as independent factor or in combination with other factors or appropriate gene vectors with any of the gel or microparticle components described in this application.

Microparticles and Angiogenic and Pro-fibroblasticAgents

The microparticles may be prepared as microparticles harboring an angiogenic and/or pro-fibroblastic agent. On the other hand, the microparticles may be prepared and then the angiogenic and/or pro-fibroblastic agent introduced into the microparticle, for example, by diffusion prior to introduction to the infarct region. In the later example, the microparticles might also be coated with the factor and upon introduction to the infarct region the factor immediately recruits fibroblasts to the area. Additionally, the microparticle-factor composition might consist of any combination of the above-mentioned treatments. In other embodiments, it may be necessary to add at least one pharmaceutically acceptable inhibitor to the microparticles that prevents decomposition of the angiogenic or pro-fibroblastic agent.

Microparticle Components

FIG. 4 describes a method to structurally reinforce the infarct region by replacing damaged tissue. This method may be combined with any of the methods describing introducing angiogenic and/or fibroblast-recruiting agents, for example growth factors, to the infarct region to retain and/or promote fibroblast migration to this zone. This method may be combined with any of the methods describing introducing electrical stimulation to the infarct zone. Microparticles capable of taking up fluid will be introduced to the infarct region. Examples of these microparticles include swellable non-biological or synthetic biological particles. The microparticles may be introduced to the infarct zone and become trapped in the tissue. The microparticles tend to immediately start to swell. The swollen microparticles remain lodged in the tissue and provide reinforcement to the ventricular wall and add thickness to the thinning infarct region.

The dimensions of the infarct zone may determine the size range of the microparticles and the number of microparticles introduced to the infarct region. This will insure that the optimum post-hydrated microparticle mass is achieved. An embodiment relates to microparticles that are about 200 microns or less in diameter. In another embodiment the microparticles may be about 20 microns or less in diameter. In a preferred embodiment, the particle size may be about 5-10 microns in diameter. Particles of about 20 microns or less may also include an opsonization inhibitor (previously discussed). The swellable microparticles may be a range of sizes introduced to the infarct region. In one embodiment, the swellable non-biological material may be a hydrogel microsphere material. These microparticles are available commercially (A.P. Pharma or BioSphere Medical). These microparticles are resistant to non-specific absorption and are bio-stable. Microparticles formed from the polymerization of an acidic monomer such as Methacrylic acid may also be used. Microspheres containing carboxylic acid groups have been shown to be angiogenic in impaired wound healing models.

In other embodiments, the delivery of a nonbiologic or synthetic gel may be combined with angiogenic and/or fibroblast recruiting agents utilizing microparticles capable of releasing the agents at a rate optimal for fibroblast retention and migration in the infarct region.

In one embodiment, immunotolerant cells suspended in a solution, such as a medium, may be introduced to the infarct region for structural reinforcement of the ventricular wall. Media that may be used to support the growth and/or viability of the cells are known in the art and include mammalian cell culture media, such as those produced by Gibco BRL (Gaithersburg, Md.). See 1994 Gibco BRL Catalogue & Reference Guide. The medium can be serum-free but is preferably supplemented with animal serum such as fetal calf serum. Optionally, growth factors can be included. Media that are used to promote proliferation of cells and media that are used for maintenance of cells prior to transplantation can differ. A preferred growth medium for cells such as a muscle cell may be MCDB 120+dexamethasone, e.g., 0.39 µg/mL,+Epidermal Growth Factor (EGF), e.g., 10 ng/mL,+fetal calf serum, e.g., 15%. A preferred medium for muscle cell maintenance is DMEM supplemented with protein, e.g., 10% horse serum. Other exemplary media are taught, for example, in Henry, et al., Diabetes, 1995, p. 936, 44; WO 98/54301; and Li, et al., Can. J. Cardiol., 1998, p. 735, 14.

Cells may be suspended in a solution or embedded in a support matrix when contained in an appropriate delivery device. As used herein, the term "solution" includes a pharmaceutically acceptable carrier or diluent in which the cells of the invention are suspended such that they remain viable. Pharmaceutically acceptable carriers and diluents include saline, aqueous buffer solutions, solvents and/or dispersion media. The use of such carriers and diluents is well known in the art. A solution may preferably be sterile and fluid. Preferably, the solution may be stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention may be prepared by incorporating cells as described herein in a pharmaceutically acceptable carrier or diluent and, as required, other ingredients enumerated above, followed by filtered sterilization.

According to certain embodiments of the invention the composition may contain compounds such as pharmaceuticals (e.g., antibiotic or agents that act on the heart), factors such as growth factors that may stimulate myoblast survival, proliferation, or differentiation, or factors that may promote angiogenesis.

In one embodiment, delivery of cells or other components directly to the damaged area of the heart may be accomplished with a catheter that accesses the ischemic area of the heart and enters the myocardial tissue. For example, a catheter may be introduced percutaneously and routed through the vascular system or by catheters that reach the heart through surgical incisions such as a limited thoracotomy involving an incision between the ribs. The cells remain in the infarct region to fortify the tissue and enhance the modulus (wall strength/elongation=modulus) of elasticity as well as replace the lost cardiomyocytes.

Methods for Introduction and Action

FIG. 5A-5E illustrates the introduction and action of cellular components to the infarct region to replace dead cardiomyocyte cells. The cellular component may be introduced to the site 500 by a minimally invasive procedure 510. The solution may be injected in the infarct zone during an open chest procedure 520. The introduction of the pro-fibroblastic agent(s) includes one of the following procedures: sub-xiphoid and percutaneously 530. The mode of introduction of the pro-fibroblastic agent(s) by a percutaneous injection includes one of the following consisting of an intraventricular (coronary) catheter, a transvascular needle catheter, IC infusion and retrograde venous perfusion. One percutaneous route for a catheter is via a femoral artery traversing through and then across the aortic arch into the left ventricle. Imaging techniques can guide the catheter to the infarct region. The infarct region for example may be distinguished from healthy tissue using MRI techniques. A catheter having imported the MRI data may then be guided directly to the infarct region. The cellular component in this aspect of the present invention may act as a structurally reinforcing agent in the infarct zone 570. These cells add bulk to the area and replace the degraded myocytes that without replacement may normally lead to a thinning of the infarct regional wall. In turn, the viable cells release factors that may recruit other cells into the area for further reinforcement of the infarct zone.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to about 100 µL. In a preferred embodiment, the any of the described agents may be introduced in one or more doses in a volume of about 1 µL to about 50 µL. If an agent is introduced via an IV or an IC route the volumes may range from about 1 mL to about 500 mL.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485,481). The delivery device may include an apparatus for intracardiac drug administration, including a sensor for positioning within the heart, a delivery device to administer the desired agent and amount at the site of the position sensor.

Multiple Component Systems for Infarct Reconstruction
Component One

To prevent heart failure, it has been proposed that cardiomyocytes can be directly introduced into the infarct region to restore cardiac function cells of various origins, including embryonic and adult stem cells. One problem with this has been rejection by the host due to a rigorous immune response. In addition, the viability of tissue engineering for a myocardial infarct zone requires that oxygen and nutrient supplies are readily available, as well as a mode for removal of waste products from cell metabolism. The cells in these areas also need a supporting structure for adherence. The bioerodable gel with angiogenic agents previously discussed provides this later supporting structure. In the literature, it is known that the introduction of scaffolding with a bore size of less than 10 microns leads to a tightly fibrotic encapsulated scaffold with poor capillary in-growth. On the other hand as demonstrated, if the scaffolding pore diameter is around 20 microns, cellular encapsulation of the scaffold system is well perfused with capillary in-growth leading to fibrotic poor cellular rich region. One embodiment includes scaffolding that is introduced to the infarct zone and acts as a mechanical reinforcement. The force is distributed more evenly at the infarct region and ventricular remodeling is prevented.

In one embodiment, separate components are included to provide a network such as described above. One example is described in FIG. 6. A multi-component composition includes the first component including the previously illustrated bioerodable matrix or scaffolding 630. In this particular composition, the matrix (first component) provides a porous scaffolding to enhance capillary in-growth. The microparticles of the first component may be approximately 20 microns. In another embodiment, the first component of the composition may be introduced in a minimally invasive procedure such as percutaneously. A distal end of the catheter is advanced to the infarct zone and the bioerodable microparticles are released. In a further embodiment, the first component of the composition may be introduced via an intra-ventricular needle device to the infarct region. In a further embodiment, an intra-ventricular needle device including introducing multiple injections to the infarct region may introduce the first component of the composition. The first component may serve in one aspect as a domain to promote cell adhesion and growth (e.g α-1,3-galactosyltransferase (GGTA1) knockout cells). In addition, porosity may be controlled that leads to capillary in-growth. The first component may be a bioerodable microparticle with growth factor and angiogenic potential. The factor or other agent may release over a 1-2 week period. One embodiment may be that the first component includes PLGA 50:50 (previously described) with carboxylic acid end groups. An example of capillary in-growth to the domain provided by the first component may be facilitated by the release of angiogenic factors. One embodiment includes microparticles containing angiogenic factors that release rapidly after introduction to the infarct region. This tends to result in a rapid angiogenic response.

Biomaterials have been employed to conduct and accelerate otherwise naturally occurring phenomena, such as tissue regeneration in wound healing in an otherwise healthy subject; to induce cellular responses that might not normally be present, such as healing in a diseased subject or the generation of a new vascular bed to receive a subsequent cell transplant; and to block natural phenomena, such as the immune rejection of cell transplants from other species or the transmission of growth factor signals that stimulate scar formation in certain situations.

Component Two

A second component 640 of a multi component composition according to the method may be stimulating the heart using a device such as a pacemaker. A second component serves in one aspect to stimulate the cardiac function. On the other hand, it also serves to encourage unloading of the damaged area. It may be accomplished by introducing one or more leads, for example, to the infarct region. The scaffold may serve as a camouflage from the immune system for introduction of the microparticles to the infarct region. The electrical stimulation serves to unload the area and prevent remodeling. In addition, a cellular component may consist of a population that has an altered surface antigen to prevent immune recognition of α-1,3-galactosyltransferase (GGTA1) knockout cells. One embodiment includes the injection of both the growth factor containing microparticles and the cellular component (e.g., α-1,3-galactosyltransferase (GGTA1) knockout cells) using a dual bore needle. As the microparticles decompose, growth factors may be released promoting the capillary formation within the matrix. In addition, cells begin to grow in the infarct area. These cells release proteases that may result in the decomposition of the scaffolding, ultimately creating additional area for cellular in-growth. In addition, cells secrete their own extracellular matrix, the polymer degrades and the resulting tissue may eventually become a completely natural environment. The decomposition products may be cleared from the area by the renal system since capillary re-growth may occur.

Any one or more catheters may be used to deliver the any one or multiple components of the embodiments to the infarct region area including, but not limited to, a dual bore needle catheter. Several catheters have been designed in order to precisely deliver agents to a damaged region within the heart, for example, an infarct region. Several of these catheters have been described (U.S. Pat. Nos. 6,309,370; 6,432,119; 6,485,481). The delivery device may include an apparatus for intracardiac drug administration, including a sensor for positioning within the heart, a delivery device to administer the desired agent and amount at the site of the position sensor.

Multi Component System for Infarct Reconstruction and Infarct Reoxygenation

The progression of heart failure after an MI is a result of the remodeling of the heart after infarct. In the remodeling processes the heart becomes thinner and the diameter increases in response to a decrease in heart output, in an effort to maintain a continual cardiac output. This process of thinning results in an increase in the radius of the heart and the stresses on the heart increase.

It has been shown that perfluorocarbon compounds have a high affinity for gases, for example carbon dioxide and oxygen. The ability of perfluorocarbons to transport oxygen is approximately eighteen times greater than blood plasma in a comparable volume of each component. In addition, it was shown that the half-life for oxygenation/deoxygenation is approximately three and one half times faster for many perfluorinated compounds as compared to hemoglobin. Thus, perfluoro compounds may be used in tissues to aid in the reoxygenation of an affected region such as an infarct region. A few examples that demonstrate biocompatibility in a subject are identified in Table 1.

TABLE 1

| Compound | | Properties | | |
|---|---|---|---|---|
| Trade Name or Common Name | Chemical Name and Structure | Molecular Weight | Vapor Pressure (mmHg) | $O_2$ solubility at 37° C. (V %) |
| F-44E | 1,2-bis(perfluorobutyl)ethane $F_9C_4$—CH = CH = $C_4 F_9$ | 462 | 12.6 | 50 |
| F-66E or F-i66E | 1-perfluoropropane-2-erfluorohexyl)ethane $F_7C_3$—CH = CH = $C_6 F_{13}$ | 664 | 2.3 | 41 |
| FDC | Perfluorodecalin $C_{10}F_{18}$ | 462 | 12.5 | 45 |

In addition, any of the above detailed embodiments may be combined with electrical stimulation to unload the infarct region. Electrical stimulation may be used before 760, simultaneously 770 and/or after 780 treatment of reoxygenating compounds to an infarct region.

Figure 6:
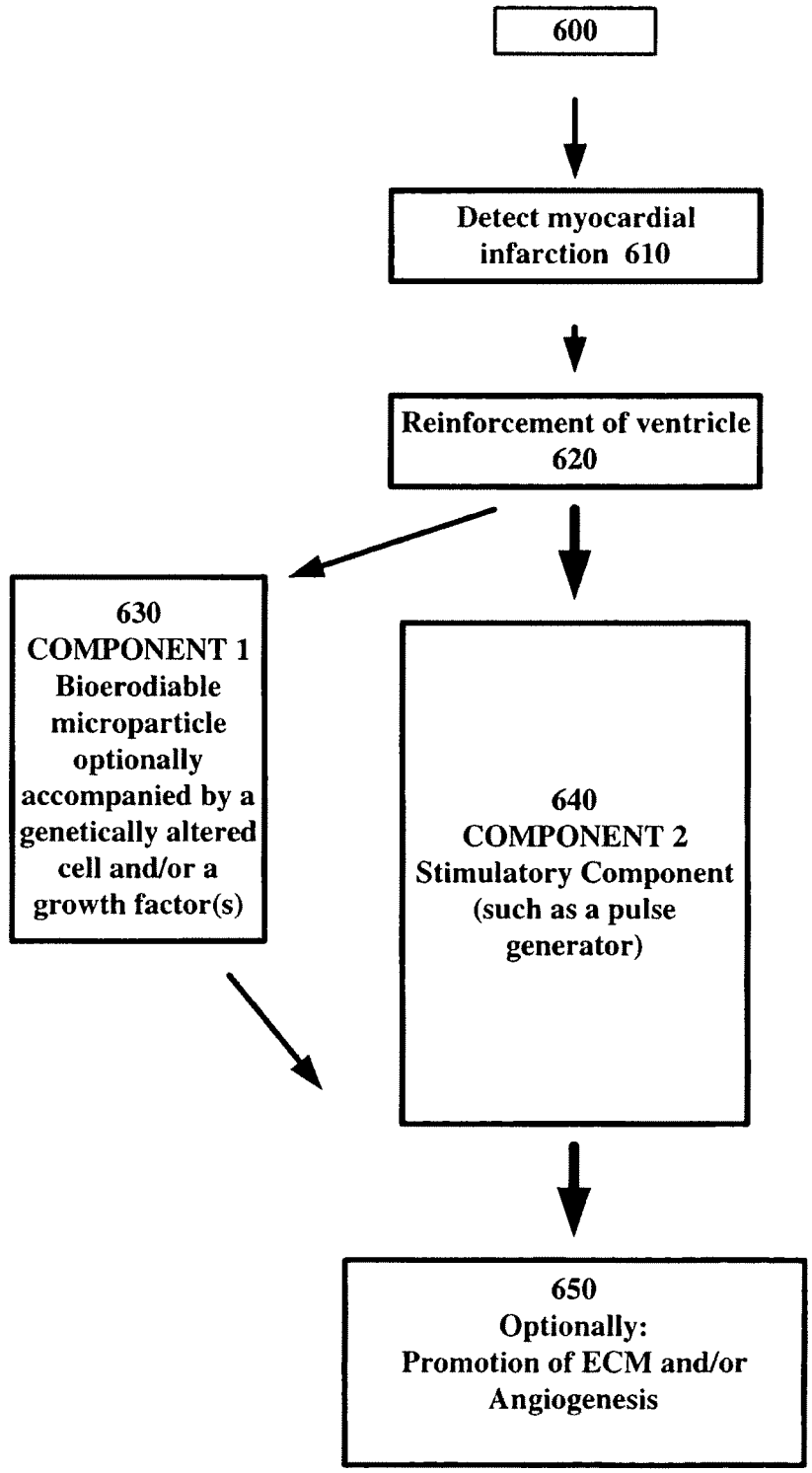
FIG. 6 illustrates an exemplary flow chart of stimulation of the heart combined with cellular replacement therapy in the infarct region.
Figure 7:
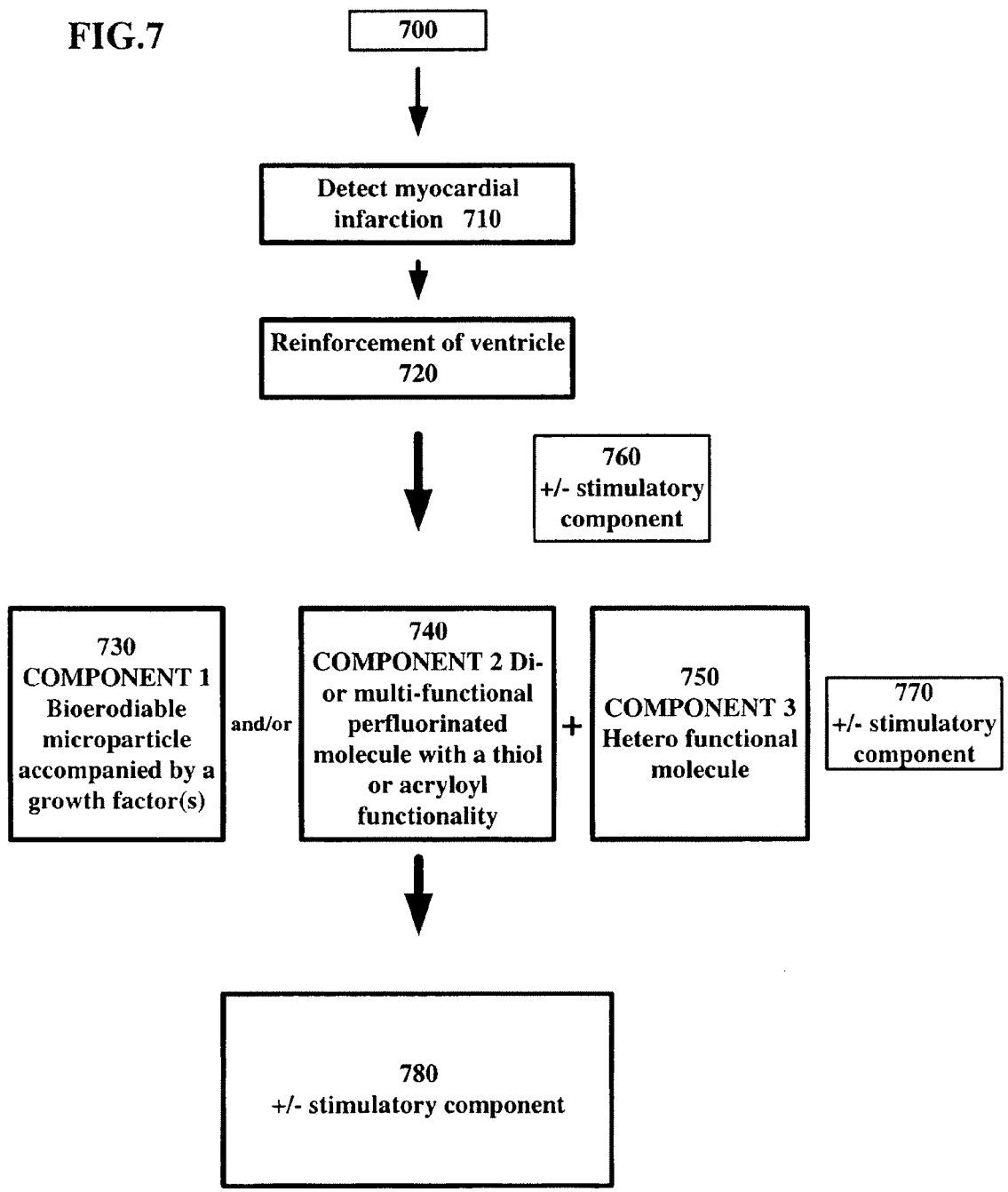
FIG. 7 illustrates a flowchart of introducing cellular compositions to the infarct region and stimulating the region with leads.
Figure 8:
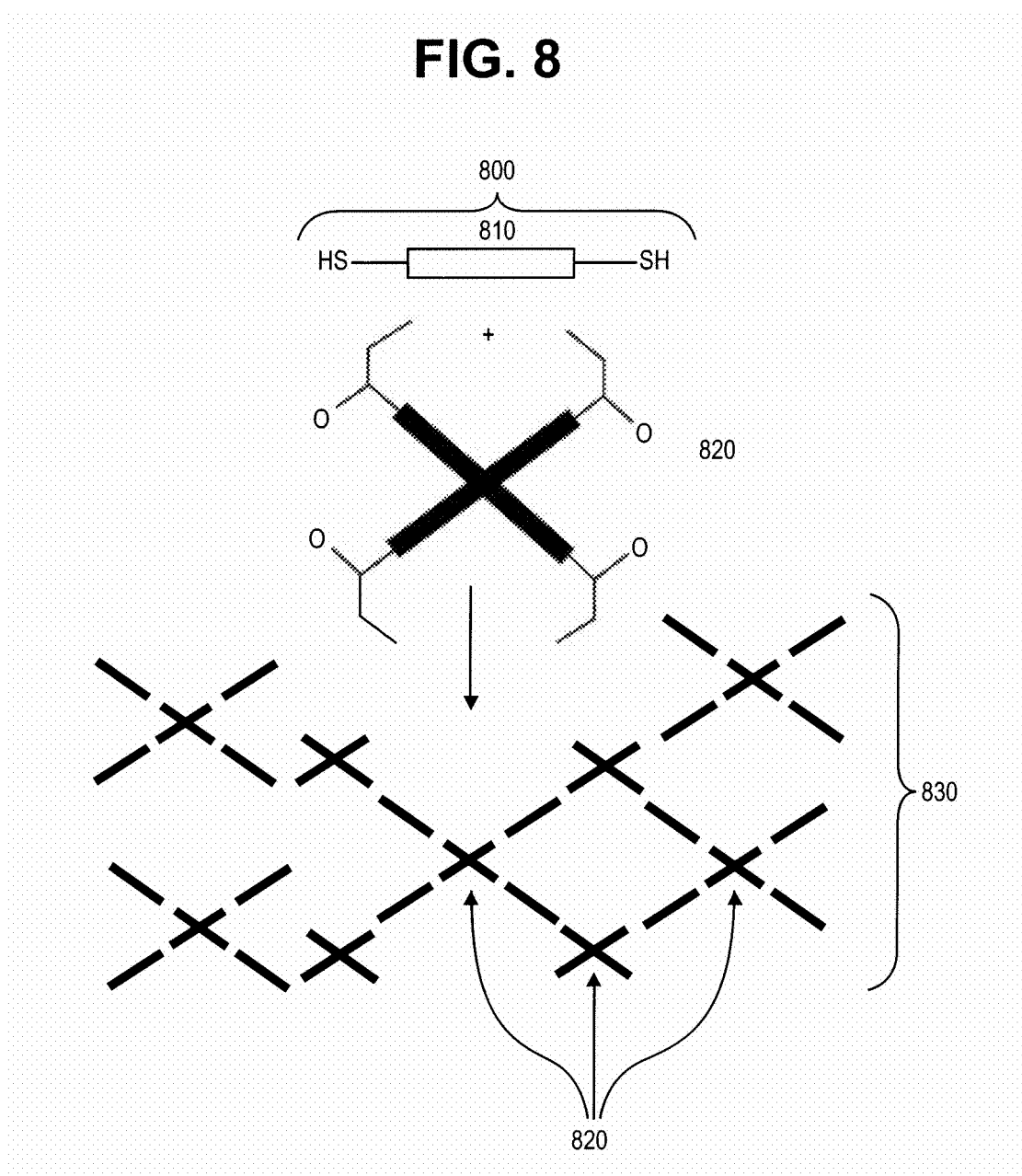
FIG. 8 illustrates a general structure of a first and of a second component that may form a scaffold-like structure for reinforcement in an infarct region.

FIG. 7 illustrates the multi-component system in a flowchart. The myocardial infarction is located 720. Then, the components are delivered to the region via a minimally invasive procedure by methods previously described and/or by catheter delivery. It was previously disclosed that the addition of a thiol functionality U.S. patent application Ser. No. 10/414,767. FIG. 6 component 3 in the presence of an electron deficient double bond, such as an acyloyl functionality FIG. 6 component 2, can undergo a Michael addition reaction. Under basic conditions a thiol functionality becomes hypernucleophilic and rapidly (<10 seconds) forms a bond with the acryloyl functionality. As illustrated in FIG. 6, a gel may be formed to prevent infarct expansion and/or bulking thus preventing a remodeling of the heart that may lead to heart failure. This may be combined with a stimulatory component FIG. 6 640 in this application to possibly unload the infarct region. FIG. 7 730 illustrates the first component that includes a bioerodable gel and 740 illustrates the gel accompanied by a perfluorinated compound as the second component to enhance oxygenation of the tissue. The gel is formed by a three-component system. The first component includes a biocompatible polymer as previously described with a multifunctional spacer group 730. The second component 740 includes a difunctional or multifunctional perfluorinated molecule 740. The third component 750 includes a heterofunctional molecule with a reactive functionality on one side of the spacer group, and a cell binding peptide sequence, such as the peptide sequences previously described, on the terminal end. One example of a peptide sequence includes an RGD sequence. This three-component system may be introduced to the infarct region by similar minimally invasive methods as described for the methods of FIG. 6 that may be guided by mapping the heart prior to administration of an agent. An electrical stimulus such as pulse-generating leads may be placed in or around the infarct region and may be used at any time during a gel reinforcement treatment to unload the region.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL. IV, and IC routes may be required which would involve larger treatment volumes (for example about 2 mL to about 250 mL).

An ester bond may be formed between a second component and a third component of a multi-component composition of, for example, FIG. 6. This bond is necessary for delaying the degradation of the scaffolding and release of the active agents within the microparticles. This bond tends to resist degradation for approximately 2 months.

Swellable Agent Systems For Reinforcement

One method for introduction of the microparticles is percutaneously with the use of a catheter. A distal end of the catheter may be advanced to the infarct region and the microparticles may be released. The microparticles become lodged in the infarct tissue. One embodiment includes the use of microparticle beads capable of fluid uptake in the infarct region to structurally reinforce the region. The particles will range in size from approximately 5 to approximately 10 microns. The microparticles will be less than 10 microns so that the completely swollen particle becomes lodged in the site but is not too large to become an obstruction in the area. In addition, the swollen microparticles provide mechanical strength and thickness to the damaged area by replacing the dead and degraded myocardial cells.

2. Agents a. Hydrogels Spheres

Examples include hydrogel spheres composed of cross-linked polyacrylamide or cross-linked PVP. The monomeric form of these products will contain di-functional monomers such as di-vinyl benzene, ethylene glycol dimethylacrylate or bis acrylamido acetic acid. These agents form a cross-linked network that is resistant to dissolution in aqueous systems.

b. Commercial Products

Several commercial products are available that may be used such as microparticles obtained from A.P. Pharma or Biosphere Medical. These microparticles resist non-specific protein absorption and have bio-stable backbone linkages. These microparticles are not bioerodable or bioabsorbable.

Structural Reinforcement Compositions and Materials

Several possible methods to reinforce the ventricular wall of the infarct region of an MI subject. Restraining the infarct zone by suturing an epicardial polymer mesh was previously demonstrated. See Kelley, S. T., et al., *Restraining Infarct Expansion Preserves Left Ventricular Geometry and Function After Acute Anteroapical Infarction*, Circ., 1999, pp. 135-142, 99. Due to the nature of this technique suturing the mesh directly into the tissue was necessary. This may cause further damage. This procedure requires invasive surgery. In addition, the polymer mesh does not degrade over time and this may also be a problem. By injecting a reinforcing agent directly into the affected area by minimally invasive procedures, this avoids the intrusive suturing protocol. The solution may be injected in the infarct zone during an open chest procedure. In one embodiment, the introduction of the reinforcing solution comprises the following procedures consisting of sub-xiphoid and percutaneously. In another embodiment, the mode of introduction of the reinforcing solution by a percutaneous injection comprises one of the following consisting of an intraventricular catheter, a transvascular needle catheter and retrograde venous perfusion.

3. Single Component Systems

One embodiment utilizes a single pseudoplastic or thixotropic material capable of forming a gel-like reinforcement to the infarct region wall. Several examples of these materials exist. In one embodiment, the structural reinforcing agent includes one of the following: hyaluronic acid, bovine collagen, high-molecular weight ultra-pure polyacrylamide and polyvinyl pyrrolidone.

In one specific embodiment of the present invention, the single component for structural reinforcement comprises bovine collagen dispersed with PMMA (polymethyl methylacrylate) beads. These beads may be manufactured under the trade name of ARTECOLL (Rofil Medical International, Breda, The Netherlands). PMMA is one of several cross-linked or highly insoluble microparticles. PMMA was discovered in the early 1900's and was used initially in dental prosthesis. Recently, it has been used in bone replacement of the jaw and hip. In addition, it has been used for artificial eye lenses, pacemakers and dentures. ARTECOLL™ has principally been used in filling folds and wrinkles of the face, augmenting lips, adjusting an irregular nose.

Possibly one of the most important features of the insoluble microparticles is the surface of the microparticles must be smooth to induce collagen deposition. A rough surface promotes macrophage activity while discouraging collagen deposition. The methods incorporate the use of smooth surface particles. The components may act as a substrate for endogenous collagen deposition. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. In one embodiment, the dispersing material includes one of the following group of microparticle materials consisting of PMMA (polymethyl methylacrylate), P(MMA-co BMA) (polymethyl methylacrylate-co butyl methyl acrylate), carbon microparticles (Durasphere), polystyrene, cross-linked acrylic hydrogels and PLGA. In another embodiment, the cross-linked acrylic hydrogel may include the following HEMA (2-hydroxyethyl methacrylate), AA (acrylic acid), AMPS (acrylamido-methyl-propane sulfonate), acrylamide, N,N, di-methyl acrylamide, diacetone acrylamide, styrene sulfonate, and di- or tri-functional monomers. The di or tri-functional monomers may be EGDMA (ethylene glycol dimethacrylate) and DVB (di-vinyl benzene). In addition, the use of highly crystalline (and hydrolysis resistant) PLGA microparticles may outlast the carrier gel and also provide a useful substrate for collagen deposition.

Another single solution introduced to the infarct zone may be hyaluronic acid dissolved in sodium salt in water. This is a manufactured gel sold as a dermal augmentation gel (RESTYLANE™). Hyaluronic acid hydrogel has also been used in the past for control of delivery of therapeutic agents in wound sites. See Luo, Y., et al., *Cross-linked Hyaluronic Acid Hydrogel Films: New Biomaterials for Drug Delivery*, Journal of Controlled Release, 2000, pp. 169-184, 69. Other possible single introduced components include bovine collagen (ZYDERM™ or ZYPLAST™), another dermal augmentation gel developed by Collagen Corp. The high molecular weight, ultrapure polyacrylamide in water may be FORMACRYL™ or BIOFORM™ other dermal augmentation gels. The bovine collagen may be dispersed by the PMMA product ARTECOLL™. ARTECOLL™ is best known for its success as a biocompatible dermal augmentation gel for reconstruction. RESOPLAST™ (Rofil Medical International, Breda, The Netherlands) may also be used as a single component gel.

In another embodiment, a reactive single component includes a component that is temperature sensitive. One example of this type of component is a component that may be a liquid at room temperature and once exposed to a temperature approximately equal to body temperature the component gels. A more specific component includes introducing block co-polymers of silk protein-like sub units and elastin-like sub units. An example of the block co-polymer synthetic protein may be ProLastin (PPTI, Protein Polymer Technologies). These components gel due to non-covalent interactions (hydrogen bonding and crystallization of silk-like subunits) at elevated temperatures for example approximately equal to body temperature. With these components, no lysine residues are present, so cross-linking due to endogenous lysyl oxidase does not occur. The formation of the gel via a change in temperature may be adjusted using additives. These additives include but are not limited to sodium chloride, Diglyme (Diethylene Glycol Dimethyl Ether; 2-Methoxyethyl Ether; Bis (2-Methoxy Ethyl Ether), and ethanol.

Many thermal reversible materials may be used for reinforcement of the myocardial tissue. Generally, thermal reversible components at temperatures of approximately 37 degrees Celsius and below are liquid or soft gel. When the temperature shifts to 37 degrees Celcius or above, the thermal reversible components tend to harden. In one embodiment, the temperature sensitive structurally reinforcing component may be Triblock poly (lactide-co-glycolide)-polyethylene glycol copolymer. This is commercially available (REGEL™ Macromed, Utah). In another embodiment, the temperature sensitive structurally reinforcing component may include the following consisting of poly (N-isopropylacrylamide) and copolymers of polyacrylic acid and poly (N-isopropylacrylamide). Another temperature sensitive structurally reinforcing component commercially available is PLURONICS™ (aqueous solutions of PEO-PPO-PEO (poly(ethylene oxide)-poly (propylene oxide)-poly(ethylene oxide) tri-block copolymers BASF, N.J.). See Huang, K., et al., *Synthesis and Characterization of Self-Assembling Block copolymers Containing Bioadhesive End Groups*, Biomacromolecules, 2002, pp. 397-406, 3. Another embodiment includes combining two or more of the single components in order to structurally reinforce the infarct region. For example, silk-elastin, collagen and Laminin may be used as a one-part system. The silk-elastin would likely form in situ cross-links due to the silk blocks.

In another embodiment, a reactive single component includes a component that is pH sensitive. The component remains in a liquid state if it is sufficiently protonated preventing gelation. In another embodiment, the component is initially maintained at a low pH for example pH 3.0 and later introduced to the treatment area which results in gelation of the component due to the physiological pH of the environment. Several possible cationic agents may be but are not limited to one of the following cationic agents that remain protonated at low pH, poly (allyl amine), DEAE-Dextran, ethoxylated Poly(ethylenimine), and Poly(lysine). Other examples may one of, but are not limited to, the following anionic agents: dextran sulfate, carboxymethyl dextran, carboxymethylcellulose, polystyrene sulfanate and chrondroitin sulfate.

Additionally, any of these microparticle components may be accompanied by one or more contrast agent and/or suitable agent(s) for treatment of the region. The contrast agent or treatment agent may be conjugated to or dissolved into the structural component prior to introduction to the infarct area. The agents that may accompany the reinforcing component(s) may include but are not limited to angiogenic agents, ACE inhibitors, angiotensin receptor blockers, SRCA (sercoplasmic reticulum calcium pump) pump increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. A conserved region of a peptide may be a sequence of amino acids having a special function of identification that has been conserved in a protein family over time. Another embodiment includes the use of a specific peptide conjugate with a conserved RGD (arginine (R)-glycine(G)-aspartic acid (D)) motif in the presence of the reinforcing component. In further embodiments, the RGD motif peptide may include the following: von Willebrand factor, osteopontin, fibronectin, fibrinogen, vitronectin, laminin and collagen. One embodiment seeks to minimize thinning during remodeling of the infarct region. Thus, bulking and reinforcing the infarct region post-MI may preserve the geometry of the ventricle.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485,481). The delivery device may include an apparatus for intracardiac drug administration, including a sensor for positioning within the heart, a delivery device to administer the desired agent and amount at the site of the position sensor.

Dual Component Systems

Dual component systems for the formation of structurally reinforcing gels for application to the infarct region may be used. Initially, the infarct region is identified by imaging methods previously discussed. In one example, two components are combined at the infarct zone at around physiological pH. Component one is a principally anionic solution and the second component is principally a cationic solution at approximately physiological pH. When the two components are mixed together at the infarct zone, a gel forms rapidly and irreversibly. In one embodiment, a dual component system may comprise poly (acrylic acid) as a first component and poly (allyl amine) as a second component. In another embodiment, a dual component system may comprise poly (acrylic acid) as a first component and poly (allyl amine) as a second component that may be delivered by a catheter with dual injection lumens. Other dual component systems to form a structurally reinforcing gel in the infarct region may include elastin as a first component and lysyl oxidase as a second component; sodium alginate as a first component and an aqueous solution of calcium chloride as a second component, and tropoelastin and collagen as a first component and cross-linker lysyl dehydrogenase as a second component and laminin may be added to this combination later. The composition of each component will depend on the mechanical property of the final cross-linked system. Other substances that can replace the lysyl dehydrogenase or complement its cross-linking ability might be used such as glutaraldehyde, and/or photoactivatable crosslinkers for example blue dye used to cross-link. Additionally, these dual component systems may be combined with other individual system utilizing commercial products such as AVITENE™ (Microfibrillar Collagen Hemostat), SUGICEL™, (absorbable haemostat, Johnson & Johnson), GELFOAM™, FLOSEAL™ (Baxter, matrix hemostatic sealant with a granular physical structure and thrombin), FOCAL SEAL™ (Focal, Inc.) or FIBRIN SEAL™ (FS). FLOSEAL™ is a gel constituting collagen derived particles and topical thrombin capable of being injected. It has been approved for uses including vascular sealing. Several other possible cationic agents may be but are not limited to one of the following cationic agents that remain protonated at low pH, poly (allyl amine), DEAF-Dextran, ethoxylated Poly(ethylenimine), and Poly(lysine). Other examples may be one of but are not limited to the following anionic agents: dextran sulfate, carboxymethyl dextran, carboxymethylcellulose, polystyrene sulfonate and chrondroitin sulfate. In a preferred embodiment, the first material may be DEAE Dextran and the second material may be polystyrene sulfonate.

One dual component system may use DOPA (3,4-dihydroxyphenyl-L-alanine), a principle component responsible for mussel adhesive proteins, capable of forming a hydrogel in conducive conditions. Specifically, a component known as star block DOPA-block-PEG undergoes cross-linking in situ forming the hydrogel after an oxidation process converts the DOPA to O-quinone. This process forms a stable in situ hydrogel. A specific embodiment may include the use of PEG triacrylate as a first component and PEG thiol as a second component introduced to the infarct zone via a dual lumen needle system discussed previously. A glue-like component system may be employed. One embodiment may include the use of GRF glue that is made up of gelatin, resorcinol and formaldehyde (GRF) as a structurally reinforcing agent introduced to the infarct zone. To accomplish this, a two-part system may be used to induce cross-linking upon admixture of the components at the infarct zone. In other embodiments, the following structurally reinforcing components may be added along with GRF comprising the group consisting of the cross-linking agents polyglutamic acid, polylysine and WSC (water soluble carbodimides).

A single pseudoplastic or thixotropic agent may be introduced to an infarct region in multiple injections and to structurally reinforce the wall. These agents are introduced in final form and require no additional agents. Multiple injections each at a different site that requires an endogenous component or a temperature change to convert to a structurally reinforcing form may be used. The structurally reinforcing agent(s) is localized to the infarct region via minimally invasive procedures discussed previously.

In addition, biocompatible viscosifiers for example type 1 gels may be added in combination with any of the single or multiple component systems illustrated. In addition electrical stimuli may be applied at any time of treatment to unload the infarct region. In one example, hyaluronic acid or PVP may be used to increase the resistance of the active formula from natural degradation once introduced to the infarct zone. In one embodiment the viscosity of the treatment agent may be about 0-100 centipoise. In other embodiments, the viscosity of the treatment agent may be about 0-50 centipoise. In a preferred embodiment, the viscosity of the treatment agent may be about 25-40 centipoise. In a preferred embodiment, the viscosity of the treatment agent may be about 35 centipoise.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL. IV, and IC routes may be required which would involve larger treatment volumes (for example about 2 mL to about 250 mL).

Biocompatible dyes may be added to any single or combination components of any of the described embodiments to trace the components in the infarct region in any procedure. Other dyes may be added for experimental purposes to trace the deposition of any agent for example in a rat heart. Some examples of these dyes include but are not limited to Sudan Red B, Fat Brown RR, Eosin Y and Toluidine blue.

On the other hand, tissue adhesive components may also be added in combination with any of the single or dual component systems. For example, Laminin-5, polyacrylic acid, Chitosan and water soluble chitosan may be used to increase the tissue retention of the active formulation. Laminin-5 is a basement membrane extracellular matrix macromolecule that provides an attachment substrate for both adhesion and migration in a wide variety of cell types, including epithelial cells, fibroblasts, neurons and leukocytes. Chitosan is the only natural positive ion polysaccharide obtained from deacetylated chitin. It possesses decomposability, good membrane forming state, biocompatibility, anti-fungal and anti-tumor function. Chitosan has excellent viscosity, compressibility and fluidity.

Single Components Suspended in a Delivery Medium

As with several of the previously discussed methods, other methods provide a bulking or structurally reinforcing agent to the infarct region. An agent comprising microparticles in solution (a dispersion) may be introduced to the infarct region after identification of the infarct region as described previously. The microparticles may be a predetermined range of about 1 to about 200 microns. In one embodiment, the microparticles may be 20 microns or less. In a preferred embodiment, the microparticles may be 10 microns or less. The microparticle size delivered to an infarct region may be determined by the delivery method used. For example an intraventricular catheter may be used to deliver particles up to 200 microns that may avoid the risk of an embolism. One suspending solution for the microparticles may be water. On the other hand, the suspending solution may also be a solvent, for example, dimethylsulfoxide (DMSO) or ethanol adjuvants. In one embodiment, a suspending solution along with the microparticles may be introduced to as a dispersion to an infarct region and the microparticles remain in the region as the solution dissipates into the surrounding tissue. Thus, the microparticles provide a structurally reinforcing bulk to the region. This may result in reduction of stress to the post infarct myocardium. It may also serve as a substrate for additional site for collagen deposition. In one embodiment, the dispersion (detailed above) may be injected in to the infarct zone during an open chest procedure via a minimally invasive procedure. In another embodiment, the minimally invasive procedure includes at least one of subxiphoid and percutaneously. In another embodiment, the percutaneous introduction into the infarct zone may include one of intra-ventricular needle, transvascular catheter and retrograde venous perfusion.

Several examples of gels that may be used in any embodiment herein exist such as the viscous liquid sucrose acetate isobutyrate (SAIB). SAIB is water insoluble. SAIB may be dissolved in a solvent or a combination of solvents, for example, ethanol, dimethylsulfoxide, ethyl lactate, ethyl acetate, benzyl alcohol, triacetin, 2-pyrrolidone, N-methyl pyrrolidone, propylene carbonate or glycofurol. These solvents decrease the viscosity of SAIB in order to facilitate the introduction of this agent through a needle or lumen. In one embodiment, AIB may be introduced accompanied by a solvent to the infarct region and the solvent dissipates at the site leaving behind the viscous SAIB in the region. In another embodiment, a SAIB treated infarct region may be accompanied by an electrical stimulus such as a pulse generator to unload the area before, during or after treatment with SAIB.

Other biocompatible polymer systems may be introduced to an infarct zone. Some of these agents are not only biocompatible but also substantially water insoluble similar to SAIB. Solvents or mixtures of solvents may be used to dissolve the polymer in order to facilitate introduction to the infarct zone. In one embodiment, a biocompatible water insoluble polymer may include the following consisting of polylactides, polyglycolides, polycaprolactones, polyanhydrides, polyalkylene oxates, polyamides, polyurethanes, polyesteramides, polydioxanones, polyhydroxyvalerates, polyacetals, polyketals, polycarbonates, polyorthoesters, polyphosphazenes, polyhydroxybutyrates, polyalkylene succinates, and poly(amino acids). Any one of these insoluble polymers may be dissolved in solvents for example Diglyme, dimethyl isosorbide, N-methyl-2-pyrrolidone, 2-pyrrolidone, glycerol, propylene glycol, ethanol, tetraglycol, diethyl succinate, solketal, ethyl acetate, ethyl lactate, ethyl butyrate, dibutyl malonate, tributyl citrate, tri-n-hexyl acetylcitrate, dietyl glutarate, diethyl malonate, triethyl citrate, triacetin, tributyrin, diethyl carbonate, propylene carbonate acetone, methyl ethyl ketone, dimethyl sulfoxide dimethyl sulfone, tetrahydrofuran, capralactum, N,N-diethyl-m-toluamide, 1-dodecylazacycloheptan-2-one, 1,3-dimethyl-3,4,5,6-tetrahydro-2(1H)-pyrimidinone and glycerol formal to form an injectable polymer solution. The dispersion may be introduced into the infarct region of the heart where the solvent may dissipate and the polymer may precipitate out of the dispersion to structurally reinforce the infarct regional wall. In one embodiment, the disclosed polymers may be used in any combination as co-polymers of two or more polymers introduced to the infarct region.

Another possible reinforcing agent may include the use of a vinyl polymer and acrylate biocompatible polymer system. Once injected into an infarct zone, the vinyl polymer/acrylate agent contacts water and the polymer precipitates thus reinforcing the surrounding tissue of the infarct region. In one embodiment, the vinyl polymer/acrylate agent includes the following such as polyvinyl butyral, PBMA-HEMA, PEMA-HEMA, PMMA-HEMA and other acrylate copolymers that dissolve in ethanol, acetone and I-PA. In another embodiment, the vinyl polymer/acrylate agent introduced to the infarct region may be EVAL™ that has a solid phase or melt phase forming process. EVAL™ Resins have a high crystalline structure. Thermoforming grades of EVAL™ resins have monoclinic crystalline structure while most polyolefins have either a hexagonal or orthorhombic type structure. This characteristic provides flexibility within its thermoforming capabilities. In another embodiment, the vinyl polymer/acrylate agent introduced to the infarct region may be BUTVAR™ (polyvinyl butyral). In one embodiment, the agent may be P(BMA co-MMA) (Aldrich Chem.) in Diglyme. In another embodiment, the agent may be EVAL™, a co-polymer of ethylene and vinyl alcohol (EVAL Co. of America, Houston, Tex.) in dimethyl acetamide. In another embodiment, the polymer may be PLGA (poly(lactide co-glycolide) (Birmingham Polymers, Birmingham, Ala.) in Diglyme.

Other components may act as a substrate for endogenous collagen deposition and protect the precipitated or remaining microparticles from erosion. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. The dispersed material includes the following group of microparticle materials: PMMA, P(MMA-co BMA), carbon microparticles (Durasphere), poly styrene, cross-linked acrylic hydrogels and PLGA. In another embodiment, the cross-linked acrylic hydrogel may include the following for example HEMA, AA, AMPS, acrylamide, N,N, di-methyl acrylamide, diacetone acrylamide, styrene sulfonate, and di or tri functional monomers. The di or tri-functional monomers may be EGDMA and DVB. Another example of durable microparticles includes pyrolytic carbon-coated microparticles. One example of pyrolytic carbon-coated microparticles was originally produced for urinary incontinence (Carbon Medical Technologies) and trisacryl gelatin microparticles for use as embolization particles (Biosphere). In addition, the use of highly crystalline (and hydrolysis resistant) PLGA microparticles may outlast the carrier gel and also provide a useful substrate for collagen deposition.

One or more contrast agents 1540 and/or suitable treatment agent(s) 1550 may accompany the previously detailed components as a treatment of the infarct region. The contrast agent or treatment agent may be conjugated to or dissolved into the structural component prior to introduction to the infarct area. The contrast agents may be used for detection in X-ray or MR analysis. The agents that may accompany the reinforcing component(s) may include but are not limited to angiogenic agents, ACE inhibitors, angiotensin receptor blockers, SRCA pump (sarcoplasmic reticulum calcium pump) increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD (arginine-glycine-asparagine) motif in the presence of the reinforcing component. In further embodiments, the RGD motif peptide may include von Willebrand factor, osteopontin, fibronectin, fibrinogen, vitronectin, laminin and collagen.

In one embodiment, any of the described agents may be introduced in one or more doses in a volume of about 1 µL to 1 mL. In another embodiment, any of the described agents may be introduced in one or more doses in a volume of about 1 µl to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL.

Additionally, any one of these agents may be accompanied by one or more contrast agent and/or suitable agent(s) for treatment of the region. The contrast agent or treatment agent may be conjugated to or dissolved into the structural component prior to introduction to the infarct area. The agents that may accompany the reinforcing component(s) may include but are not limited to angiogenic agents, ACE inhibitors, angiotensin receptor blockers, SRCA pump increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD (arginine-glycine-aspartic acid) motif in the presence of the reinforcing component. In further embodiments, the RGD motif peptide comprises the following: von Willebrand factor, osteopontin, fibronectin, fibrinogen, vitronectin, laminin or collagen.

Prevention of Myocardial Edema and "Cementing" of the Infarct Region

One of the initial responses of the process post-MI is myocardial edema. The edema is composed of extravasated blood evident within a few hours after infarction. This is followed by its dissolution within the next few hours. The process that occurs immediately post-MI is that the infarct regional wall thickens and then it thins. The present invention introduces one or more clotting factors to the region thereby "cementing" the now clotted blood to reinforce the wall and thicken the wall. One method to clot the blood may use a dual solution technique. In one embodiment, the first solution includes calcium chloride and thrombin and the second solution may include fibrinogen and transexamic acid. Transexamic acid is an anti-fibrinolytic agent. The introduction of these two solutions to the infarct region sequentially result in localized clotting of the blood that forms a structurally reinforcing mass within the region preventing thinning of the infarct site. In another embodiment, intra-venous pressure perfusion may be used to deliver the clot inducing solutions to the infarct zone. This prevents the possibility of the clot releasing into the arterial circulation. Another possible component for promoting clotting may be the use of shear-activated platelet fraction to induce localized clotting. This platelet fraction may be isolated from the MI subject's own blood or another source. Other factors encompass factors that are termed intrinsic and extrinsic factors. Intrinsic factors initiate clotting in the absence of injury. Extrinsic factors initiate clotting that is caused by injury. In one embodiment, the clotting factor used to cease myocardial edema and reinforce the ventricular wall at the infarct zone may comprise the following: von Willebrand Factor (vWF), High Molecular Weight Kininogen (HMWK), Fibrinogen, Prothrombin, or Tissue Factors III-X. In another embodiment of the present invention, any combination of the clotting factors mentioned previously may be used that may provide increased tensile strength the infarct regional wall.

Matrix Metalloproteinase Inhibitors Use in the Infarct Region

After an MI injury occurs macrophages tend to infiltrate the infarct region. The macrophages release matrix metalloproteinases (MMPs). As members of a zinc-containing endoproteinase family, the MMPs have structural similarities but each enzyme has a different substrate specificity, produced by different cells and additionally have different inducibilities. These enzymes cause destruction in the infarct zone. One important structural component destroyed by MMPs is the extracellular matrix (ECM). The ECM is a complex structural entity surrounding and supporting cells that are found within mammalian tissues. The ECM is often referred to as the connective tissue. The ECM is composed of 3 major classes of biomolecules: structural proteins, for example, collagen and elastin; specialized proteins, for example, fibrillin, fibronectin, and laminin; and proteoglycans. These are composed of a protein core to which is attached long chains of repeating disaccharide units termed of glycosaminoglycans (GAGS) forming extremely complex high molecular weight components of the ECM. Collagen is the principal component of the ECM and MMP induce ECM degradation and affect collagen deposition. Inhibitors of MMP(s) exist 1970 and some of these inhibitors are tissue specific. It was previously demonstrated that acute pharmacological inhibition of MMPs or in some cases a deficiency in MMP-9 that the left ventricle dilatation is attenuated in the infarct heart of a mouse. See Creemers, E., et al., *Matrix Metalloproteinase Inhibition After Myocardial Infarction, A New Approach to Prevent Heart Failure?*, Circ. Res., 1994, pp. 2315-2326, 89(5). The inhibitors of MMPs are referred to as tissue inhibitors of metalloproteinases (TIMPs). Synthetic forms of MMPIs also exist for example BB-94, AG3340, Ro32-355b and GM 6001. It was previously shown that MMPIs reduce the remodeling in the left ventricle by reducing wall thinning. These experiments were performed on rabbits. In addition, this study also demonstrated that MMPI increases rather than decreases neovascularization in the subendocardium. See Lindsey, et al., *Selective matrix metalloproteinase inhibitors reduce left ventricle remodeling but does not inhibit angiogenesis after myocardial infarction*, Circulation, Feb. 12, 2002, pp. 753-8, 105(6). In the one embodiment MMPIs may be introduced to the infarct region to delay the remodeling process by reducing the migration of fibroblasts and deposition of collagen and prevent ECM degradation, reduce leukocyte influx and also reduce wall stress. In one embodiment, the MMPIs may include the following TIMPs including, but not limited to, TIMP-1, TIMP-2, TIMP-3 and TIMP-4 introduced to the infarct region in combination with introducing any of the described structurally reinforcing agents to the infarct region. In another embodiment, naturally occurring inhibitors of MMPs may be increased by exogenous administration of recombinant TIMPs. In another embodiment, the MMPI comprises a synthetically derived MMPI introduced to the infarct region in combination with the introduction of any of the described structurally reinforcing agents and/or applied stimulating devices (e.g., PG) to the infarct region. The introduction of MMPIs to the infarct zone may be accomplished by several different methods. It is critical that the introduction of these MMPI agents be accomplished by a minimally invasive technique. In one embodiment, MMPI agents will be introduced to the region by a minimally invasive procedure to prevent ECM degradation. An agent or dispersion will be introduced in one embodiment by multiple injections to the infarct region. This results in prevention of ECM degradation and increased strength to the regional wall. In one embodiment, the MMPI agent may be injected in to the infarct zone during an open chest procedure via a minimally invasive procedure. In another, the minimally invasive procedure may include one of sub-xiphoid and percutaneous methods. In another embodiment, the percutaneous introduction into the infarct zone may include one of intra-ventricular needle, transvascular needle catheter and retrograde venous perfusion. In addition, the MMPI agents may be introduced via suspension or sustained release formula, for example, introduced in microparticles.

Structural Reinforcement of the Infarct Zone by Inducible Gel Systems

Photo-polymerizable hydrogels have been used before in tissue engineering applications. These gels are biocompatible and do not cause thrombosis or tissue damage. These hydrogels may be photo-polymerized in vivo and in vitro in the presence of ultraviolet (UV) or visible light depending on the photo initiation system. Photo-polymerizing materials may be spatially and temporally controlled by the polymerization rate. These hydrogels have very fast curing rates. A monomer or macromer form of the hydrogel may be introduced to the infarct zone for augmentation with a photo initiator. Examples of these hydrogel materials include PEG acrylate derivatives, PEG methacrylate derivatives or modified polysaccharides.

Visible light may be used to initiate interfacial photopolymerization of a polyoxyethylene glycol (PEG)-co-poly(alpha-hydroxy acid) copolymer based on PEG 8000 macromonomer in the presence of an initiator, for example, Quantacure QTX. Initiator 2-hydroxy-3-(3,4,dimethyl-9-oxo-9H-thioxanthen-2-yloxy)N,N,N-trimethyl-1-propanium chloride photo-initiator may be obtained as Quantacure QTX. This is a specific water-soluble photo-initiator that absorbs ultraviolet and/or visible radiation and forms an excited state that may subsequently react with electron-donating sites and may produce free radicals. This technology has been used to demonstrate adherence to porcine aortic tissue, resulting in a hydrogel barrier that conformed to the region of introduction. The resulting matrix was optimized in vitro and resulted in the formation of a 5-100 microns thick barrier. See Lyman, M. D., et al., *Characterization of the formation of interfacially photopolymerized thin hydrogels in contact with arterial tissue Bioinaterials*, February 1996, pp. 359-64, 17(3). Scaffolding may be directed to only the desired area of the ventricle using minimally invasive procedures discussed previously. The structural reinforcement could remain in place until it is cleared or degrade.

One embodiment includes introduction to the infarct zone of benzoin derivatives, hydroxalkylphenones, benziketals and acetophenone derivatives or similar compounds. These photo-initiators form radicals upon exposure to UV light by either photocleavage or by hydrogen abstraction to initiate the reaction. The source of the UV or visible light may be supplied by means of a catheter, for example, a fiber optic tip catheter or lead on a catheter, or, transdermally as described. A catheter assembly may be used to deliver a light sensitive material. The catheter is designed to provide a delivery device with at least one lumen for one or more agent(s) and a light source for modification of the delivered agent. The catheter controller may house a switch for the light source and a controller for agent deliver. In another embodiment, the photo-initiator Camphorquinone may be used. Camphorquinone has been used extensively in dental applications and has a $\lambda_{max}$ of 467 nanometers. For example, this agent can be activated by a GaN blue LED on the tip of a catheter. One embodiment includes the use of visible light at the end of the delivery catheter to induce the polymerization event in the presence of a light sensitive initiator. Another embodiment includes the use of the photoinitiator, Camphorquinone that may facilitate the cross-linking of the hydrogel by a light on the tip of a catheter within the infarct region. Another embodiment includes the use of the photoinitiator, Quanticare QTX that may facilitate the cross-linking of the hydrogel by a light on the tip of a catheter within the infarct region. Another embodiment includes the use of a catheter with a UVA light source to induce the polymerization event in the presence of a light sensitive initiator. Other initiators of polymerization in the visible group include water soluble free radical initiator 2-hydroxy-3-(3,4,dimethyl-9-oxo-9H-thioxanthen-2-yloxy) N,N,N-trimethyl-1-propanium chloride. This cascade of events provides the necessary environment for initiation of polymerization of suitable vinyl monomers or pre-polymers in aqueous form within the infarct region. See Kinart, et al., *Electrochemical studies of 2-hydroxy-3-(3,4-dimethyl-9-oxo-9H-thioxanthen-2-yloxy)N,N,N-trimethyl-1-propanium chloride*, J. Electroanal. Chem., 1990, pp. 293-297, 294).

In one embodiment the photo-polymerizable material may be introduced to the infarct regions during an open chest procedure or via a minimally invasive procedure. In another embodiment, the minimally invasive procedure includes sub-xiphoid and percutaneous methods. In another embodiment, the percutaneous introduction into the infarct zone may include one of the following: intra-ventricular needle; transvascular needle catheter; and retrograde venous perfusion. Any of these embodiments may include the use of electrical stimulation via leads for pulse generation in and/or around the infarct region. A single bore needle catheter may be used to introduce the photo-polymerizable material into the infarct zone. Once the agent is introduced to the region, several heartbeats clear the excess agent into the ventricle and this excess agent is cleared from the cardiac region. Once the excess material is cleared, the light source may be introduced to induce polymerization. Thus, the structural reinforcement is confined to the local area of damage where tissue augmentation is required. The scaffolding may be made up of a resistant material or a biodegradable material. Some examples of biodegradable materials include PEG-co-poly(α-hydroxy acid) diacrylate macromers, derivatives of this material that vary the length and composition of the α-hydroxy acid segment in the co-polymer, poly(propylene fumarate-co-ethylene glycol and hyaluronic acid derivatives. The degradation rates of the polymers may be varied according to the optimum length of time the material is required to remain in the infarct region. It has been shown that the degradation rates of theses gels can be modified by the appropriate choice of the oligo(α-hydroxy acid) from as little as less than one day to as long as 4 months. See Sawhney, A. S., et al., *Bioerodable Hydrogels Based on Photopolymerized Poly(ethylene glycol)-co-poly(α-hydroxy acid)+Diacrylate Macromers*, Macromolecules. 1993, pp. 581-587, 26. Any of these polymer chains may be formed in the presence of a photoinitiator, such as Quantacure QTX, and a light source.

In one embodiment, any of the described agents may be introduced in one or more doses in a volume of about 1 μL to 1 mL. In another embodiment, any of the described agents may be introduced in one or more doses in a volume of about 1 μL to 300 μL. In another embodiment, any of the described agents may be introduced in one or more doses in a volume of about 1 μL to 100 μL. In a preferred embodiment, the any of the described agents may be introduced in one or more doses in a volume of about 1 μL to 50 μL.

One way to introduce dual components to an infarct region is by using a catheter device. This avoids the possibility of injecting the agents into the exact same site. The delivery device of U.S. patent application Ser. No. 10/414,602, incorporated herein, may be used to deliver the components to the infarct region. The infarction is a region between the endocardium and the epicardium. The device is advanced to a site and the first component is delivered by extending a first needle. The component is thereby dispersed in the infarct area. Then, this first needle is retracted while the second needle is extended. The second component is dispersed. The delivery of the two components to the area may be capable of forming a gel, or, may be two separate components.

FIG. 9A-9E illustrates the introduction of several components to the infarct region 910 to treat an MI. One embodiment may be the introduction of a first component 920, for example, microparticles harboring a growth factor 940. Then, a second component 930 such as cells or a structurally reinforcing agent, is introduced through a dual bore needle (FIGS. 9C and 9D 950). FIG. 9E illustrates a schematic of the release of growth factor from the degrading microparticles 925. Optionally, a cellular component such as a knockout porcine heart cell may also be introduced to the area. The thiol-containing component 905 may be used to decrease the rate of decomposition of the scaffold and control release of the fibroblast recruiting components of the microparticles. A further optimal treatment includes the use of electrical stimulation around the infarct region as described above in conjunction with any combination of other components shown in FIG. 9A-9E.

Ventricular Plugs

Another method for reinforcing the damaged wall of a ventricle may include introduction of a solid material to the damaged area. The solid material may be used to fill or bulk the region by introducing plugs of the solid material to the site and may increase the compliance of the ventricle. These materials may be made of organic or silicon-based polymers, biodegradable polymers, non-biodegradable polymers, engineered biomaterials and/or metals. In one embodiment the plug may have barbs or pointed ends in order to lodge the material into the area and ensure it remains there. In other embodiments, the sealant or plug may add bulk to the thinning wall of an infarct post myocardial infarction. This may result in an increase in the modulus of elasticity of the damaged area. In other embodiments, the sealant or plug may invoke an inflammatory response to the infarct region. The inflammatory response will result in the increase in angiogenic response capable of causing recruitment and activation of fibroblasts that deposit additional collagen to bulk the thinning infarct region and increase the modulus of elasticity of this region. Still, other embodiments include the addition of a plug to the damaged region of a ventricle that may add strength to the wall and also cause an inflammatory response to the region.

In one embodiment, the plug supplied to the damaged region of the ventricle may include biocompatible organic components. In other embodiments, the plug supplied to the damaged region of the ventricle may include a biocompatible silicone-based polymer. In other embodiments, the plug supplied to the damaged region of the ventricle may include biocompatible biodegradable polymers for example PLGA, Poly(hydroxyvalerate) and poly ortho esters etc. In other embodiments, the plug supplied to the damaged region of the ventricle may include biocompatible non-biodegradable material for example polypropylene and PMMA. In still further embodiments, the plug supplied to the damaged region of the ventricle may include biocompatible metal compounds, for example, 316 L, Co—Cr alloy, tantalum and titanium. Another advantage to using a plug directly implanted in the region of interest may be to add additional surface components to the plug such as side groups. These side groups may contain reactive side groups that react with exogenously supplied or endogenous collagen, for example type I and type III collagen. Since collagen contains a significant number of lysine and hydroxyproline residues, these residues harbor primary amine and hydroxyl groups capable of reacting with other moieties. In one embodiment, the plug supplied to the damaged region of the ventricle may include surface aldehyde groups capable of reacting with the primary amines of lysine in collagen.

The size and the shape of the plugs may vary depending on the situation. For example, polymeric plugs mentioned previously may be machined, injection molded, extruded or solution cast. In one embodiment, the shape of the plug may be elongated and thin in order to facilitate delivery by a catheter device. These plugs may also possess a barb or side protrusion to prevent the plug from slipping out of the site once it is introduced to the damaged region of the ventricle. In other embodiments, the plug may be created in the shape similar to a screw or a helix. In one embodiment, the plug may be a polymeric material. In other embodiments, the plug may be a polymeric material with SS anchors for example, a plug with a stainless steel band with anchors for embedding the plug into the site of interest. The size of the plug may also vary. In one embodiment, the radial diameter of the plug may be from about 0.1 mm to about 5 mm. In other embodiments, the radial diameter of the plug may be about 0.2 mm to about 3 mm. In other embodiments, the length of the plug may be from about 1 mm to about 20 mm. In other embodiments, the length of the plug may be about 2 mm to about 12 mm. In addition to the size and shape of the plug, the number of plugs supplied to a region in the ventricle may also vary depending on the extent of damage and the condition of the subject. In one embodiment, the number of plugs supplied to the region may about 1 to about 200. In other embodiments, the number of plugs supplied to the region may be about 5 to about 50. In still further embodiments, the number of plugs supplied to the region may be about 2 to about 20.

In one embodiment, the plug may be a processed biocompatible biomaterial. This biomaterial may be advantageous for recruiting cells to the damaged region for additional strength to the site. One example of a biomaterial includes porcine derived Small Intestine Submucosa, termed SIS. This engineered biomaterial may be supplied from DePuy Inc and the Cook Group. It is available in sterile sheets. SIS includes the complete small intestinal sub-mucosa, including de-cellularized extracellular matrix (ECM) in a native configuration. It also includes important endogenous growth factors adhered to the matrix. SIS has previously been shown to recruit pluripotent bone marrow derived stem cells that adhere to the SIS and induce healing. SIS has previously been used to repair rotator cuff injuries, diabetic foot ulcers and hip joints. SIS has been shown to re-absorb after a period of approximately 3 to 4 months. After re-absorption, the healed live tissue has replaced the matrix. In one embodiment, small disks of SIS may be supplied to a region in the ventricle for example an infarct region. The SIS disks may provide similar recruitment of cells into the damaged myocardium. These cells may then transform into viable muscle tissue and may form contractile myocytes. In another embodiment a processed biocompatible biomaterial (e.g., SIS) may be used for structural reinforcement of an infarct region in combination with electrical stimulation such as implanting leads for pulsing the site to unload the infarct area before, during and/or after the structural component is introduced.

There are several methods that may be used to introduce any of the plugs described. An optimum approach for introduction of the plugs may include, but is not limited, to introduction to the infarct region and/or the border zone of an infarct region during an open-heart procedure; or through a minimally invasive procedure, for example, sub-xiphoid or percutaneous methods, for example, with an intra-ventricular catheter or transvascular catheter (venous or arterial). One embodiment for introducing the plugs to the infarct region may include directly introducing the plugs to the site during an open-heart surgical procedure.

One or more contrast agents and/or suitable treatment agent(s) may accompany the previously detailed components. The contrast agent or treatment agent may be dispersed into, conjugated to, or dissolved into the plug component prior to introduction to the infarct area. The contrast agents may be used for detection in X-ray or MR analysis. The agents that may accompany the reinforcing component(s) may include but are not limited to angiogenic agents, ACE inhibitors, angiotensin receptor blockers, SRCA pump (sarcoplasmic reticulum calcium pump) increasing agents, phospholamban inhibitors and anti-apoptotic drugs. These agents may be in the form of small molecules, peptides, proteins or gene products. The agents may be optionally conjugated to a component of the resin mix that makes a plug, dispersed in a plug solution prior to forming a plug, or dissolved in a plug solution prior to forming a plug, or packed into machined pockets or reservoirs in a plug to elicit a biological effect (e.g., improve implant adhesion, recruit cells, promote healing). One embodiment is to conjugate a peptide with a conserved region that mediates adhesion processes. Another embodiment includes the use of a specific peptide conjugate with a RGD (arginine-glycine-aspartic acid) motif or the peptide receptor to RGD, such as DDM (aspartate-aspartate-methionine) in the presence of the reinforcing component. In further embodiments, the RGD motif peptide may include von Willebrand factor, osteopontin, fibronectin, fibrinogen, vitronectin, laminin or collagen.

In the foregoing specification, the embodiments have been described with reference to specific exemplary embodiments. It will, however, be evident that various modifications and changes may be made without departing from the broader spirit and scope of the invention as detailed in the appended claims. The specification and drawings are, accordingly, to be regarded in an illustrative rather than a restrictive sense.

EXAMPLES

Example 1

In one example a 2-component gel may be injected via a dual needle catheter to an infarct region. One possible 2-component gel material may include Na-Alginate (component 1) which will likely ionically crosslink (often within seconds) when added to a soluble solution of calcium, barium and/or strontium (component 2). One potential crosslinker for the components may be $CaCl_2$ (calcium chloride). In one example, covalently conjugating a peptide or protein to some of the acid groups of the alginate may enhance a cellular response. For example, conjugation of RGD groups or gelatin may promote cell adhesion, since these are binding sites for cells. The amine (N) terminus of gelatin or RGD may be conjugated to the acid groups of alginate via carbodiimide chemistry, forming an amide. The reaction may be mediated to higher yield with fewer side products (such as the inactive N-acyl urea) by first forming an active ester with, for example, 1-hydroxybenzotriazole or N-hydroxy succinimide, before adding the peptide or protein. Side products and unreacted material may be removed by dialysis.

When used as an adjunct to cellular injection, the cells may be first mixed with the alginate or alginate-peptide conjugate. This mix is injected down one needle lumen, followed by an injection or simultaneous with an injection of calcium chloride solution. The gel may prevent the cells from migrating, but is sufficiently porous to allow for transport of nutrients and waste products. Concentrations and volumes: 1% Alginate (Protanal LF10/60, FMC Biopolymers)-2 parts, 3.2% Calcium Chloride dihydrate in water-1 part.

Example 2

In one example, a person with an mild or severe desynchrony (such as left bundle branch block), detectable through QRS duration, echocardiography, or other means, and with a history of a previous myocardial infarction, may first receive a catheter delivered injection of micronized porcine urinary bladder matrix (UBM) particulate (cryogenically ground UBM and resuspended at 5% weight/volume in PBS) to achieve alterations in the mechanical properties of the previous/scarred region. Following injections), implantation of a cardiac rhythm management device may be used to provide cardiac resynchronization therapy (CRT) to alter the desynchronized condition and alter the patient's progression to heart failure.

All of the COMPOSITIONS, METHODS and APPARATUS disclosed and claimed herein can be made and executed without undue experimentation in light of the present disclosure. While the compositions and methods of this invention have been described in terms of preferred embodiments, it are apparent to those of skill in the art that variations maybe applied to the COMPOSITIONS, METHODS and APPARATUS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method, comprising:
    identifying an infarct region within a ventricle of a heart of a subject;
    within seven weeks of a myocardial infarction event,
        applying electrical stimulation to the heart,
        introducing an immunotolerant or non-antigenic cell source, and
        introducing bioerodible particles wherein the particles carry at least one growth promoting agent;
    monitoring a remodeling process of the heart; and
    modifying the electrical stimulation in response to changes in the remodeling process.

2. The method of claim 1 wherein the growth promoting agent is at least one agent consisting of basic fibroblast growth factor (bFGF), platelet-derived growth factor-BB (PDGF-BB), platelet-derived growth factor-AB (PDGF-AB), transforming growth factor-alpha (TGF-α), TGF-β1, 2, or 3, granulocyte colony-stimulating factor (G-CSF), stem cell growth factor (SCF), stromal cell-derived factor-1 (SDF-1), human growth factor (HGF), insulin growth factor (IGF); or factors known to induce vascularization, vascular endothelial growth factor (VEGF), tumor necrosis factor-alpha (TNF-α), angiogenin, angiopoietin-1, Del-1, follistatin, pleiotrophin (PTN), proliferin, and vascular permeability factor (VPF).

3. The method of claim 1 wherein the bioerodible particles comprise a biocompatible functional acrylate and a reduced thiol-containing compound capable of forming a bioerodible matrix in a ventricle of a subject.

4. The method of claim 1 wherein the bioerodible particles comprise PLGA 50:50.

5. The method of claim 3 wherein the biocompatible functional acrylate comprises di-acryloyl polyethylene glycol.

6. The method of claim 3 wherein the reduced thiol-containing compound comprises poly-s-benzyl-L-cysteine.

7. The method of claim 1, wherein the growth promoting agent comprises a pro-fibroblastic agent.

* * * * *